United States Patent [19]

Hughes et al.

[11] B 4,002,746
[45] Jan. 11, 1977

[54] SYNTHESIS OF GON-4-ENES

[75] Inventors: Gordon Alan Hughes; Herchel Smith, both of Wayne, Pa.

[73] Assignee: Herchel Smith, Bryn Mawr, Pa.

[22] Filed: Jan. 15, 1964

[21] Appl. No.: 337,823

[44] Published under the second Trial Voluntary Protest Program on March 23, 1976 as document No. B 337,823.

Related U.S. Application Data

[63] Continuation-in-part of Ser. No. 228,384, Oct. 4, 1962, Pat. No. 3,850,911, which is a continuation-in-part of Ser. Nos. 57,904, Sept. 23, 1960, abandoned, and Ser. No. 91,341, Feb. 24, 1961, abandoned, and Ser. No. 137,535, Sept. 12, 1961, abandoned, and Ser. No. 195,000, May 15, 1962, abandoned, and Ser. No. 196,557, May 16, 1962, abandoned.

[30] Foreign Application Priority Data

Sept. 25, 1959 United Kingdom ............ 32619/59

[52] U.S. Cl. .................... 424/243; 260/239.55 C; 260/397.3; 260/397.45; 260/397.5

[51] Int. Cl.² ........................................ C07J 71/00
[58] Field of Search ............................... 260/397.4 /Machine Searched Steroids;

[56] References Cited

UNITED STATES PATENTS

| | | | |
|---|---|---|---|
| 2,744,122 | 5/1956 | Djerassi et al. ................. | 260/397.4 |
| 2,991,295 | 7/1961 | Magerlein et al. ............ | 260/397.5 |
| 3,032,552 | 2/1962 | Ringold et al. ............... | 260/239.55 |
| 3,046,273 | 7/1962 | Fried et al. .................. | 260/239.55 |

*Primary Examiner*—Elbert L. Roberts
*Attorney, Agent, or Firm*—Gordon W. Hueschen; Vito Victor Bellino

EXEMPLARY CLAIM

1. A therapeutic composition having progestational activity comprising as active ingredient a 17-aliphatic carboxylic acid ester of 17α-ethynyl-18-methyl-19-nortestosterone and a pharmaceutical carrier for said compound.

5 Claims, 5 Drawing Figures

SYNTHESIS OF GON-4-ENES

This application is a continuation-in-part of our prior-filed copending application Ser. No. 228,384 filed Oct. 4, 1962, now U.S. Pat. No. 3,850,911, issued Nov. 26, 1974, in turn a continuation-in-part of our prior-filed copending applications Ser. Nos. 57,904 filed Sept. 23, 1960 ; 91,341 filed Feb. 24, 1961; 137,535 filed Sept. 12, 1961; 195,000 filed May 15, 1962; and 196,557 filed May 16, 1962, all now abandoned.

This invention relates to compositions of matter classified in the art of chemistry as substituted unsaturated gonane derivatives, and to processes for making and using such compositions.

The invention sought to be patented in principal composition aspect is described as residing in the concept of a gon-4-ene nucleus having attached thereto in the 13-position a monovalent polycarbonalkyl radical.

The tangible embodiments of the composition aspect of the invention possess the inherent general physical properties of being white crystalline solids, are substantially insoluble in water and are generally soluble in polar solvents such as dimethylacetamide. Examination of compounds produced according to the hereinafter described process reveals, upon ultraviolet and infrared spectrographic analysis, spectral data supporting the molecular structures herein set forth. The aforementioned physical characteristics, taken together with the nature of the starting materials and the mode of synthesis, confirm the structure of the compositions sought to be patented.

The tangible embodiments of the invention possess the inherent applied use characteristics of exerting qualitatively varying hormonal effects in animals as evidenced by pharmacological evaluation according to standard test procedures. Such tangible embodiments show androgenic, anti-estrogenic, progestational, blood lipid effects, and anabolic actions, salt retention, salt excretion and central nervous system effects. This finding indicates their usefulness in the treatment of amenorrhea, dysmenorrhea, ovulation block and contraception, functional uterine bleeding, arteriosclerosis, hormone dependent tumors, infertility, pregnancy maintenance, habitual abortion, weight gain and nitrogen retention, growth stimulation, post operative recovery, healing of wounds, and healing of burns. In particular, it has been established that alterations of the natural steroid structure made possible by our discovery result not merely in a change of degree of hormonal activity, but, as a result of the separation of types of hormonal activity, alter in an unexpected way its basic nature so that a desirable hormone effect is maximized and an undesirable hormone effect is minimized. Furthermore, said tangible embodiments possess the use characteristic of being intermediates for the preparation of composition exerting hormonal effects as evidenced by standard test procedures.

The invention sought to be patented in a sub-generic composition aspect is described as residing in the concept of a 13,17-dialkyl-17-hydroxygon-4-en-3-one (FIG. 1, XV), of which a specific embodiment, 13β,17α-diethyl-17β-hydroxygon-4-en-3-one, is hereinafter described.

The tangible embodiments of said sub-generic composition aspect possess the use characteristic of varying hormone effects in animals as evidenced by pharmacological evaluation by standard test procedures. In clinical tests, said specific embodiment has demonstrated high anabolic potency and unexpected separation of anabolic and androgenic activities.

The invention sought to be patented in a second sub-generic composition aspect is described as residing in the concept of a 13-alkyl-17-alkynyl-17-hydroxygon-4-en-3-one (FIG. 4, XX), of which a specific embodiment wherein the alkyl group is 13β-ethyl and the alkynyl group is 17α-ethynyl is hereinafter described.

The tangible embodiments of said second sub-generic composition aspect possess the use characteristic of varying hormone effects in animals, as evidenced by pharmacological evaluation by standard test procedures, and in particular have demonstrated a high progestational activity, coupled with an unexpected separation of activities.

The invention sought to be patented in a third sub-generic composition aspect is described as residing in the concept of a 17 ester of a 13-alkyl-17-hydroxygon-4-en-3-one (FIG. 5, XXIII), of which a specific embodiment in which the alkyl group is 13β-ethyl and the ester is the decanoate ester is hereinafter described.

The tangible embodiments of said third sub-generic composition aspect possess the use characteristic of varying hormone effects in animals, as evidenced by pharmacological evaluation by standard test procedures, and in particular in certain instances long-acting anabolic effects accompanied by unexpected separation of activities.

The invention sought to be patented, in a principal process of making the compositions aspect, is described as residing in the concept of the sequence of reactions including: converting a compound having a 5-phenyl-pent-1-yne nucleus, ring-unsubstituted in at least one position ortho to the point of chain attachment, by means of a Mannich-type reaction, to its acetylenic amine derivative; hydrating the acetylenic linkage to form a 3-keto compound; reacting such 3-keto substrate compound with a nucleophilic 2-monovalent alkyl-1,3-dioxocyclopentano compound under Michael condensation conditions to attach the cyclopentano compound through its 2-position carbon atom to the 1-position carbon atom of the 3-keto compound; treating the bicyclic triketone formed in the preceding step with an acidic dehydrating agent thereby to effect a double cyclodehydration to form a 1,3,5(10),8,14-pentadehydro-13-alkyl-gonane; selectively saturating the 14(15) double bond of said gonane with hydrogen in the presence of a catalyst; thereafter saturating the 8(9) double bond of the compound resulting from the preceding step; partially reducing the A-ring double bonds and the 17-carbonyl group to 17-hydroxymethylene; and, thereafter converting the so-reduced compound to a 4-dehydro-13-alkyl-17-hydroxygonane.

The invention sought to be patented in a second process aspect, as illustrated in annexed FIG. 2, is described as residing in the concept of a reaction comprising hydrolyzing a compound with a gona-2,5(10)-diene nucleus, having attached thereto in the 13-position a monovalent polycarbon-alkyl radical (XVI), under strong conditions, i.e. heat, mineral acid, to obtain a compound with a gon-4-en-3-one nucleus having attached thereto in the 13-position a monovalent polycarbonalkyl radical (XVII).

The invention sought to be patented in a third process aspect, as illustrated in annexed FIG. 3, is described as residing in the concept of a sequence of reactions including: treating a compound with a gona- 2,5(10)-dien-17-one nucleus having attached thereto in the 13-position a monovalent polycarbon-alkyl radical (XVIII) with an alkyl Grignard reagent or metal alkyl to obtain a compound with a 17α-alkyl-gona-2,5(10)-dien-17-ol nucleus having attached thereto in the 13-position a monovalent polycarbon-alkyl radical (XIV), and hydrolyzing said product with mineral acid to obtain a compound with a 17α-alkyl-17β-hydroxygon-4-en-3-one nucleus having attached thereto in the 13-position a monovalent polycarbon-alkyl radical (XV).

The invention sought to be patented in a fourth process aspect, as illustrated in annexed FIG. 4, is described as residing in the concept of a sequence of reactions including: treating a compound with a gona-2,5(10)-dien-17-one nucleus having attached thereto in the 13-position a monovalent polycarbon-alkyl radical (XVI) with an organo-metallic derivative of a 1-alkyne to obtain the corresponding 17α-alkynyl-gona-2,5(10)-dien-17-ol having attached thereto in the 13-position a monovalent polycarbon radical (XIX), and hydrolyzing said product with mineral acid to obtain a 17α-alkynyl-17β-hydroxygon-4-en-3-one having attached thereto in the 13-position a monovalent polycarbon-alkyl radical (XX).

The invention sought to be patented in a fifth process aspect, as illustrated in annexed FIG. 5, is described as residing in the concept of a sequence of reactions including: treating a compound with a gona-2,5(10)-dien-17-ol nucleus having attached thereto in the 13-position a monovalent polycarbonalkyl radical (XXI) with mineral acid to obtain a compound with a 17-hydroxygon-4-en-3-one nucleus having attached thereto in the 13-position a monovalent polycarbon-alkyl radical (XXII), and esterifying the hydroxy group to obtain the corresponding 17-ester (XXIII).

The manner of making the chemical compounds, which are the starting materials for use in making the compounds of the invention, and for use in the processes of making of the invention, are illustrated in co-pending application Ser. No. 228,384 filed Oct. 4, 1962.

In describing the invention, reference will be made in the following specification to the annexed drawings, wherein.

Figure 1:
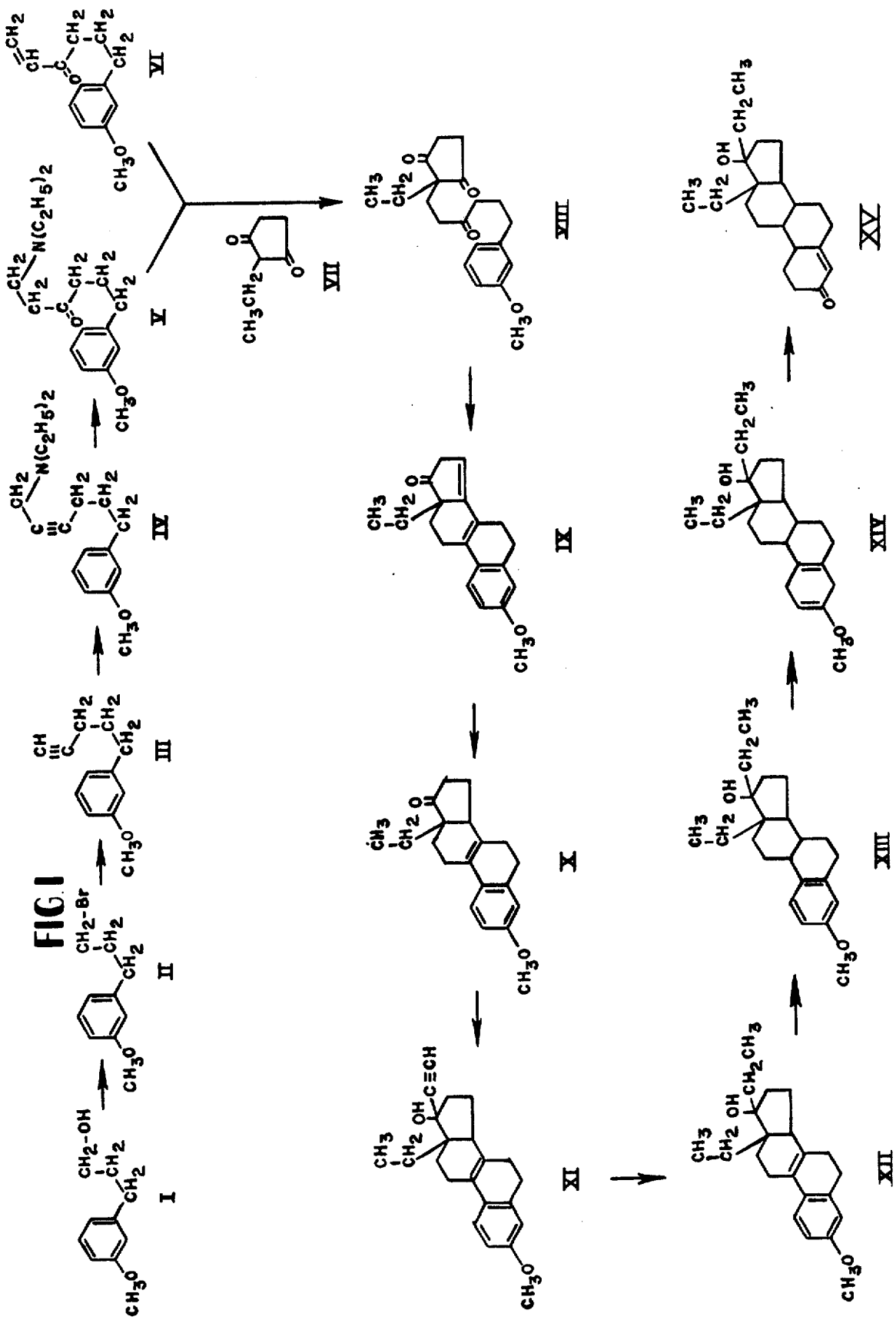
FIG. 1 illustrates schematically the reaction sequence for preparing a 13-alkylgon-4-ene, specifically 13β,17α-diethyl-17β-hydroxygon-4-en-3-one.
Figure 2:
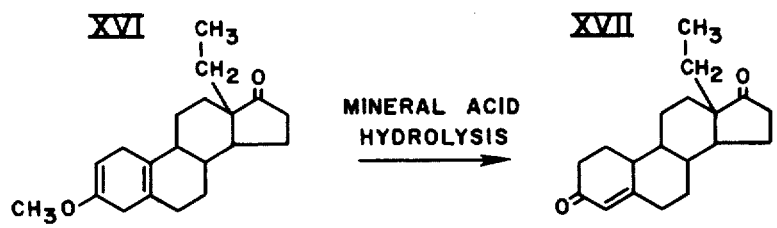
FIG. 2 illustrates schematically the mineral acid hydrolysis of a 13-alkylgona-2,5(10)-diene to a 13-alkylgon-4-ene, specifically 13β-ethyl-3-methoxygona-2,5(10)-dien-17-one to 13β-ethylgon-4-en-3,17-dione.
Figure 3:
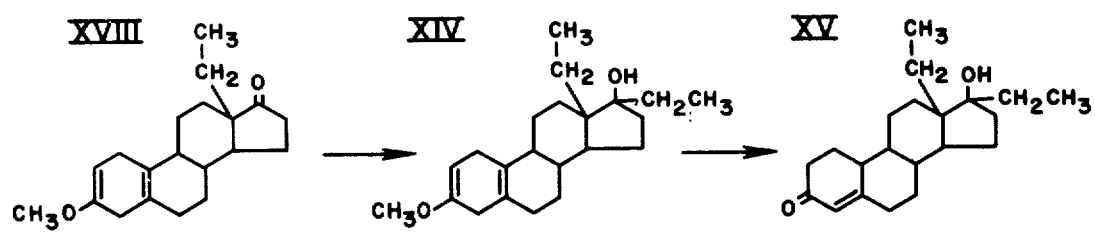
FIG. 3 illustrates schematically the reaction sequence for preparing a 13,17-dialkylgon-4-en-17-ol from a 13-alkylgona-2,5(10)-dien-17-one, specifically 13β,17α-diethyl-17β-hydroxygon-4-en-3-one from 3-methoxy-13β-ethylgona-2,5(10)-dien-17-one.

The manner and process of making and using the invention will now be generally described so as to enable a person skilled in the art of chemistry to make and use the same, as follows:

Referring now to FIG. 1, wherein the compounds are assigned Roman numerals for identification schematically, the sequence of reactions involved in the synthesis of a specific embodiment, namely, 13β,17α-diethyl-17β-hydroxygon-4-en-3-one, is illustrated. 3-(m-Methoxyphenyl)propanol (I) is heated with phosphorus tribromide in benzene after dropwise addition in the cold to form 3-(m-methoxyphenyl)propyl bromide (II). This halogen compound (II) dissolved in tetrahydrofuran is condensed with sodium acetylide in liquid ammonia to obtain 5-(m-methoxyphenyl)-1-pentyne (III). Compound III is allowed to stand under nitrogen with water, 30% formalin, acetic acid, diethylamine, dioxan, and cuprous chloride at 70°C for about 12 hours, whereby there is obtained 1-diethylamino-6-(m-methoxyphenyl)-2-hexyne (IV), which is in turn hydrated in the presence of a mercury salt and sulfuric acid to form 1-diethylamino-6-(m-methoxyphenyl)-3-hexanone (V). The ketamine (V) may eliminate diethylamine on distillation to give the vinyl ketone 6-(m-methoxyphenyl)-1-hexen-3-one (VI). Either the ketamine (V) or the ketone (VI), or mixtures thereof, is then reacted with 2-ethyl-1,3-cyclopentanedione (VII) under Michael condensation conditions, e.g. refluxing in methanolic potassium hydroxide to form 2-ethyl-2-[6-(m-methoxyphenyl)-3-oxohexyl]-1,3-cyclopentanedione (VIII).

Compound VIII is then cyclodehydrated at the reflux temperature of a solvent, such as benzene, in the presence of a dehydrating acid, such as p-toluene sulfonic acid, to effect simultaneous ring closures to give the tetracyclic compound 13β-ethyl-3-methoxygona-1,3,5(10),8,14-pentaen-17-one (IX). The 14-unsaturation of Compound IX is then selectively hydrogenated in the presence of a metal catalyst, such as 2% palladized calcium carbonate, to form 13β-ethyl-3-methoxygona-1,3,5(10),8-tetraen-17-one (X). Ethynylation at the 17-position of Compound X with lithium acetylide in dimethylacetamide gives 13β-ethyl,17α-ethynyl-3-methoxygona-1,3,5(10),8-tetraen-17β-ol (XI). The ethynyl group of Compound XI is then selectively hydrogenated to ethyl, as in the presence of a supported palladium catalyst, to produce 13β,17α-diethyl-3-methoxygona-1,3,5(10),8-tetraen-17β-ol (XII), which is then converted to 13β,17α-diethyl-3-methoxygona-1,3,5(10)-trien-17β-ol (XIII) by alkali metal reduction in liquid ammonia, to provide the normal gonane configuration of 9,8-8,14-14,13 exocyclic substituents, namely trans-anti-trans.

By alkali metal reduction in liquid ammonia in the presence of a proton donor, such as ethanol (Birch reduction), Compound XIII is converted to 13β,17α-diethylgona-2,5(10)-dien-17β-ol (XIV). By hydrolysis in the presence of mineral acid, Compound XIV is then converted to 13β,17α-diethyl-17β-hydroxygon-4-en-3-one (XV).

The compound 13β,17α-diethyl-17β-hydroxygon-4-en-3-one, when administered to humans, is strongly anabolic as measured by weight gain, and shows virtually no androgenicity at therapeutic dose levels. Consistent effects on appetite stimulation are present and beneficial effects upon dermatitis and ichthyosis of mongols have been noted.

Figure 4:
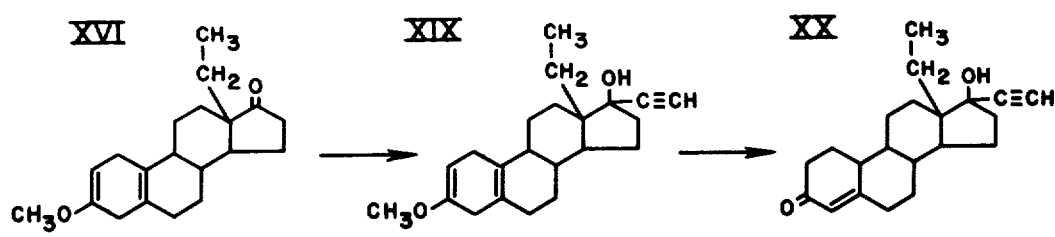
FIG. 4 illustrates schematically the reaction sequence for preparing a 13-alkyl-17-alkynylgon-4-en-17-ol from a 13-alkylgona-2,5(10)-dien-17-one, specifically 13β-ethyl-17α-ethynyl-17β-hydroxygon-4-en-3-one from 13β-ethyl-3-methoxygon-2,5(10)-dien-17-one.

To form another specific embodiment of this invention, referring to FIG. 4, Compound XVI, 13β-ethyl-3-methoxygona-2,5(10)-dien-17-one is treated with an alkali metal acetylide in liquid ammonia to convert it to 13β-ethyl-17αethynyl-3-methoxygona-2,5(10)-dien-17β-ol (XIX). Compound XIX is then converted to 13β-ethyl-17α-ethynyl-17β-hydroxygon-4-en-3-one (XX).

When administered orally, this compound, 13β-ethyl-17α-ethynyl-17β-hydroxygon-4-en-3-one, demonstrates unexpected high progestational activity accompanied by a separation of undesirable hormone effects found in the natural steroids.

Figure 5:
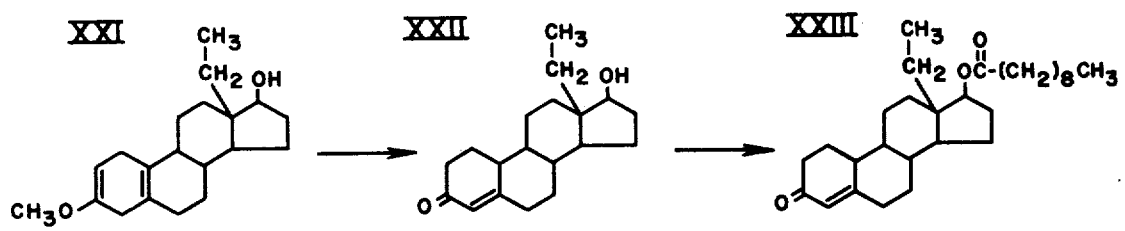
FIG. 5 illustrates schematically the reaction sequence for preparing an ester of a 13-alkyl-17-hydroxygon-4-ene from a 13-alkylgona-2,5(10)-dien-17-ol, specifically the decanoate ester of 13β-ethyl-17β-hydroxygon-4-en-3-one from 13β-ethyl-3-methoxygona-2,5(10)-dien-17β-ol.

Referring to FIG. 5, a third specific embodiment of the invention, 13β-ethyl-17β-hydroxygon-4-en-3-one decanoate ester (XXIII), is formed by esterification of 13β-ethyl-17β-hydroxygon-4-en-3-one (XXII), obtained by mineral acid hydrolysis of 13β-ethyl-3-methoxygona-2,5(10)-dien-17β-ol (XXI). Compound XXI is obtained from 13β-ethyl-3-methoxygona-2,5(10)-dien-17-one, by reduction with a complex metal hydride, or alternatively from Compound X, FIG. 1, 13β-ethyl-3-methoxygona-1,3,5(10),8-tetraen-17-one, by complex metal hydride reduction to form 13β-ethyl-3-methoxygona-1,3,5(10),8-tetraen-17β-ol, and then alkali metal in liquid ammonia reduction to obtain 13β-ethyl-3-methoxygona-1,3,5(10)-trien-17β-ol, followed by alkali metal in liquid ammonia reduction in the presence of a proton donor to form the before-mentioned Compound XXI.

The compound 13β-ethyl-17β-hydroxygon-4-en-3-one decanoate ester (XXIII) is a long acting anabolic agent with unexpected enhancement of anabolic activity accompanied by a decrease in androgenic activity.

While the hereinbefore described processes produce novel and steroidal-like compounds which have an unnatural substituent at the 13-position, it is apparent that the novel and valuable processes of the invention offer a unique feasible route to the corresponding natural steroids if the nucleophilic compound used in the Michael condensation step is 2-methyl-1,3-cyclopentanedione.

The aromatic ring of the phenylpropanol (FIG. 1, I) used as the starting material for the preparation of the compositions and initial preparations of the invention may have one or more substituents, provided, however, at least one position ortho to the position of propanol-chain attachment is unsubstituted so that cyclodehydration to form a cyclic structure can eventually be effectuated. To activate such ortho position for said subsequent ring closure, a para-directing group (referring to electrophilic aromatic substitution) such as hydroxy, acyloxy, alkoxy, amino, alkylamino, or acylamino is a necessary substituent on the aromatic ring. The group may be present initially or may be introduced later but before ring closure, either directly, or by conversion from a meta-directing group such as nitro. After the tetracyclic structure has been formed, substituents can be introduced into the aromatic A-ring which are not limited as above; however, if such substituted compound is to undergo a reduction, the group is preferably one not sensitive to reduction. After the A-ring has been reduced, the substituents on said A-ring may be the same as those originally present, or substituents on said A-ring may be the same as those originally present, or substituents to which they may be converted, such as ketonic oxygen, dialkoxy, alkylenedioxy, alkylenethioxy, and alkylenedithio; or groups introducible by known processes, such as halogen or alkyl. For the processes of the invention and except for the limitations expressed in this specification, variations of the substituents on the A-ring of the fully formed tetracyclic structures, or on the intermediates leading thereto, are full equivalents of each other.

The carbon atom to which the phenyl group of the starting propanol (I) is attached can be substituted, as, for example, with an alkyl group, such as methyl or ethyl. Moreover, this atom, to which the phenyl group is attached in Compound I, need not necessarily be carbon. It can be a hetero atom which would not interfere with subsequent catalytic reductions, as, for example, oxygen or nitrogen. This atom will appear in the tetracyclic structures of the invention in the 6-position, and it will be apparent, may be, in the case of the nitrogen, substituted with hydrogen or an alkyl group.

The 2-carbon atom of the starting phenyl-propanol (I) can also be substituted, as, for example, with an alkyl group, such as methyl and ethyl, and, as such, be unchanged throughout the subsequent synthesis. In the tetracyclic structures of the invention this carbon atom will appear in the 7-position.

For the processes of the invention and except for the limitations expressed in this specification, variations of the B-ring on the fully formed tetracyclic structures, or on the intermediates leading thereto, are full equivalents of each other.

In the Michael reaction step, the 3-keto substrate compound can be a 6-phenyl-1-hexen-3-one, or alternatively, a 6-phenyl-3-hexanone having attached to the 1-position a group which will eliminate with hydrogen to form a 6-phenyl-1-hexen-3-one under Michael conditions. Thus, a 3-keto compound with a 1-dialkylamino substituent or its quarternary salt, a 1-halo substituent or a 1-hydroxy substituent will react with the nucleophilic compound to form the Michael product. The nucleophilic compound can be a carbocyclic-1,3-dione of varying ring size, as, for example, a five-membered ring, a six-membered ring, etc., ultimately forming a corresponding five-membered, a six-membered, etc., D-ring in the tetracyclic structure. The 1,3-cyclodione may also contain a hetero atom at positions other than position 2, thereby to provide a heterocyclic D-ring in the tetracyclic structure. Acylic nucleophilic compounds can be used in conducting the Michael reaction step and the open-chain of the resulting product thereafter ring-closed to form a cyclic D-ring.

For the processes of the invention, and except for the limitations expressed in this specification, variations of the D-ring on the fully formed tetracyclic structure, or on the intermediates leading thereto, are full equivalents of each other.

When the nucleophilic compound is 2-methyl-1,3-cyclopentanedione, the invention provides a unique total synthesis for natural steroids: the hydrogens at the 8-position, 9-position, and 14-position being β, α, and α, respectively, as in the natural steroids. Thus such valuable therapeutic substances as 19-nortestosterone are made available from easily obtainable and relatively simple and inexpensive starting materials.

Moreover, by varying the group at the 2-position of the nucleophilic Michael condensation reactant, the invention provides a way to produce compounds resembling the natural steroids save at the 13-position. Thus, by varying the substituent at the 2-position of the 1,3-cyclopentanedione, alkyl groups of varying chain length such as, for example, ethyl, isopropyl, cetyl, etc., may be introduced to form the gonane correspondingly substituted at the 13-position. Further, gonanes may be prepared wherein the 13-position is substituted with any organic radical. Thus, but without limiting the generality of the foregoing, an aralkyl, cycloalkylalkyl, or a polycarbon-alkylene bridge bearing a hydroxy-, amino-, or alkylamino- substituent can readily be placed in the 13-position, and from such compounds other variations of the 13-position substituent can be prepared, as haloalkyls from hydroxyalkyls, or quaternary salts, amides, alkenyls, etc. from aminoalkyls.

For the processes of the invention and except for the limitations expressed in this specification, variations at the 13-position of the fully formed tetracyclic structures or on the intermediates leading thereto are the full equivalents of the claimed 13-position polycarbonalkyl substituents, having physiological activity of the same type.

In any of the intermediate structures or in the tetracyclic structures of the invention having either an aromatic, partially reduced, or totally reduced A-ring, wherein the 17-position, or position corresponding thereto in the gonane nucleus, is carbonyl, the carbonyl group can be converted to a group such as hydroxymethylene by lithium aluminum hydride reduction; to acyloxymethylene by esterification of the hydroxymethylene group so formed; to alkoxymethylene by etherification of the hydroxymethylene group; to alkylhydroxymethylene by addition of the appropriate organo-metallic reagent to the carbonyl; or to alkynylhydroxymethylene by addition of the appropriate alkali metal acetylide in a suitable inert solvent; all in the known manners. The carbonyl group may also be ketalized or thioketalized by treating with the appropriate alcohol or glycol in a suitable solvent under acidic conditions, as in the presence of an acid such as sulfuric acid, p-toluene sulfonic acid, or boron trifluoride etherate, with heating where necessary, according to the known art.

The specific reactions involved in the processes of the invention will now be considered, as follows, reference being made to the drawings for typifying compounds:

The vinyl ketones (VI) of the invention are prepared by elimination of dialkylamine from the corresponding dialkylaminoethyl aminoketones (V), obtained by hydration of the acetylenic linkage in an acetylenic amine (IV). The acetylenic amines (IV) can be themselves prepared by a Mannich reaction from the corresponding acetylene (III) with formaldehyde and a dialkylamine. The hydration can be carried out, for example, in aqueous sulfuric acid with mercuric sulfate as a catalyst. The corresponding quaternary salts, which may also be used in the subsequent Michael condensation, can be obtained by quaternization of the corresponding acetylenic dialkylaminoethyl amine, followed by hydration; or by quaternization of the ketoamine. The vinyl ketones can be prepared from these derivatives by the above elimination reaction. Thus the ketoamine or its quaternary salt can be treated with a base for this purpose, for example, with sodium hydroxide or a sodium alkoxide.

The vinyl ketones (VI) and dialkylamino ketones (V) are condensed with a nucleophilic compound under Michael reaction conditions. Thus the condensation can be carried out by bringing the two reagents together in solution in the presence of a base, for example, pyridine, triethylamine, diethylamine, sodium hydroxide, or sodium methoxide, and heating as required. The nature and amount of base employed in the condensation reaction will depend upon the particular reagents used. Where the vinyl ketone derivative employed is a keto-amine and dialkylamine is eliminated in the reaction, no added base may be required. Where the compound is a 2-alkylcyclopentane-1,3-dione (VII), the compound to be condensed with it is preferably a vinyl ketone, and the dione is used in excess of the molecular equivalent quantity. Suitable solvents are hydrocarbons, such as benzene, and anhydrous alcohols, such as methanol. If the reaction is carried out in benzene under refluxing conditions, water formed in the condensation may be azeotroped out of the reaction mixture with a Dean-Stark type trap.

As hereinbefore noted, monocyclodehydration of the C-ring is accomplished by an internal aldol condensation. The cyclodehydration can therefore be carried out using conditions generally applicable for an aldol condensation, i.e., in the presence of an acid or basic catalyst such as NaOH, p-toluene sulfonic acid, triethylamine benzoate, aluminum tertiary butoxide, and the like, either at room temperature or accompanied by heating if necessary. In most instances, we prefer to carry out the cyclic dehydration at the boiling point of the solvent to permit azeotropic removal of the water formed during the course of the reaction, inasmuch as the aldol reaction is an equilibrium one. Preferred as solvents are the low boiling anhydrous aromatic hydrocarbons, such as benzene and xylene. C-ring closure occurs regardless of the nature of the substitution on the aromatic ring.

The reduction of the 8(14) unsaturation in the tricyclic compounds is carried out by catalytic hydrogenation either at room temperature or above. It is found that when hydrogen and a palladium-on-charcoal catalyst are used, the hydrogen introduced at the carbon 14-position is principally in the configuration trans to the group attached at the 13-position. By whatever mechanism the hydrogen at the 8-position is introduced, it can on treatment with an acid or base take up the most stable configuration, i.e., the position trans to the other newly introduced hydrogen, by equilibrating through keto-enol tautomerism with the adjacent keto group. Thus the second hydrogen atom can be made to take up the $\beta$-configuration when the first is $\alpha$.

The B-ring closure is brought about under acidic conditions. Suitable are strong acids such as sulfuric, hydrochloric, p-toluene sulfonic, etc. in solvents such as benzene, toluene, anhydrous alcohol, etc. The reaction is generally carried out at room temperature or below since heat may promote the formation of an aromatic B-ring. The preferred treatment is with methanolic hydrochloric acid at room temperature. As hereinbefore noted, it has been found that the ease of B-ring closure of the compounds of the invention to form tetracyclic compounds is affected by the nature of the substituent present on the preformed aromatic A-ring, and that subsequent cyclization is easier to carry out when the preformed aromatic A-ring contains a substituent which activates the position at which cyclization is to occur. Where a compound is to be used directly for B-ring closure, it will in practice be one containing such a substituent. Those substituents which cause subsequent B-ring closure to occur readily are substituents para to the position of ring closure which are groups that in electrophilic aromatic substitution activate an aromatic ring and are predominantly o- and p- directing; for example, the hydroxy or alkoxy group.

The double cyclodehydration is brought about by dissolving a compound typified by Compound VIII in benzene containing a catalytic amount of p-toluene sulfonic acid and boiling the mixture under a Dean-Stark trap until two equivalents of water have been collected, or alternatively, by treating the same triketone with polyphosphoric acid at room temperature or slightly above until ring closure is complete.

The selective hydrogenation of the gona-8,14-dienes typified by Compound IX is carried out by means of 2% palladized calcium carbonate. As hereinbefore noted, surprisingly, the catalytic hydrogenation results in addition of hydrogen to the 14-double bond in such a way as to give the "natural" stereochemical configuration; that is, the hydrogen adds at 14-trans to the alkyl at 13. Selective reduction of the 14-trans to the alkyl at 13. Selective reduction of the 14-ethylenic linkage is achieved by use of catalyst-solvent combination which shows adequate selectively, and stopping the hydrogenation when the theoretical amount of hydrogen has reacted. Solvents showing selectivity in this regard are the nonprotonic solvents, that is, hydrocarbons and ethers; benzene, toluene, naphtha, dioxan, dibutyl ether, and diethyl ether are examples of suitable nonprotonic solvents. On the other hand, protonic solvents such as acetic acid and ethanol appear to be largely non-selective.

It has been found that a moderately active Raney nickel catalyst provides good selectivity in a suitable solvent. If a Raney nickel catalyst of low activity is employed, the hydrogenation may be too slow to be useful; on the other hand, a vigorous catalyst shows poor selectivity and some saturation of the 8,9-ethylenic bond may occur simultaneously with the hydrogenation at the 14,15-position.

If desired, other moderately active hydrogenation catalysts may be used instead of Raney nickel; for example, palladium on barium sulfate or on an alkaline earth metal carbonate or on charcoal have all been found suitable in this selective hydrogenation.

Saturation at the 8- or at the 9(11)-position of the tetracyclic structures must be stereospecific to obtain the natural type of exocyclic substituent configuration as noted supra. Such a sufficiently stereospecific reduction can be in general effected by the action of an alkali metal (sodium, potassium, or lithium) in liquid ammonia to the normal steroid configuration hydrogen at the respective carbons. Preferably this type of reduction is carried out in the presence of a primary or secondary aromatic amine, for instance aniline, p-toluidine, or diphenylamine, as this can improve the yield of the desired product. The reduction can also be carried out in the presence of a more reactive proton donor; in this instance, the reduction of the ethylenic linkage occurs with a simultaneous reduction of the aromatic ring to give a 1,4-dihydrophenyl group.

The reduction of 9-dehydro compounds can also be effected by catalytic hydrogenation, as this has been discovered to be sufficiently stereospecific for production of the desired trans-anti-trans compounds of normal configuration.

While the tetracyclic compounds in this specification and the appended examples are named to describe the configuration corresponding to that of the natural steroids, it is to be understood that unless otherwise indicated, the product of each of the given manipulative procedures is a racemic mixture which contains said named compound and its enantiomorph.

Representative formulations embodying specific compositions of this invention follow:

A pharmaceutical tablet for use as an oral anabolic agent consists of the following ingredients:

| | mg |
|---|---|
| 13$\beta$,17$\alpha$-Diethyl-17$\beta$-hydroxygon-4-en-3-one | 5 |
| Carboxymethylcellulose (viscosity 400 cps) | 15 |
| Lactose powder | 25 |
| Redried corn starch | 25 |
| Magnesium stearate powder | 4 |
| Calcium silicate powder | q.s. |
| | 200 |

A capsule for use as an oral anabolic agent contains, in encapsulating gelatin, the following ingredients:

| | mg |
|---|---|
| 13$\beta$,17$\alpha$-Diethyl-17$\beta$-hydroxygon-4-en-3-one | 5 |
| Finely divided silica lubricant | 5 |
| Magnesium stearate powder | 5 |
| Powdered corn starch | 113 |
| Lactose powder | q.s. |
| | 245 |

An anabolic agent suspension for oral use consists of the following ingredients per 5 cc:

| | mg |
|---|---|
| 13$\beta$,17$\alpha$-Diethyl-17$\beta$-hydroxygon-4-en-3-one | 5.0 |
| Magnesium aluminum silicate (thickening agent) | 37.5 |
| Carboxymethylcellulose of low viscosity | 37.5 |
| Polyoxyethylene sorbitan monolaurate | 50.0 |
| Glycerin | 250.0 |
| Sucrose | 2000.0 |
| Methyl p-hydroxybenzoate | 5.0 |
| Propyl p-hydroxybenzoate | 1.0 |
| Flavor and distilled water | q.s. |

An anabolic agent suspension for parenteral use consists of the following ingredients per cc:

| | mg |
|---|---|
| 13$\beta$,17$\alpha$-Diethyl-17$\beta$-hydroxygon-4-en-3-one | |
| Benzyl alcohol | 10.0 |
| Sodium chloride | 90.0 |
| Polyoxyethylene sorbitan monooleate | 4.0 |
| Sodium carboxymethylcellulose | 5.0 |
| Water for injection | q.s. |

Pediatric drops for use as an anabolic agent consist of the following ingredients per drop (0.05 cc):

| | mg |
|---|---|
| 13$\beta$,17$\alpha$-Diethyl-17$\beta$-hydroxygon-4-en-3-one | 0.500 |
| Magnesium aluminum silicate (thickening agent) | 0.375 |
| Polyoxyethylene sorbitan monolaurate | 0.500 |
| Disodium phosphate heptahydrate | 0.375 |
| Citric acid monohydrate | 0.060 |
| Glycerin | 1.250 |
| Methyl p-hydroxybenzoate | 0.025 |
| Propyl p-hydroxybenzoate | 0.005 |
| Butyl p-hydroxybenzoate | 0.020 |
| Distilled water | 0.015 |
| Sodium saccharin | 0.013 |
| Sorbitol and flavor | q.s. |

A long-acting anabolic agent tablet consists of the following ingredients:

| | mg |
|---|---|
| 13$\beta$,17$\alpha$-Diethyl-17$\beta$-hydroxygon-4-en-3-one | 5 |
| Water-insoluble acid carboxyvinyl polymer of acrylic acid copolymerized with 0.75-2% of polyallyl sucrose (the Carbopol 934 of U.S. Patent 2,909,462) | 150 |

-continued

| | |
|---|---|
| Magnesium stearate powder | 2 |
| Lactose | q.s. |

A long-acting anabolic agent suspension for parenteral use consists of the following ingredients per cc:

| | mg |
|---|---|
| 13β-Ethyl-17β-hydroxygon-4-en-3-one 17-decanoate | 0.5 |
| Benzyl alcohol | 10.0 |
| Sodium chloride | 90.0 |
| Polyoxyethylene sorbitan monooleate | 4.0 |
| Sodium carboxymethylcellulose | 5.0 |
| Water for injection | q.s. |

A progestational agent tablet consists of the following ingredients:

| | mg |
|---|---|
| 13β-Ethyl-17α-ethynyl-17β-hydroxygon-4-en-3-one | 5 |
| Spray dried lactose | 75 |
| Methocel (400 cps) | 12 |
| Powdered stearic acid | 6 |
| Talc | 2 |

Pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet-disintegrating agents: it can also be an encapsulating material. In powders the carrier is a finely divided solid which is in admixture with the finely divided compound. In the tablets the compound is mixed with carrier having the necessary binding properties in suitable proportions and compacted in the shape and size desired. The powders and tablets preferably contain from 5 to 10 to 99% of the active ingredient. Suitable solid carriers are magnesium carbonate, magnesium stearate, talc, sugar, lactose, pectin, dextrin, starch, gelatin, tragacanth, methyl cellulose, sodium carboxymethylcellulose, a low melting wax, and cocoa butter. The term "preparation" is intended to include the formulation of the compound with encapsulating material as carrier providing a capsule in which the compound (with or without other carriers) is surrounded by carrier, which is thus in association with it. Similarly, cachets are included. Tablets, powders, cachets, and capsules can be used for oral administration.

Liquid form preparations include solutions, suspensions, and emulsions. The compounds are insoluble in water, but can be dissolved in aqueous-organic solvent mixtures that are non-toxic in the amounts used. As an example may be mentioned water-propylene glycol solutions for parenteral injection. Liquid preparations can also be formulated in solution in aqueous polyethylene glycol solutions. Aqueous suspension suitable for oral use can be made by dispensing the finely divided compound in water with viscous material, natural or synthetic gums, resins, etc., for example, gum arabic, ion-exchange resins, methylcellulose, sodium carboxymethylcellulose and other well-known suspending agents.

Preferably the pharmaceutical preparation is in unit dosage form. In such form, the preparation is subdivided in unit doses containing appropriate quantities of the compound: the unit dosage form can be a packaged preparation, the package containing discrete quantities of preparation, for example, packeted powders of vials or ampules. The unit dosage form can be a capsule, cachet, or tablet itself, or it can be the appropriate number of any of these in packaged form. The quantity of compound in a unit dose of preparation may be varied or adjusted from 1 mg to 100 mg (generally within the range of 2.5 to 25 mg) according to the particular application and the potency of the active ingredient.

The claimed compositions having physiological activity can be incorporated into pharmaceutical formulations including sustained-release agents.

The following examples illustrate the processes and manner of making the compositions of the invention.

EXAMPLE 1

1-Dimethylamino-6-m-methoxyphenylhex-2-yne

Allow 5-m-methoxyphenylpent-1-yne (8 g.) to stand for 12 hours at 70°C under nitrogen with water (2.5 cc), trioxan (0.5 g), 30% formalin (5.5 g), diethylamine (4 g), acetic acid (2.75 g), dioxan (25 cc) and cuprous chloride (0.13 g). Make the cooled solution alkaline with 10% aqueous sodium hydroxide and extract with ether; then extract the ether extract with 10% hydrochloric acid: wash the acid extract with ether, make alkaline with 10% aqueous sodium hydroxide, extract with ether, and then wash and dry the ether extract. Distil to obtain 1-diethylamino-6-m-methoxyphenylhex-2-yne (10.6 g. 88%), b.p. 130°–131°C/0.1 mm.

$C_{17}H_{25}N$ Calculated: C, 78.7%; H, 9.7%. Found: C, 78.9%; H, 9.6%.

To prepare 1-diethylamino-6-m-ethoxyphenyloct-2-yne treat 5-m-ethoxyphenylhept-1-yne (ca. 8 g) according to the manipulative procedure described above.

To prepare 1-diethylamino-6-m-propoxyphenylhex-2-yne treat 5-m-propoxyphenylpent-1-yne (ca. 8 g) according to the manipulative procedure described above.

To prepare 1-diethylamino-6-m-pentoxyphenylhex-2-yne treat 5-m-pentoxyphenylpent-1-yne (ca. 8 g) according to the manipulative procedure described above.

To prepare 1-diethylamino-6-m-cyclopentyloxyphenylhex-2-yne treat 5-m-cyclopentyloxyphenylpent-1-yne (ca. 8 g) according to the manipulative procedure described above.

To prepare 1-diethylamino-6-m-propoxyphenylhep-2-yne treat 5-m-propoxyphenylhex-1-yne (ca. 8 g) according to the manipulative procedure described above.

To prepare 1-diethylamino-6-(3,5-diethoxyphenyl)-hex-2-yne treat 5-(3,5-diethoxyphenyl)pent-1-yne (ca. 8 g) according to the manipulative procedure described above.

To prepare 1-diethylamino-6-(3-ethoxy-4-propoxyphenyl)-hex-2-yne treat 5-(3-ethoxy-4-propoxy)pent-1-yne (ca 8 g) according to the manipulative procedure described above.

To prepare 1-diethylamino-6-(3-ethoxy-4-propoxyphenyl)-hept-2-yne treat 5-(3-ethoxy-4-propoxy)-hex-1-yne (ca. 8 g) according to the manipulative procedure described above.

EXAMPLE 2

1-Diethylamino-6-phenylhex-2-yne

Maintain 5-phenylpent-1-yne (20 g) for 12 hours at 70° under nitrogen with water (6.2 cc), trioxan (1.2 g), 30% formalin (13.8 g), diethylamine (10 g), acetic acid (6.9 g), dioxan (62 cc) and cuprous chloride (0.35 g). Make the cooled solution alkaline with sodium hydroxide. Extract with ether and extract the ether extract itself with hydrochloric acid. Make the purified aqueous hydrochloride solution thus obtained alkaline again and extract with ether. Dry, evaporate the ether extract and distil the residue to obtain 1-diethylamino-6-phenylhex-2-yne (27.1 g), b.p. 104°–106°/0.2 mm.

$C_{16}H_{23}N$ Calculated: C, 83.8%; H, 10.1%. Found: C, 83.9%; H, 10.1%.

Prepare 1-diethylamino-6-m-nitrophenylhex-2-yne (1.5 g), b.p. 148°C/0.05 mm, by treating 5-m-nitrophenylpent-1-yne (1.8 g) with water (0.6 cc), trioxan (0.1 g), 30% formalin (1.4 g), diethylamine (1g), acetic acid (0.7 g), dioxan (6.2 cc) and cuprous chloride (0.03 g) according to the manipulative procedure described above.

EXAMPLE 3

1-Diethylamino-6-m-acetoxyphenylhex-2-yne

Add 5-m-acetoxyphenylpent-1-yne (9.5 g) to a mixture of trioxan (0.5 g), 40% formalin (5.5g), diethylamine (4g), acetic acid (2.75 g), dioxan (25 cc), and cuprous chloride (0.13 g) at room temperature. Heat the mixture thus obtained to 70°, to obtain a clear green solution, and maintain under nitrogen at that temperature for 12 hours. Cool and add ice, pour the product into ice-cold saturated potassium bicarbonate and extract the mixture with ether. Wash and dry, evaporate the extracts under reduced pressure and distil to obtain 1-diethylamino-6-m-acetoxyphenylhex-2-yne (9.9 g), b.p. 152°–154°/0.1 mm, as a pale yellow mobile liquid.

EXAMPLE 4

1-Diethylamino-6-(3,4-methylenedioxyphenyl)-hex-2-yne

Add 5-(3,4-methylenedioxyphenyl)pent-1-yne (24.5 g) in dioxan (15 cc) to a mixture of diethylamine (16 g), trioxan (7.2 g) and cuprous chloride (0.3 g) in dioxan (20 cc) and heat the mixture at 100° for 15 hours under an atmosphere of nitrogen. Filter the cooled solution, remove the solvent and distil the residue at 0.1 mm Hg to obtain 1-diethylamino-6-(3,4-methylenedioxyphenyl)-hex-2-yne after a forerun of more volatile material.

Infrared absorption peaks at 6.25, 12.20$\mu$.

EXAMPLE 5

1-Diethylamino-6-(3,4-dimethoxyphenyl)-hex-2-yne

Heat a mixture of 5-(3,4-dimethoxyphenyl)-pent-1-yne (8 g), water (2.5 cc), trioxan (0.5 g ), 30% formalin (5.5 g), diethylamine (4 g), acetic acid (2.75 g), dioxan (25 cc) and cuprous chloride (0.13 g) at 70° for 15 hours. Make the cooled solution alkaline with 10% aqueous sodium hydroxide and collect the product. Wash the ethereal solution with water and extract with 10% hydrochloric acid (3 × 30 cc). Wash the combined aqueous extracts with ether, make it alkaline with 10% sodium hydroxide solution and extract with ether. Wash and dry the ethereal solution, evaporate the solvent and distil the residue at 0.1 mm Hg to obtain 1-diethylamino-6-(3,4-dimethoxyphenyl)-hex-2-yne.

Infrared absorption peaks at 6.25, 12.20 $\mu$.

Prepare 1-diethylamino-6-(3,5-dimethoxyphenyl)-hex-2-yne by treating 5-(3,5-dimethoxyphenyl)pent-1-yne with water, trioxan, 30% formalin, diethylamine, acetic acid, dioxan and cuprous chloride according to the manipulative procedure described above.

EXAMPLE 6

1-Diethylamino-6-(3-methoxyphenyl)-hept-2-yne

Heat a mixture of 5-(3-methoxyphenyl)-hex-1-yne (56.6 g), water (17.5 cc.), 40% formalin (38.5 cc), diethylamine (40 cc), acetic acid (19 cc), dioxan (175 cc) and cuprous chloride (1 g) at 70° for 16 hours in an atmosphere of nitrogen. Make the cooled solution alkaline with 10% aqueous sodium hydroxide and extract twice with ether. Wash the ether extracts with water, filter and extract with 4N hydrochloric acid (3 × 350 cc). Make the acid extracts alkaline with 10% aqueous sodium hydroxide, extract with ether and wash the organic solution with water, brine and dry. Evaporate the solvent and distil the residue to obtain 1-diethylamino-6-(3-methoxyphenyl)-hept-2-yne, 79.5 g. b.p. 135°–140°/0.2 mm Hg $n_D^{25}$ 1.5116.

$C_{18}H_{27}ON$ Calculated: C, 79.07%; H, 9.95%. Found: C, 78.99%; H, 9.67%.

EXAMPLE 7

1-Diethylamino-5-methyl-6-(m-methoxyphenyl)-hex-2-yne

Heat 5-(m-methoxyphenyl)-4-methyl-pent-1-yne (8 g), trioxan (0.5 g), 30% formalin (5.5 cc), diethylamine (4 g), acetic acid (2.75 g), dioxan (25 cc) and cuprous chloride (0.12 g) together at 70° for 15 hours. Make cooled solution alkaline with 10% aqueous sodium hydroxide and extract with ether. Wash the ethereal solution with water and extract with 10% hydrochloric acid (3 × 20 cc). Combine the acid extracts, wash with ether and make alkaline with 10% aqueous sodium hydroxide and extract with ether. Wash the ethereal solution, dry, remove the solvent and distil the residue at 0.1 mm to obtain 1-diethylamino-5-methyl-6-(m-methoxyphenyl)-hex-2-yne.

EXAMPLE 8

1-Diethylamino-6-m-methoxyphenylhexan-3-one and 6-m-Methoxyphenylhex-1-en-3-one Add mercuric sulphate (0.45 g) to a swirled solution of 1-diethylamino-6-m-methoxyphenylhex-2-yne (8.5 g) in concentrated sulphuric acid (2.5 cc) and water (25 cc). Keep the solution under nitrogen at 75°C for 1 hour, then cool, make basic with 10% aqueous sodium hydroxide, and filter through glass wool to remove mercuric oxide. Extract product with ether and wash and dry the ethereal solution. Remove the solvent to obtain the crude ketoamine 1-diethylamino-6-m-methoxyphenylhexan-3-one, infrared absorption peak at 1710 $\mu$. Distil under reduced pressure with partial elimination of diethylamine, to obtain a mixture of the ketoamine 1-diethylamino-6-m-methoxyphenylhexan-3-one and the vinyl ketone 6-m-methoxyphenylhex-1-en-3-one (7.1 g, ca. 76%), b.p. 140°–145°C/0.1 mm;

infrared absorption peaks at 5.85 and 5.95 μ, the ketoamine predominating.

Distil a second portion of the crude ketoamine 1-diethylamino-6-m-methoxyphenylhexan-3-one very slowly over a period of 30 minutes through a Vigreux fractionating column 10 cm high and one-inch diameter under reduced pressure to eliminate most of the diethylamine. Dissolve the 6-m-methoxyphenylhex-1-en-3-one obtained (b.p. 114°–114°C/0.7 mm) in ether and wash the ether solution with dilute hydrochloric acid, followed by aqueous sodium bicarbonate and water. Dry and evaporate. Distil the residue to give the pure vinyl ketone as a colorless liquid, b.p. 76°C/0.3 mm.

$C_{13}H_{16}O_2$ Calculated: C, 76.4%; H, 7.9%. Found: C, 76.3%; H, 8.0%.

Mix a third portion of the crude undistilled 1-diethylamino-6-m-methoxyphenylhexan-3-one (3g) with methyl iodide (3 g). An exothermic reaction soon develops. After 12 hours wash the mixture with ether to remove unchanged reactants and subject to reduced pressure (15 minutes) to remove ether remaining: the residue is the crude methiodide of the ketoamine (4.6 g).

Infrared absorption peaks at 5.85 μ.

This compound is useful for preparing the novel compositions of this invention which have hormonal activity.

EXAMPLE 9

1-Diethylamino-6-phenylhexan-3-one and 6-Phenylhex-1-en-3-one

Add to a solution of 1-diethylamino-6-phenylhex-2-yne (27.1 g) in concentrated sulphuric acid (7.6 cc) diluted with water (77 cc) at 70° mercuric sulphate (1.6 g), and keep the solution under nitrogen for 1 hour; cool, make basic with sodium hydroxide solution, and filter through glass wool to remove mercuric oxide. Extract the product with ether and evaporate the washed and dried ethereal solution, leaving crude 1-diethylamino-6-phenylhexan-3-one. Distil under reduced pressure with this ketoamine undergoing partial elimination of diethylamine, to obtain a mixture of the ketoamine, and 6-phenylhex-1-en-3-one (18.9 g), b.p. 96°/0.003 mm.

Infrared absorption peaks at 5.88 and 5.95 μ.

To prepare 1-diethylamino-6-m-ethoxyphenyloctan-3-one and 6-m-ethoxyphenyloct-1-en-3-one hydrate and react 1-diethylamino-6-m-ethoxyphenyloct-2-yne in the presence of mercury salts according to the manipulative procedure set forth above.

To prepare 1-diethylamino-6-m-propoxyphenylhexan-3-one and 6-m-propoxyphenylhex-1en-3-one hydrate and react 1-diethylamino-6-m-propoxyphenylhex-2-yne in the presence of mercury salts according to the manipulative procedure set forth above.

To prepare 1-diethylamino-6-m-pentoxyphenylhexan-3-one and 6-m-pentoxyphenylhex-1-en-3-one hydrate and react 1-diethylamino-6-m-propoxyphenylhex-2-yne in the presence of mercury salts according to the manipulative procedure set forth above.

To prepare 1-diethylamino-6-m-cyclopentyloxyphenylhexan-3-one and 6-m-cyclopentyloxyphenylhex-1-en-3-one hydrate and react 1-diethylamino-6-m-cyclopentyloxyphenylhex-2-yne in the presence of mercury salts according to the manipulative procedure set forth above.

To prepare 1-diethylamino-6-m-propoxyphenylheptan-3-one and 6-m-propoxyhept-1-en-3-one hydrate and react 1-diethylamino-6-m-propoxyphenylhept-2-yne in the presence of mercury salts according to the manipulative procedure set forth above.

To prepare 1-diethylamino-6-(3,5-diethoxyphenyl)-hexan-3-one and 6-(3,5-diethoxyphenyl)-hex-1-en-3-one hydrate and react 1-diethylamino-6-(3,5-diethoxyphenyl)hex-2-yne in the presence of mercury salts according to the manipulative procedure set forth above.

To prepare 1-diethylamino-6-(3-ethoxy-4-propoxyphenyl)hexan-3-one and 6-(3-ethoxy-4-propoxyphenyl)hex-1-en-3-one hydrate and react 1diethylamino-6-(3-ethoxy-4-propoxyphenyl)hex-2-yne in the presence of mercury salts according to the manipulative procedure set forth above.

These compounds are useful for preparing the novel compositions of this invention which have hormonal activity.

EXAMPLE 10

1-Diethylamino-6-m-nitrophenylhexan-3-one and 6-m-Nitrophenylhex-1-en-3-one

Hydrate 1-diethylamino-6-m-nitrophenylhex-2-yne (1.5 g) using the procedure of Example 2 with 1/20 of the quantities of reagents. Remove the solvent to obtain crude 1-diethylamino-6-m-nitrophenylhexan-3-one as a clear pale yellow liquid. Distil under reduced pressure, with considerable elimination of diethylamine, to obtain crude 6-m-nitrophenylhex-1-en-3-one (1 g) as a clear pale yellow liquid.

EXAMPLE 11

1-Diethylamino-6-m-hydroxyphenylhexan-3-one

Add mercuric sulphate (0.27 g) rapidly with swirling to a solution of 1-diethylamino-6-m-acetoxyphenylhex-2-yne (3.1 g) in 10% aqueous sulphuric acid (15 cc), and heat the resulting green solution at 75° under nitrogen for 1½ hours. After cooling, filter to remove mercuric sulphate and add solid potassium bicarbonate until the product has pH 8.8. Extract the solution with ether. Wash the other extracts with brine made alkaline to pH 8.8, and dry over anhydrous magnesium sulphate. Evaporate the ether at room temperature to obtain as residue crude 1-diethylamino-6-m-hydroxyphenylhexan-3-one as a viscous brown oil (2.4 g), showing infrared absorption at 5.85 μ indicating the presence of a keto group, together with the characteristic band of a phenolic hydroxy group and the complete absence of a band at 5.68 μ corresponding to a phenolic acetate group.

This compound is useful for preparing the novel compositions of this invention which have hormonal activity.

EXAMPLE 12

1-Diethylamino-6-m-acetoxyphenylhexan-3-one and 6-m-Acetoxyphenylhex-1-en-3-one

Acetylate the crude 1-diethylamino-6-m-hydroxyphenylhexan-3-one (2.4 g) by adding pyridine (7 cc) and acetic anhydride (3 cc) and allow the mixture to stand overnight at room temperature. Work up the mixture as in the acetylation stage described in the preparation of 5-m-acetoxyphenylpent-1-yne above, to obtain crude 1-diethylamino-6-m-acetoxyphenylhexan-3-one as a viscous brown oil (2.7 g).

Infrared absorption peaks at 5.68 μ with a shoulder at 5.85 μ and no appreciable phenolic absorption.

Distil in a Hickman still at 0.1 mm, with partial elimination of diethylamine, and collect a colorless mobile liquid, b.p. 160°–170°/0.1 mm, which is a mixture (1.8 g) of the ketoamine and 6-m-acetoxyphenylhex-1-en-3-one.

Infrared absorption peaks at 5.68, 5.88, 5.95 μ, the nature of the absorption indicating a predominance of the vinyl ketone in the mixture.

These compounds are useful for preparing the novel compositions of this invention which have hormonal activity.

EXAMPLE 13

1-Diethylamino-6-(3,4-dihydroxyphenyl)hexan-3-one

Add mercuric sulphate (0.27 g) to a swirled solution of 1-diethylamino-6-(3,4-methylenedioxyphenyl)hex-2-yne (3 g) in 10% aqueous sulphuric acid (15 cc) and heat the mixture for 90 minutes at 75° in an atmosphere of nitrogen. Filter the cooled reaction mixture and add solid potassium carbonate to pH 8.5. Extract the product with ether; wash and dry and evaporate the solvent to leave as residue crude 1-diethylamino-6-(3,4-dihydroxyphenyl)hexan-3-one.

Infrared absorption peaks at 5.85 μ.

This compound is useful for preparing the novel compositions of this invention which have hormonal activity.

EXAMPLE 14

1-Diethylamino-6-(3,4-dimethoxyphenyl)hexan-3-one and 6-(3,4-Dimethoxyphenyl)hex-1-en-3-one Add mercuric sulphate (0.45 g) to a stirred solution of 1-diethylamino-6-(3,4-dimethoxyphenyl)hex-2-yne (8.5 g) in concentrated sulphuric acid (2.5 cc) and water (25 cc) and maintain the solution at 75° for 90 minutes. Make the cooled solution basic with 10% aqueous sodium hydroxide and filter to remove mercuric oxide. Extract the product with ether and wash and dry the ethereal solution. Evaporate the solvent to obtain 1-diethylamino-6-(3,4-dimethoxyphenyl)hexan-3-one as an oily residue.

Infrared absorption peaks (liquid film) 5.85 μ. Slowly distil through a short fractionating column at 0.1 mm Hg to obtain mainly the eliminated product 6-(3,4-dimethoxyphenyl)hex-1-en-3-one.

Infrared absorption peaks (liquid film) 5.95 μ.

This compound is useful for preparing the novel compositions of this invention which have hormonal activity.

EXAMPLE 15

1-Diethylamino-6-(3,5-dimethoxyphenyl)hexan-3-one and 6-(3,5-Dimethoxyphenyl)hex-1-en-3-one Proceed exactly as described for the preparation of the 3,4-dimethoxy compound above, using 6-(3,5-dimethoxyphenyl)-1-diethylaminohex-2-yne (8.5 g.), mercuric sulphate (0.45 g), and 10% sulphuric acid (25 cc) to obtain 1-diethylamino-6-(3,5-dimethoxyphenyl)hexan-3-one and 6-(3,5-dimethoxyphenyl)hex-1-en-3-one.

EXAMPLE 16

1-Diethylamino-6-(m-methoxyphenyl)heptan-3-one and 6-(m-Methoxyphenyl)hept-1-en-3-one Dissolve 1-diethylamino-6-(m-methoxyphenyl)hept-2-yne (13.6 g) in 10% aqueous sulphuric acid (40 cc) and stir with mercuric sulphate (0.69 g) for 2 hours at 70°. Filter the cooled solution, make basic with 10% aqueous sodium hydroxide and extract with ether. Wash the ethereal solution with water and brine, and dry (Na₂SO₄). Evaporate the solvent and distil the residue to obtain 1-diethylamino-6-(m-methoxyphenyl)-heptan-3-one which has partially eliminated to 6-(m-methoxyphenyl)hept-1-en-3-one during the distillation, b.p. 145°/12 mm Hg.

Infrared absorption peaks at 5.95 μ.

This compound is useful for preparing the novel compositions of this invention which have hormonal activity.

EXAMPLE 17

1-Diethylamino-6-(m-methoxyphenyl)-5-methylhexan-3-one and
5-Methyl-6-(m-methoxyphenyl)hex-1-en-3-one Add mercuric sulphate (0.45 g) to a stirred solution of 1-diethylamino-5-methyl-6-(m-methoxyphenyl)hex-2-yne (8 g) in concentrated sulfuric acid (2.5 cc) and water (25 cc) and heat the mixture at 70° for 1½ hours. Filter the cooled solution, make basic with 10% aqueous sodium hydroxide and extract with ether. Wash and dry the ethereal solution and evaporate to leave as residue crude 1-diethylamino-6-(m-methoxyphenyl)-5-methylhexan-3-one; infrared absorption peaks at 5.85 μ. Slowly distil at 0.1 mm Hg to obtain 5-methyl-6-(m-methoxyphenyl)hex-1-en-3-one; infrared absorption peaks at 5.85 μ.

This compound is useful for preparing the novel compositions of this invention which have hormonal activity.

EXAMPLE 18

2-(6-m-Methoxyphenyl-3-oxohexyl)-2-methylcyclohexane-1,3-dione

Reflux a mixture (9 g) of 1-diethylamino-6-m-methoxyphenylhexan-3-one and 6-m-methoxyphenyl-hex-1-en-3-one with 2-methylcyclohexane-1,3-dione (4 g) in benzene (46 cc) containing pyridine (3.5 cc) for 15 hours. Wash and dry the cooled solution. Remove the solvent to obtain the triketone 2-(6-m-methoxyphenyl-3-oxohexyl)-2-methylcyclohexane-1,3-dione (8.2 g); infrared absorption peaks at 5.88, 5.85, 5.83 μ.

This compound is useful as an intermediate for preparing the novel compositions of this invention having hormonal activity.

EXAMPLE 19

2-(6-m-Methoxyphenyl-3-oxohexyl)-2-methylcyclohexane-1,3-dione

Add to the crude undistilled ketoamine 1-diethylamino-6-(m-methoxyphenyl)hexan-3-one (2.3 g), the material obtained by hydration of the acetylenic amine, 2-methylcyclohexane-1,3-dione (1 g), pyridine (1 cc) and benzene (12 cc), and reflux the mixture for 15 hours. Cool the mixture and filter off unreacted dione, add a little ether to the filtrate, and wash the ethereal solution with acid, and then water, and dry. Evaporate the solvents to obtain as residue crude 2-(6-m-methoxyphenyl-3-oxohexyl)-2-methylcyclohexane-1,3-dione (1.7 g).

This compound is useful as an intermediate for preparing the novel compositions of this invention having hormonal activity.

EXAMPLE 20

2-(6-m-Methoxyphenyl-3-oxohexyl)-2-methylcyclopentane-1,3-dione

Reflux a mixture (6 g) of 1-diethylamino-6-m-methoxyphenylhexan-3-one and 6-m-methoxyphenylhex-1-en-3-one with 2-methylcyclopentane-1,3-dione (2.8 g) in 0.12% dry methanolic potassium hydroxide solution (20 cc) for 12 hours. Remove most of the methanol under reduced pressure and add a mixture (50 cc) of equal volumes of benzene and ether; wash the solution with water, alkali and hydrochloric acid, and dry. Evaporate the solvent to obtain the adduct, the triketone 2-(6-m-methoxyphenyl-3-oxohexyl)-2-methylcyclopentane-1,3-dione (6.7 g), a viscous brown gum.

To prepare 2-(6-m-methoxyphenyl-3-oxohexyl)-2-n-butylcyclopentane-1,3-dione, treat a mixture of 1-diethylamino-6-m-methoxyphenylhexan-3-one and 6-m-methoxyphenylhex-1-en-3-one with 2-butylcyclopentane-1,3-dione and dry methanolic potassium hydroxide solution according to the manipulative procedure described above.

To prepare 2-(6-m-methoxyphenyl-3-oxohexyl)-2-hydroxypropylcyclopentane-1,3-dione, treat a mixture of 1-diethylamino-6-m-methoxyphenylhexan-3-one and 6-m-methoxyphenylhex-1-en-3-one with 2-hydroxypropylcyclopentane-1,3-dione and dry methanolic potassium hydroxide solution according to the manipulative procedure described above.

To prepare 2-(6-m-ethoxyphenyl-3-oxohexyl)-2-ethylcyclopentane-1,3-dione, treat a mixture of 1-diethylamino-6-m-ethoxyphenylhexan-3-one and 6-m-ethoxyphenylhex-1-en-3-one with 2-ethylcyclopentane-1,3-dione and dry methanolic potassium hydroxide solution according to the manipulative procedure described above.

To prepare 2-(6-m-propoxyphenyl-3-oxohexyl)-2-phenethylcyclopentane 1,3-dione, treat a mixture of 1-diethylamino-6-m-propoxyphenylhexan-3-one and 6-m-propoxyphenylhex-1-en-3-one with 2-phenethylcyclopentane-1,3-dione and dry methanolic potassium hydroxide solution according to the manipulative procedure described above.

To prepare 2-(6-m-pentyloxyphenyl-3-oxohexyl)-2-isobutylcyclopentane-1,3-dione, treat a mixture of 1-diethylamino-6-m-pentyloxyphenylhexan-3-one and 6-m-pentyloxyphenylhex-1-en-3-one with 2-isobutylcyclopentane-1,3-dione and dry methanolic potassium hyroxide solution according to the manipulative procedure described above.

To prepare 2-(6-m-cyclopentyloxyphenyl-3-oxohexyl)-2-hydroxypropylcyclopentane-1,3-dione, treat a mixture of 1-diethylamino-6-m-cyclopentyloxyphenylhexan-3-one and 6-m-cyclopentyloxyphenylhex-1-en-3-one with 2-hydroxypropylcyclopentane-1,3-dione and dry methanolic potassium hydroxide solution according to the manipulative procedure described above.

To prepare 2-(6 -m-hydroxyphenyl-3-oxohexyl)-2-phenethylcyclopentane-1,3-dione, treat a mixture of 1-diethylamino-6-m-hydroxyphenylhexan-3-one and 6-m-hydroxyphenylhex-1-en-3-one with 2-phenethylcyclopentane-1,3-dione and dry methanolic potassium hydroxide solution according to the manipulative procedure described above.

To prepared 2-[6-(3,4-dimethoxyphenyl)-3-oxohexyl]-2-diethylaminoethylcyclopentane-1,3-dione, treat a mixture of 1-diethylamino-6-(3,4-dimethoxyphenyl)-hexan-3-one and 6-(3,4-dimethoxyphenyl)hex-1-en-3-one with 2-diethylaminoethylcyclopentane-1,3-dione and dry methanolic potassium hydroxide solution according to the manipulative procedure described above.

To prepare 2-[6-(3,5-dimethoxyphenyl)-3-oxoheptyl]-2-dimethylaminopropylcyclopentane-1,3-dione, treat a mixture of 1-diethylamino-6-(3,5-dimethoxyphenyl)heptan-3-one and 6-(3,5-dimethoxyphenyl)-hept-1-en-3-one with 2-dimethylaminopropylcyclopentane-1,3-dione and dry methanolic potassium hydroxide solution according to the manipulative procedure described above.

To prepare 2-[6-(3,5-diethoxyphenyl)-3-oxooctyl]-2-n-butylcyclopentane-1,3-dione, treat a mixture of 1-diethylamino-6-(3,5-diethoxyphenyl)octan-3-one and 6-(3,5-diethoxyphenyl)oct-1-en-3-one with 2-butylcyclopentane-1,3-dione and dry methanolic potassium hydroxide solution according to the manipulative procedure described above.

To prepare 2-[6-(3-methoxy-4-ethoxyphenyl)-3-oxohexyl]-2-n-propylcyclopentane-1,3-dione, treat a mixture of 1-diethylamino-6-(3-methoxy-4-ethoxyphenyl)hexan-3-one and 6-(3-methoxy-4-ethoxyphenyl)hex-1-en-3-one with 2-propylcyclopentane-1,3-dione and dry methanolic potassium hydroxide solution according to the manipulative procedure described above.

To prepare 2-(6-m-methoxyphenyl-3-oxohexyl)-2-n-propylcyclopentane-1,3-dione, treat a mixture of 1-diethylamino-6-m-methoxyphenylhexan-3-one and 6-m-methoxyphenylhex-1-en-3-one with 2-propylcyclopentane-1,3-dione and dry methanolic potassium hydroxide solution according to the manipulative procedure described above.

To prepare 2-(6-m-acetoxyphenyl-3-oxohexyl)-2-ethylcyclopentane-1,3-dione, treat a mixture of 1-diethylamino-6-m-acetoxyphenylhexan-3-one and 6-m-acetoxyphenylhex-1-en-3-one with 2-ethylcyclopentane-1,3-dione and dry methanolic potassium hydroxide solution according to the manipulative procedure described above.

To prepare 2-(6-m-hydroxyphenyl-3-oxohexyl)-2-ethylcyclopentane-1,3-dione, treat a mixture of 1-diethylamino-6-m-hydroxyphenylhexan-3-one and 6-m-hydroxyphenylhex-1-en-3-one with 2-ethylcyclopentane-1,3-dione and dry methanolic potassium hydroxide solution according to the manipulative procedure described above.

EXAMPLE 21

2-(6-m-Methoxyphenyl-3-oxohexyl)-2-methylcyclopentane-1,3-dione

Add the crude methiodide of 1-diethylamino-6-m-methoxyphenylhexan-3-one (2.5 g) in methanol (10 cc) ice-cold to a solution obtained by adding 2-methylcyclopentane-1,3-dione (0.5 g) to an ice-cold solution of sodium (0.21 g) in methanol (10 cc). Allow the reaction mixture to warm to room temperature and leave for 16 hours, after which add N hydrochloric acid (10 cc) and saturated brine (100 cc), and ether-extract the solution. Evaporate the washed and dried extracts to obtain the crude adduct 2-(6-m-methoxyphenyl-3-oxohexyl)-2-methylcyclopentane-1,3-dione as a gum.

This compound is useful as an intermediate for preparing the novel compositions of this invention having hormonal activity.

EXAMPLE 22

2-(6-m-Methoxyphenyl-3-oxohexyl)-2-methylcyclopentane-1,3-dione

Reflux 6-m-methoxyphenylhex-1-en-3-one, containing a small amount of 1-diethylamino-6-m-methoxyphenylhexan-3-one (6 g, the material produced by the slow distillation of the latter substance), with 2-methylcyclopentane-1,3-dione (3.5 g) in 0.12% anhydrous methanol in potassium hydroxide (10 cc) for 10 hours. Work up the reaction mixture as described for the preparation of the compound as titled above, to obtain the crude triketone 2-(6-m-methoxyphenyl-3-oxohexyl)-2-methylcyclopentane-1,3-dione (8 g). Distil a small portion of this at 0.02 mm for analysis.

$C_{19}H_{24}O_4$ Calculated: C, 72.1%; H, 7.65%. Found: C, 72.3%; H, 7.45%.

This compound is useful as an intermediate for preparing the novel compositions of this invention having hormonal activity.

EXAMPLE 23

2-(6-m-Methoxyphenyl-3-oxohexyl)-2-methylcyclopentane-1,3-dione

Add sodium (0.05 g) to a 0.12% methanolic potassium hydroxide solution (15 cc). To this solution add 1-bromo-6-(m-methoxyphenyl)-hexan-3-one (0.9 g) in methanol (5 cc) and 2-methylcyclopentane-1,3-dione (0.4 g), and reflux the mixture for 6 hours. After working up as in the preparation of the title compound in a previous example, obtain the crude Michael adduct 2-(6-m-methoxyphenyl-3-oxohexyl)-2-methylcyclopentane-1,3-dione as a yellow gum.

This compound is useful as an intermediate for preparing the novel compositions of this invention having hormonal activity.

EXAMPLE 24

2-(6-m-Methoxyphenyl-3-oxohexyl)-2-ethylcyclohexane-1,3-dione

Reflux 2-ethylcyclohexane-1,3-dione (30.6 g), pyridine (20 cc), benzene (372 cc) and a mixture of 1-diethylamino-6-m-methoxyphenylhexan-3-one and 6-m-methoxyphenylhex-1-en-3-one (40.3 g, produced by the distillation of the former substance) for 15 hours. Wash the cooled reaction mixture with water, 10% aqueous sulfuric acid, water, 10% aqueous sodium carbonate, water and brine, and filter. Evaporate the solvent to leave as residue 2-(6-m-methoxyphenyl-3-oxohexyl)-2-ethylcyclohexane-1,3-dione, 38.1 g, 56.2%.

This compound is useful as an intermediate for the preparation of the novel compositions of this invention which have hormonal activity.

EXAMPLE 25

2-(6-m-Methoxyphenyl-3-oxohexyl)-2-ethylcyclopentane-1,3-dione

Reflux a mixture (5.25 g) of 1-diethylamino-6-m-methoxyphenylhexan-3-one and 6-m-methoxyphenylhex-1-en-3-one with 2-ethylcyclopentane-1,3-dione (3.3 g) in dry 0.12% methanolic solution of potassium hydroxide for 18 hours. Filter the resulting solution, evaporate to dryness and dissolve the residue in ether. Wash the ether solution with alkali, hydrochloric acid, and water, dry and evaporate to obtain as residue the triketone 2-(6-m-methoxyphenyl-3-oxohexyl)-2-ethylcyclopentane-1,3-dione (7.1 g) as a gum.

This compound is useful as an intermediate for the preparation of the novel compositions of this invention which have hormonal activity.

EXAMPLE 26

2-Isopropyl-2-(6-m-methoxyphenyl-3-oxohexyl)cyclopentane-1,3-dione

Condense a mixture (6 g) of 1-diethylamino-6-(m-methoxyphenyl)hexan-3-one and 6-(m-methoxyphenyl)hex-1-en-3-one with 2-isopropylcyclopentane-1,3-dione (3 g) using a procedure similar to that described for the condensation of the 2-ethyl compound. Obtain the corresponding triketone, 2-isopropyl-2-(6-m-methoxyphenyl-3-oxohexyl)cyclopentane-1,3-dione (7.2 g) as an uncrystallizable gum.

This compound is useful as an intermediate for the preparation of the novel compositions of this invention which have hormonal activity.

EXAMPLE 27

2-(6-m-Methoxyphenyl-3-oxoheptyl)-2-ethylcyclopentane-1,3-dione

Reflux a mixture of 6-(m-methoxyphenyl)hept-1-en-3-one and 1-diethylamino-6-(m-methoxyphenyl)heptan-3-one (10 g, obtained by slow distillation of the latter substance) with 2-ethylcyclopentane-1,3-dione (7 g) in 0.12% methanolic potassium hydroxide solution (40 cc) for 15 hours. Remove most of the methanol under reduced pressure and add a mixture of equal volumes of ether and benzene (50 cc). Wash the solution with 5% aqueous sodium hydroxide, water, 10% hydrochloric acid, and brine, and dry. Evaporate the solvent to leave as residue the triketone adduct 2-(6-m-methoxyphenyl-3-oxoheptyl)-2-ethylcyclopentane-1,3-dione (14 g); infrared absorption peak at 5.80 μ.

This compound is useful as an intermediate for the preparation of the novel compositions of this invention which have hormonal activity.

EXAMPLE 28

2-Ethyl-2-(6-m-methoxyphenyl-5-methyl-3-oxohexyl)-cyclopentane-1,3-dione

Add a mixture of 1-diethylamino-6-(m-methoxyphenyl)-5-methylhexan-3-one and 5-methyl-6-(m-methoxyphenyl)hex-1-en-3-one (6 g, prepared by slow distillation of the former substance) to 2-ethylcyclopentane-1,3-dione (3.5 g) in 0.12% methanolic potassium hydroxide (10 cc) and heat the mixture under reflux for 16 hours. Remove most of the solvent under reduced pressure and add ether (25 cc) and benzene (25 cc) to the residue. Wash the solution with 5% aqueous sodium hydroxide, water, dilute hydrochloric acid, and brine, and dry. Evaporate the solvent to obtain a viscous brown gum, which is the triketone 2-ethyl-2-(6-m-methoxyphenyl-5-methyl-3-oxohexyl)cyclopentane-1,3-dione.

This compound is useful as an intermediate for preparing the novel compositions of this invention having a hormonal activity.

EXAMPLE 29

2-(6-Phenyl-3-oxohexyl)-2-methylcyclohexane-1,3-dione

Reflux the mixture of 1-diethylamino-6-phenylhexan-3-one and 6-phenylhex-1-en-3-one (19 g) with 2-methylcyclohexane-1,3-dione (8.4 g) in benzene (97 cc) containing pyridine (7.4 cc) for 15 hours. Wash and dry the cooled solution. Remove the solvent to obtain the crude triketone 2-(6-phenyl-3-oxohexyl)-2-methylcyclohexane-1,3-dione.

This compound is useful as an intermediate for preparing the novel compositions of this invention having hormonal activity.

EXAMPLE 30

2-(6-m-Nitrophenyl-3-oxohexyl)-2-methylcyclopentane-1,3-dione 6-m-Nitrophenylhex-1-en-3-one (1.0 g, containing a small amount of 1-diethylamino-6-m-nitrophenylhexan-3-one) in anhydrous 0.1% methanolic potassium hydroxide (10 cc) with 2-methylcyclopentane-1,3-dione (1.5 g) for 12 hours. Cool the solution, pour into water and ether extract. Wash the extracts with sodium bicarbonate solution, dry and evaporate to obtain a gum (1.3 g). Crystallize by adding ethanol, recrystallize from ethanaol to obtain 2-(6-m-nitrophenyl-3-oxohexyl)-2-methylcyclopentane-1,3-dione, m.p. 81°-83°C; infrared absorption peaks at 5.70, 5.80, 5.83, 6.54, 7.33 $\mu$ (the first three peaks representing carbonyl groups and the others a nitro group).

This compound is useful as an intermediate for preparing the novel compositions of this invention having hormonal activity.

EXAMPLE 31

2-(6-m-Hydroxyphenyl-3-oxohexyl)-2-methylcyclopentane-1,3-dione

Reflux 1-diethylamino-6-m-hydroxyphenylhexan-3-one (0.72 g) with 2-methylcyclopentane-1,3-dione (0.70 g) in 0.12% methanolic potassium hydroxide (5 cc) for 18 hours. Remove the solvent under reduced pressure. Add chloroform (50 cc) and wash the solution in turn with dilute sulfuric acid, saturated aqueous potassium bicarbonate, and brine, dry and evaporate the solvent. The product, an amber gum, is the adduct 2-(6-m-hydroxyphenyl-3-oxohexyl)-2-methylcyclopentane-1,3-dione. Infrared absorption peaks at 2.94, 5.71, 5.83 and 5.87 $\mu$.

This compound is useful as an intermediate for preparing the novel compositions of this invention having hormonal activity.

EXAMPLE 32

2-(6-m-Acetoxyphenyl-3-oxohexyl)-2-methylcyclopentane-1,3-dione

Reflux a mixture of 6-(m-acetoxyphenyl)-1-diethylaminohexan-3-one and 6-(m-acetoxyphenyl)hex-1-en-3-one (1 g), with 2-methylcyclopentane-1,3-dione (1.5 g) in 0.12% methanolic potassium hydroxide (6 cc) for 18 hours. Remove methanol (2 cc) under reduced pressure and add chloroform (60 cc). Wash the solution in turn with dilute sulfuric acid (25 cc), saturated potassium bicarbonate solution, and brine; dry and evaporate the solvent. The product (0.8 g) is the adduct 2-(6-m-acetoxyphenyl-3-oxohexyl)-2-methylcyclopentane-1,3-dione in admixture with some of the corresponding free phenol; infrared absorption: 2.86 to 3.08 (broad low-intensity band), 5.71, 5.81, 5.85, and 8.26 $\mu$.

This compound is useful as an intermediate for preparing the novel compositions of this invention having hormonal activity.

EXAMPLE 33

2-(6-m-Hydroxyphenyl-3-oxohexyl)-2-n-propylcyclopentane-1,3-dione

Heat together 2-n-propylcyclopentane-1,3-dione (13 g), 1-diethylamino-6-m-hydroxyphenylhexan-3-one and 0.12% methanolic potassium hydroxide solution (38 cc) under gentle reflux for 12 hours. Isolate the product to obtain the Michael adduct, 2-(6-m-hydroxyphenyl-3-oxohexyl)-2-n-propylcyclopentane-1,3-dione as a brown gum (7.18 g).

This compound is useful as an intermediate for preparing the novel compositions of this invention having hormonal activity.

EXAMPLE 34

2-[6-(3,4-Dimethoxyphenyl)-3-oxohexyl]-2-ethylcyclopentane-1,3-dione

Reflux 6-(3,4-dimethoxyphenyl)hex-1-en-3-one, containing a small amount of 6-(3,4-dimethoxyphenyl)-1-diethylaminohexan-3-one (6 g, produced by slow distillation of the latter substance) with 2-ethylcyclopentane-1,3-dione (3.5 g) in 0.12% anhydrous methanolic potassium hydroxide (10 cc) for 10 hours. Remove most of the methanol under reduced pressure, add benzene (25 cc) and ether (25 cc) and wash the solution with water, dilute aqueous potassium hydroxide, dilute hydrochloric acid and water. Dry and evaporate the solvent to give the triketone adduct 2-[6-(3,4-dimethoxyphenyl)-3-oxohexyl]-2-ethylcyclopentane-1,3-dione; infrared absorption (gum) 5.80, 6.25 $\mu$ (split peak).

This compound is useful as an intermediate for preparing the novel compositions of this invention having hormonal activity.

EXAMPLE 35

2-[6-(3,5-Dimethoxyphenyl)-3-oxohexyl]-2-ethylcyclopentane-1,3-dione

Reflux 6-(3,5-dimethoxyphenyl)hex-1-en-3-one, containing a small amount of 6-(3,5-dimethoxyphenyl)-1-diethylaminohexan-3-one (6 g, produced by slow distillation of the latter substance) with 2-ethylcyclopentane-1,3-dione (3.5 g) in 0.12% anhydrous methanolic potassium hyroxide (10 cc) for 10 hours. Work up the reaction mixture as for the preparation of 2-(6-m-acetoxyphenyl-3-oxohexyl)-2-methylcyclopentane-1,3-dione to obtain 2-[6-(3,5-dimethoxyphenyl)-3-oxohexyl]-2-ethylcyclopentane-1,3-dione as a viscous gum; infrared absorption peaks at 5.80, 6.25 $\mu$ (split peak).

This compound is useful as an intermediate for preparing the novel compositions of this invention having hormonal activity.

EXAMPLE 36

Diethyl 2-(6-m-methoxyphenyl-3-oxohexyl)-2-methyl-3-oxoadipate

Stir a mixture of diethyl 2-methyl-3-oxoadipate (2.3 g, b.p. 111°–112°C/0.2 mm), prepared from 2-methylacetoacetic ester and ethoxycarbonylpropionyl chloride by the method of Cardwell, *J. Chem. Soc.*, 1949, 715, and the methiodide of 1-diethylamino-6-m-methoxyphenylhexan-3-one (4.6 g) in benzene (20 cc) in an ice bath and add a solution of potassium (0.4 g) in ethanol (10 cc) dropwise over one hour. After stirring for a further 4 hours add ether (50 cc) and evaporate the washed and dried ether extracts. Heat the residue at 160°C and 0.2 mm pressure to remove unchanged starting materials. The residual gum is diethyl 2-(6-m-methoxyphenyl-3-oxohexyl)-2-methyl-3-oxoadipate (2.7 g); infrared absorption peaks at 5.78, 5.88, 6.25, 12.82, 14.49 $\mu$.

This compound is useful as an intermediate for preparing the novel compositions of this invention which have hormonal activity.

EXAMPLE 37

13$\beta$-Methyl-3-methoxy-D-homogona-1,3,5(10),8,14-pentaen-17a-one

Reflux the dicyclic triketone 2-(6-m-methoxyphenyl-3-oxohexyl)-2-methylcyclohexane-1,3-dione (2 g) for 2 hours in benzene (35 cc) containing anhydrous toluene-p-sulfonic acid (1 g) using a Dean-Stark trap to remove the water formed. The worked-up product is a solid which one recrystallizes from light petroleum (b.p. 60°–80°) and from methanol to give the diene 13$\beta$-methyl-3-methoxy-D-homogona-1,3,5(10),8,14-pentaen-17a-one (0.5 g), m.p. 135°–137°C; ultraviolet absorption peak at 310 m$\mu$ ($\epsilon$30,000).

$C_{20}H_{22}O_2$ Calculated: C, 81.6%; H, 7.5%. Found: C, 81.45%; H, 7.7%.

This compound has estrogenic activity, lowers the blood lipid level, and is useful as an intermediate for preparing the hormonal compounds of this invention.

EXAMPLE 38

13$\beta$-Methyl-3-methoxygona-1,3,5(10),8,14-pentaen-17-one

Dissolve the triketone 2-(6-m-methoxyphenyl-3-oxohexyl)-2-methylcyclopentane-1,3-dione (6.7 g), in dry benzene (100 cc) containing anhydrous toluene-p-sulfonic acid (2.4 g). Reflux the mixture using a Dean-Stark water separator until the equivalent of two molecular proportions of water (0.99 cc) is collected (30 minutes), indicating a double cyclodehydration. Cool and wash to remove acid, and dry. Evaporate the dried solution to obtain a red gum. Distil the gum under reduced pressure (bath temperature 210°, 0.5 mm). Recrystallize the solidified distillate from methanol, giving 13$\beta$-methyl-3-methoxygona-1,3,5(10),8,14-pentaen-17-one (3.9 g), m.p. 115°–116°; ultraviolet absorption peak at 313 m$\mu$ ($\epsilon$35,100). The light absorption is in agreement with the structure assigned.

$C_{19}H_{20}O_2$ Calculated: C, 81.4%; H, 7.2%. Found: C, 81.1%; H, 7.0%.

This compound has estrogenic activity, lowers the blood lipid level, and is useful as an intermediate for preparing the hormonal compounds of this invention.

EXAMPLE 39

13$\beta$-Methyl-3-methoxygona-1,3,5(10),8,14-pentaen-17-one

Add the crude methiodide of 1-diethylamino-6-m-methoxyphenylhexan-3-one (2.5 g) in methanol (10 cc) ice-cold to a solution obtained by adding 2-methylcyclopentane-1,3-dione (0.5 g) to an ice-cold solution of sodium (0.21 g) in methanol (10 cc). Allow the reaction mixture to warm to room temperature and leave for 16 hours, after which add N hydrochloric acid (10 cc) and saturated brine (100 cc), etherextracting the solution. Evaporate the washed and dried extracts to obtain crude 2-(6-m-methoxyphenyl-3-oxohexyl)-2-methylcyclopentane-1,3-dione as a gum; dissolve in benzene (25 cc) containing toluene-p-sulfonic acid (0.4 g) and reflux the mixture for 1 hour. Cool, add ether (25 cc), and wash, dry, and evaporate the solution. Take up the resulting gum in benzene (5 cc) and adsorb on a column of Fuller's earth (100 g). Elute with a mixture of benzene and light petroleum to obtain a series of fractions, one of which crystallizes (0.04 g). Boil this fraction with methanol and decant the solution from insoluble oil which forms. Reduce the solution in bulk by evaporation, depositing crystals on cooling; recrystallize from methanol to obtain 13$\beta$-methyl-3-methoxygona-1,3,5(10),8,14 -pentaen-17-one, m.p. 111°–113°C; ultraviolet absorption peak at 312 m$\mu$ ($\epsilon$34,800).

This compound has estrogenic activity, lowers the blood lipid level, and is useful as an intermediate for preparing the hormonal compounds of this invention.

EXAMPLE 40

13$\beta$-Methyl-3-methoxygona-1,3,5(10),8,14-pentaen-17-one

To 2-(6-m-methoxyphenyl-3-oxohexyl)-2-methylcyclopentane-1,3-dione (3 g) in benzene (100 cc) add polyphosphoric acid (from orthophosphoric acid, 15 g. and phosphorus pentoxide, 6 g.) and heat the mixture at 90° for 4 minutes under such reduced pressure as the need to control frothing will allow. Cool, add water, and extract the mixture with ether and ethyl acetate; isolate the product from the resulting solution to obtain the colorless crystalline 13$\beta$-methyl-3-methoxygona-1,3,5(10),8,14-pentaen-17-one (2 g), b.p. 115°–116°; ultraviolet absorption peak at 313 m$\mu$ ($\epsilon$35,100).

To prepare 13$\beta$-(3-hydroxypropyl)-3-methoxygona-1,3,5(10),8,14-pentaen-17-one treat 2-(6-m-methoxyphenyl-3-oxohexyl)-2-(3-hydroxypropyl)cyclopentane-1,3-dione with polyphosphoric acid according to the manipulative procedure described above.

To prepare 13$\beta$-phenethyl-3-propoxygona-1,3,5(10),8,14-pentaen-17-one treat 2-(6-m-propoxyphenyl-3-oxohexyl)-2-phenethylcyclopentane-1,3-dione with polyphosphoric acid according to the manipulative procedure described above.

To prepare 13$\beta$-isobutyl-3-pentyloxygona-1,3,5(10),8,14-pentaen-17-one treat 2-(6-m-pentyloxyphenyl-3-oxohexyl)-2-isobutylcyclopentane-1,3-dione with polyphosphoric acid according to the manipulative procedure described above.

To prepare 13$\beta$-(3-hydroxypropyl)-3-cyclopentyloxygona-1,3,5(10),8,14-pentaen-17-one treat 2-(6-m- cyclopentyloxyphenyl-3-oxohexyl)-2-(3-hydroxypropyl)cyclopentane-1,3-dione with polyphosphoric acid according to the manipulative procedure described above.

To prepare 13β-phenethyl-3-hydroxygona-1,3,5(10),8,14-pentaen-17-one treat 2-(6-m-hydroxyphenyl-3-oxohexyl)-2-phenethylcyclopentane-1,3-dione with polyphosphoric acid according to the manipulative procedure described above.

To prepare 13β-(2-diethylaminoethyl)-2,3-dimethoxygona-1,3,5(10),8,14-pentaen-17-one treat 2-[6-(3,4-dimethoxyphenyl)-3-oxohexyl]-2-(2-diethylaminoethyl)cyclopentane-1,3-dione with polyphosphoric acid according to the manipulative procedure described above.

To prepare 13β-(3-dimethylaminopropyl)-1,3-dimethoxy-6-methylgona-1,3,5(10),8,14-pentaen-17-one treat 2-[6-(3,5-dimethoxyphenyl)-3-oxoheptyl]-2-(3-dimethylaminopropyl)cyclopentane-1,3-dione with polyphosphoric acid according to the manipulative procedure described above.

To prepare 13β-butyl-1,3-diethoxy-6-ethylgona-1,3,5(10),8,14-pentaen-17-one treat 2-[6-(3,5-diethoxyphenyl)-3-oxooctyl]-2-butylcyclopentane-1,3-dione with polyphosphoric acid according to the manipulative procedure described above.

To prepare 13β-propyl-2-ethoxy-3-methoxygona-1,3,5(10),8,14-pentaen-17-one treat 2-[6-(3-methoxy-4-ethoxyphenyl)-3-oxohexyl]-2-propylcyclopentane-1,3-dione with polyphosphoric acid according to the manipulative procedure described above.

To prepare 13β,6-dimethyl-1,3-dimethoxygona-1,3,5(10),8,14-pentaen-17-one treat 2-[6-(3,5-dimethoxyphenyl-3-oxoheptyl]-2-methylcyclopentane-1,3-dione with polyphosphoric acid according to the manipulative procedure described above.

These compounds have estrogenic activity, lower the blood lipid level, and are use useful as intermediates in the preparation of the hormonal compounds of the invention.

EXAMPLE 41

13β-Methyl-3-methoxygona-1,3,5(10),8,14-pentaen-17-one

Heat the tricyclic diketone 5,6,7,8-tetrahydro-4-m-methoxyphenethyl-8-methylindane-1,5-dione (0.25 g), under nitrogen at 60° with a mixture of orthophosphoric acid (5 cc, S.G. 1.8) and phosphorus pentoxide (3.25 g) for 20 minutes. Work up by means of ether to obtain a partially crystalline product which one takes up in benzene (10 cc) and filters. Recrystallize the residue to obtain the diene 13β-methyl-3-methoxygona-1,3,5(10),8,14-pentaen-17-one (0.6 g), m.p. 110°–112°C; ultraviolet absorption peaks at 310 mμ (ε37,200); infrared absorption peak at 5.78 μ.

This compound has estrogenic activity, lowers the blood lipid level, and is useful as an intermediate for preparing the hormonal compounds of this invention.

EXAMPLE 42

13β-Ethyl-3-methoxy-D-homogona-1,3,5(10),8,14-pentaen-17a-one

Add 2-(6-m-methoxyphenyl-3-oxohexyl)-2-ethylcyclohexane-1,3-dione (32.8 g) in benzene (400 cc) to polyphosphoric acid (150 g) in an atmosphere of nitrogen and stir the mixture at 60° for 3 hours. Add water, separate the benzene layer and wash with water until neutral. Dry the solution, remove the solvent, and recrystallize the residue from ethanol to obtain 13β-ethyl-3-methoxy-D-homogona-1,3,5(10),8,14-pentaen-17a-one, m.p. 90°–92°; ultraviolet absorption peak at 311 mμ (ε28,500).

This compound has estrogenic activity, lowers the blood lipid level, and is useful as an intermediate for preparing the hormonal compounds of this invention.

EXAMPLE 43

13β-Ethyl-3-methoxygona-1,3,5(10),8,14-pentaen-17-one

Reflux the triketone 2-ethyl-2-(6-m-methoxyphenyl-3-oxohexyl)cyclopentane-1,3-dione (7.1 g), in benzene (150 cc) and toluene-p-sulfonic acid (2 g) until the theoretical amount of water (0.72 cc) for double cyclodehydration has been collected in a Dean-Stark separator. Wash the cooled reaction mixture after removal of solvent under reduced pressure, b.p. ca. 220°/0.01 mm, to obtain an almost colorless glass (5.7 g). Crystallize the glass from methanol containing a little ethyl acetate to obtain pure 13β-ethyl-3-methoxygona-1,3,5(10),8,14-pentaen-17-one (3.7 g), m.p. 77°–80°; ultraviolet absorption peak at 311 mμ (ε28,000).

$C_{20}H_{22}O_2$ Calculated: C, 81.6%; H, 7.5%. Found: C, 81.3%; H, 6.3%.

This compound has estrogenic activity, lowers the blood lipid level, and is useful as an intermediate for preparing the hormonal compounds of this invention.

EXAMPLE 44

13β-Propyl-3-methoxygona-1,3,5(10),8,14-pentaen-17-one

Condense 2-propylcyclopentane-1,3-dione (13.1 g) in 0.12% methanolic potassium hydroxide solution (90 cc) with 6-m-methoxyphenyl-hex-1-en-3-one (19.0 g), to obtain crude 2-n-propyl-2-(6-m-methoxyphenyl-3-oxohexyl)cyclopentane-1,3-dione (25.5 g). Submit this Michael condensation product (23.4 g) to double cyclodehydration by heating with toluene-p-sulfonic acid, and distil the product at 200°/10⁻⁴ mm; crystallize the distillate from ethanol to obtain the tetracyclic diene ketone 13β-propyl-3-methoxygona-1,3,5(10),8,14-pentaen-17-one, m.p. 82°–84°; ultraviolet absorption peak at 310 mμ (ε24,700).

This compound has estrogenic activity, lowers the blood lipid level, and is useful as an intermediate for preparing the hormonal compounds of this invention.

EXAMPLE 45

13β-Isopropyl-3-methoxygona-1,3,5(10),8,14-pentaen-17-one

Reflux the triketone 2-isopropyl-2-(6-m-methoxyphenyl-3-oxohexyl)cyclopentane-1,3-dione (7.2 g) in benzene (150 cc) and toluene-p-sulfonic acid (2 g) until the theoretical amount of water (0.72 cc) for double cyclodehydration has been collected in a Dean-Stark trap. Wash the cooled reaction mixture to remove acid and dry. Remove the solvent to obtain a gum. Distil the gum to obtain a glass (5 g), which one crystallizes from methanol to obtain pure 13β-isopropyl-3-methoxygona-1,3,5(10),8,14-pentaen-17-one (4.5g), m.p. 112°–113°.

$C_{21}H_{24}O_2$ Calculated: C, 81.8%; H, 7.8%. Found: C, 81.8%; H, 7.6%.

This compound has estrogenic activity, lowers the blood lipid level, and is useful as an intermediate for preparing the hormonal compounds of this invention.

EXAMPLE 46

13β-Butyl-3-methoxygona-1,3,5(10),8,14-pentaen-17-one

Condense n-butylcyclopentane-1,3-dione (2.8 g) in 0.12% methanolic potassium hydroxide solution (8 cc) with 6-m-methoxyphenylhex-1-en-3-one (5 g) by heating the mixture at 80° for 10 hours. Evaporate the solvent under reduced pressure and heat the residue with toluene-p-sulfonic acid (2 g) in benzene (50 cc) for 45 minutes using a Dean-Stark trap to effect double cyclodehydration. Add ether to the cooled reaction mixture, and evaporate the washed and dried ether solution; recrystallize the residue from ethanol to obtain 13β-butyl-3-methoxygona-1,3,5(10),8,14-pentaen-17-one (1.9 g), m.p. 53°–55°; ultraviolet absorption peak at 312 mμ ($\epsilon$29,200).

This compound has estrogenic activity, lowers the blood lipid level, and is useful as an intermediate for preparing the hormonal compounds of this invention.

EXAMPLE 47

13β-Isobutyl-3-methoxygona-1,3,5(10),8,14-pentaen-17-one

Reflux a mixture of crude 2-(6-m-methoxyphenyl-3-oxohexyl)-2-isobutyl-1,3-cyclopentanedione (154.9 g) and anhydrous p-toluene-sulfonic acid (177 g) in 5.2 liters of dry benzene for 3 hours using a Dean-Stark water separator. After cooling, filter the solution, wash, dry, and concentrate to ⅓ of its volume. Then filter through charcoal (Carco, 310 g). Distil the filtrate to obtain a viscous oil, b.p. 203° (bath temperature), 0.01 mm. Recrystallize from methanol-acetone to get 13β-isobutyl-3-methoxygona-1,3,5(10),8,14-pentaen-17-one, m.p. 57°–60°; ultraviolet absorption peak at 312 mμ ($\epsilon$25,200).

$C_{22}H_{26}O_2$ Calculated: C, 81.9%; H, 8.1%. Found: C, 81.6%; H, 8.1%.

This compound has estrogenic activity, lowers the blood lipid levels, and is useful as an intermediate for preparing the hormonal compounds of this invention.

EXAMPLE 48

13β-Cetyl-3-methoxygona-1,3,5(10),8,14-pentaen-17-one

Reflux a mixture of 2-cetylcyclopentane-1,3-dione (10.1 g), 6-m-methoxyphenylhex-1-en-3-one (6.0 g) and 0.02% methanolic potassium hydroxide solution (120 cc) for 26 hours and then cool. Dissolve the residue obtained after removal of solvent under reduced pressure in a mixture of benzene (50 cc) and ether (50 cc), and wash the solution in turn with sodium carbonate solution, 10% aqueous sulfuric acid and water. Remove the solvent by evaporation under reduced pressure to obtain as residue crude 2-cetyl-2-(6-m-methoxyphenyl-3-oxohexyl)-1,3-cyclopentanedione (11.4 g).

Add a solution of this Michael condensate in dry benzene (80 cc) to a mixture of anhydrous toluene-p-sulfonic acid (2.4 g) and dry benzene (80 cc) and reflux the mixture for one hour, using a Dean-Stark water separator, until the equivalent of 2 moles of water (0.75 cc) has been collected. Wash the cooled solution, dry, and remove the solvent, leaving a purple oil (10.2 g) which one then distils at about 220°/0.001 mm. Recrystallize the solidified distillate from acetonitrile, to obtain 13β-cetyl-3-methoxygona-1,3,5(10),8,14-pentaen-17-one, m.p. 55°–56°C; ultraviolet absorption peak at 316 mμ ($\epsilon$24,000).

$C_{34}H_{50}O_2$ Calculated: C, 83.2%; H, 10.3%. Found: C 83.3%; H, 10.3%.

This compound has estrogenic activity, lowers the blood lipid level, and is useful as an intermediate for preparing the hormonal compounds of this invention.

EXAMPLE 49

13β-Ethyl-3-methoxy-6-methylgona-1,3,5(10)8,14-pentaen-17-one

Reflux 2-(6-m-methoxyphenyl-3-oxoheptyl)-2-ethyl-cyclopentane-1,3-dione (14 g) with anhydrous toluene-p-sulfonic acid (4 g) in benzene (50 cc) with continuous water separation for 20 minutes. Wash the cooled solution with water, dry, and evaporate the solvent. Distil the residual red gum to obtain 13β-ethyl-3-methoxy-6-methylgona-1,3,5(10),8,14-pentaen-17-one as a gum; ultraviolet absorption peak at 315 mμ ($\epsilon$21,000); infrared absorption peak at 5.75 μ.

This compound has estrogenic activity, lowers the blood lipid level, and is useful as an intermediate for preparing the hormonal compounds of this invention.

EXAMPLE 50

13β-Ethyl-3-methoxy-7-methylgona-1,3,5(10),8,14-pentaen-17-one

Dissolve the crude triketone 2-ethyl-2-(6-m-methoxyphenyl-5-methyl-3-oxohexyl)cyclopentane-1,3-dione (3 g) in benzene (50 cc) containing anhydrous toluene-p-sulfonic acid (1.5 g) and reflux the mixture with continuous water separation for 45 minutes. Dilute the cooled solution with ether, and wash with water; dry and evaporate. Distil the red residue at 230° (bath temperature) at 0.02 mm to give 13β-ethyl-3-methoxy-7-methylgona-1,3,5(10),8,14-pentaen-17-one; infrared absorption peak at 5.78 μ; ultraviolet absorption peak at 310 mμ ($\epsilon$25,000).

This compound has estrogenic activity, lowers the blood lipid level, and is useful as an intermediate for preparing the hormonal compounds of this invention.

EXAMPLE 51

13β-Methyl-3-hydroxygona-1,3,5(10),8,14-pentaen-17-one

Reflux 2-(6-m-hydroxyphenyl-3-oxohexyl)-2-methylcyclopentane-1,3-dione (0.5 g), the product of Michael condensation of 2-methylcyclopentane-1,3-dione with 6-m-hydroxyphenyl-1-diethylaminohexan-3-one, for 50 minutes in benzene (30 cc) containing toluene-p-sulfonic acid (0.3 g) using a Dean-Stark trap. Add ether (80 cc) to the cooled product and filter off the resulting insoluble material. Wash the ethereal solution in turn with water, saturated aqueous potassium bicarbonate, and brine, and dry. The product is a deep green gum which one takes up in a small quantity of ether; precipitate the insoluble impurities by the addition of light petroleum and filter off. Evaporate the resulting solution to obtain a crystalline residue, which one takes up in a mixture of benzene (10 cc) and ether (2 cc); adsorb the solution on an activated Fuller's earth (10 g). Elute with benzene to obtain 13β-methyl- 3-hydroxygona-1,3,5(10),8,14-pentaen-17-one (0.19 g), m.p. 225° (decomp.).

$C_{18}H_{18}O_2$ Calculated: C, 81.2% H, 6.8%. Found: C, 80.7%; H, 7.0%.

This compound has estrogenic activity, lowers the blood lipid level, and is useful as an intermediate for preparing the hormonal compounds of this invention.

EXAMPLE 52

13β-Methyl-3-hydroxygona-1,3,5(10),8,14-pentaen-17-one

Allow 2-(6-m-hydroxyphenyl-3-oxohexyl)-2-methylcyclopentane-1,3-dione (0.8 g) to stand for 90 minutes at room temperature in benzene (80 cc) containing anhydrous toluene-p-sulfonic acid (5 g). Wash the product with water, followed by aqueous sodium bicarbonate solution, and dry. Remove the solvent by evaporation to obtain a deep green gum; ultraviolet absorption peak at 313 mμ (13,000). When this gum is seeded it becomes solid. Take up the crude material in benzene (15 cc) and adsorb the solution on an activated Fuller's earth (30 g); elute with benzene to obtain pale yellow 13β-methyl-3-hydroxy-gona-1,3,5(10),8,14-pentaen-17-one (0.6 g).

This compound has estrogenic activity, lowers the blood lipid level, and is useful as an intermediate for preparing the hormonal compounds of this invention.

EXAMPLE 53

13β-Methyl-3-hydroxygona-1,3,5(10),8,14-pentaen-17-one

Reflux 2-(6-m-acetoxyphenyl-3-oxohexyl)-2-methylcyclopentane-1,3-dione (0.8 g, the product of Michael condensation of 2-methylcyclopentanedione and a mixture of 6-m-acetoxyphenyl-1-diethylaminohexan-3-one and 6-m-acetoxyphenylhex-1-en-3-one, and containing some of the corresponding free phenolic compound) in benzene (25 cc) with toluene-p-sulfonic acid (0.3 g) for 50 minutes. On cooling add ether (50 cc) and wash the mixture in turn with water, saturated aqueous potassium bicarbonate, and brine; dry over anhydrous magnesium sulfate. The residue after removal of solvent is a purple gum (0.6 g), part of which can be induced to crystallize. Dissolve a portion (0.45 g) of this gum in benzene and adsorb on an activated Fuller's earth (40 g); elute with benzene to obtain 13β-methyl-3-hydroxygona-1,3,5(10),8,14-pentaen-17-one, which one recrystallizes from diisopropyl ether, m.p. 225°–226°; ultraviolet absorption peak at 312.5 mμ (ε23,000); infrared absorption peaks at 2.99 μ, 5.81μ, and 8.00μ.

This compound has estrogenic activity, lowers the blood lipid level, and is useful as an intermediate for preparing the hormonal compounds of this invention.

EXAMPLE 54

13β-Methyl-3-hydroxygona-1,3,5(10),8,14-pentaen-17-one

Place 300 g. of warm polyphosphoric acid in a 1 liter flask fitted with dropping funnel, stirrer and thermometer. Add crude 2-(6-m-hydroxyphenyl-3-oxohexyl)-2-methylcyclopentane-1,3-dione Michael adduct (28.3 g), dissolved by warming in dry benzene (70 cc) dropwise with stirring during 45 minutes to the acid at 40°–50°. Stir the mixture for a further 45 minutes by which time it becomes a very deep red. Add crushed ice with vigorous stirring and extract the resulting mixture with ether (3 × 250 cc). A small quantity of black tar remains insoluble in either phase. Wash the combined ethereal extracts with saturated $KHCO_3$ and brine, and then dry ($MgSO_4$). Remove the solvent on the rotary evaporator (temperature not greater than 40°) to obtain a bright yellow crystalline solid. Wash by decantation with cold 20% ethyl acetate 60°–80° petroleum ether (20 cc), filter and dry to obtain crude 13β-methyl-3-hydroxy-gona-1,3,5(10),8,14-pentaen-17-one (19.35 g., 77%), m.p. 160°–162° (dec.); ultraviolet absorption peak at 312 mμ, (ε22,200).

This compound has estrogenic activity, lowers the blood lipid level, and is useful as an intermediate for preparing the hormonal compounds of this invention.

EXAMPLE 55

13β-Methyl-3-acetoxygona-1,3,5(10),8,14-pentaen-17-one

Mix 13β-methyl-3-hydroxygona-1,3,5(10),8,14-pentaen-17-one with pyridine (3 cc) and acetic anhydride (1 cc) and keep at room temperature for 4 hours. Add ethanol (1 cc) and remove low-boiling material under reduced pressure (0.1 mm) to leave a red gum which crystallizes from a mixture of ethyl acetate and light petroleum. Recrystallize from methanol to obtain crystals of 13β-methyl-3-acetoxygona-1,3,5(10),8,14-pentaen-17-one, melting partially at 161°–166° with resolidification at about 220° and finally melting at 260°–265° (decomp.); infrared absorption peaks at 5.75 μ and 8.27 μ, with absence of an absorption band due to a hydroxy group; ultraviolet absorption peak at 307.5mμ (ε24,000).

This compound has estrogenic activity, lowers the blood lipid level, and is useful as an intermediate for preparing the hormonal compounds of this invention.

EXAMPLE 56

13β-Ethyl-3-hydroxygona-1,3,5(10),8,14-pentaen-17-one

Reflux 2-(6-m-hydroxyphenyl-3-oxohexyl)-2-ethyl-cyclopentane-1,3-dione (2.6 g) for 30 minutes in benzene (70 cc) containing toluene-p-sulfonic acid (0.38 g), and collect the water evolved in the cyclodehydration in a Dean-Stark separator. Work up to obtain a green gum which one dissolves in benzene (30 cc); adsorb the benzene solution on a column of activated Fuller's earth, and elute with benzene to obtain crude 13β-ethyl-3-hydroxygona-1,3,5(10),8,14-pentaen-17-one (0.75 g), as pale yellow crystals, m.p. 153°–156°; ultraviolet absorption peak at 313.5 mμ (ε30,300); infrared absorption peaks at 3.99 μ and 5.81 μ.

This compound has estrogenic activity, lowers the blood lipid level, and is useful as an intermediate for preparing the hormonal compounds of this invention.

EXAMPLE 57

13β-Ethyl-3-hydroxygona-1,3,5(10),8,14-pentaen-17-one

Allow 2-(6-m-hydroxyphenyl-3-oxohexyl)-2-ethylcyclopentane-1,3-dione (8.8 g) to stand 24 hours at room temperature in solution in benzene (430 cc) containing anhydrous toluene-p-sulfonic acid (20 g). Work up the product to obtain a deep red and green gum; take up in benzene (50 cc) and adsorb on activated Fuller's earth (300 g). Elute with benzene to obtain pale green crystals of crude 13β-ethyl-3-hydroxygona-1,3,5(10),8,14-pentaen-17-one (2.05 g) m.p. 149°–151°, the substance melting to a clear liquid on rapid heating; ultraviolet absorption peak at 314 mμ (ε30,000).

This compound has estrogenic activity, lowers the blood lipid level, and is useful as an intermediate for preparing the hormonal compounds of this invention.

EXAMPLE 58

13β-Ethyl-3-hydroxygona-1,3,5(10),8,14-pentaen-17-one

Add 2-(6-m-hydroxyphenyl-3-oxohexyl)-2-ethylcyclopentane-1,3-dione (28.3 g) in benzene (70 cc) during 45 minutes to polyphosphoric acid (300 g) containing 80% phosphorus pentoxide, and maintain at 40°–50°, with stirring. Stir the reaction mixture for a further 45 minutes during which it develops a deep red coloration. Add crushed ice and extract the product with ether. Evaporate the washed and dried extracts at a temperature not greater than 40° to obtain a bright yellow crystalline solid; wash by decantation with light petroleum containing a small proportion of ether; filter and dry to obtain 13β-ethyl-3-hydroxygona-1,3,5(10),8,14-pentaen-17-one (19.35 g), m.p. 160°–162°; ultraviolet absorption peak at 312 mμ (ε22,200).

This compound has estrogenic activity, lowers the blood lipid level, and is useful as an intermediate for preparing the hormonal compounds of this invention.

EXAMPLE 59

13β-Ethyl-3-hydroxygona-1,3,5(10),8,14-pentaen-17-one

Add a solution of 2-(6-m-acetoxyphenyl-3-oxohexyl)-2-ethylcyclopentane-1,3-dione (18.0 g) in benzene (40 cc) during 1½ hours to stirred polyphosphoric acid (180 g., containing 80% phosphorus pentoxide) and maintain at 40°–42°. Keep the reaction mixture at this temperature for a further hour with occasional stirring, add ice and water, and extract the product with ether. Evaporate the washed and dried extracts under reduced pressure to obtain a crude solid product (13.4 g), containing 13β-ethyl-3-hydroxygona-1,3,5(10),8,14-pentaen-17-one and its 3-acetate in a proportion indicated by spectroscopic analysis to be 7:3; ultraviolet absorption peak at 312 mμ (ε12,700).

This 3-hydroxy compound has estrogenic activity, lowers the blood lipid level, and is useful as an intermediate for preparing the hormonal compounds of this invention.

EXAMPLE 60

13β-Ethyl-3-acetoxygona-1,3,5(10),8,14-pentaen-17-one

Dissolve 13β-ethyl-3-hydroxygona-1,3,5(10),8,14-pentaen-17-one (2.45 g) in pyridine (7 cc) and acetic anhydride (4 cc) and allow to stand at room temperature for 16 hours. Remove the solvent under reduced pressure, add ethanol (20 cc) and again evaporate the solvent. Recrystallize the residue from ethanol to give a red crystalline solid, m.p. 122°–124°. Filter the solid through 'Florisil' (100 g) with benzene, evaporate the solvent and recrystallize the product from ethanol to obtain 13β-ethyl-3-acetoxygona-1,3,5(10),8,14-pentaen-17-one, m.p. 129°–130°C; ultraviolet absorption peak at 306 mμ (ε25,500), infrared absorption peaks at 5.78 μ, 8.27 μ, and 9.85 μ.

$C_{21}H_{22}O_3$ Calculated: C, 78.25%; H, 6.9%. Found: C, 78.4%; H, 6.65%.

This compound has estrogenic activity, lowers the blood lipid level, and is useful as an intermediate for preparing the hormonal compounds of this invention.

EXAMPLE 61

13β-Propyl-3-hydroxygona-1,3,5(10),8,14-pentaen-17-one

Cyclodehydrate 2-(6-m-hydroxyphenyl-3-oxohexyl)-2-n-propylcyclopentane-1,3-dione (7.18 g) by heating in benzene (210 cc) containing toluene-p-sulfonic acid (0.75 g), to obtain a deep green gum (6.4 g); chromatograph in benzene on a column of activated Fuller's earth, to give a yellow gum. Crystallize from ethanol, and then from a mixture of benzene and light petroleum to obtain 13β-propyl-3-hydroxygona-1,3,5(10),8,14-pentaen-17-one (0.59 g), m.p. 149°–155° with some premelting at 135°–138°; ultraviolet absorption peak at 313 mμ (ε27,000).

This compound has estrogenic activity, lowers the blood lipid level, and is useful as an intermediate for preparing the hormonal compounds of this invention.

EXAMPLE 62

13β-Ethyl-2,3-dimethoxygona-1,3,5(10),8,14-pentaen-17-one

Dissolve the crude triketone 2-[6-(3,4-dimethoxyphenyl)-3-oxohexyl]-2-ethylcyclopentane-1,3-dione (6.5 g) in dry benzene (100 cc) containing anhydrous toluene-p-sulfonic acid (2.4 g) and reflux under a Dean-Stark water separator for 45 minutes. Wash the cooled solution with water, sodium carbonate solution, and water, and dry. Evaporate the solvent and distil the red gummy residue at 220° (bath temperature) 0.01 mm. to give a yellow gum; recrystallize from methanol to obtain 13β-ethyl-2,3-dimethoxygona-1,3,5(10),8,14-pentaen-17-one; ultraviolet absorption peak at 314 mμ (ε29,000); infrared absorption peaks at 5.84 μ and 8.00 μ.

This compound has estrogenic activity, lowers the blood lipid level, and is useful as an intermediate for preparing the hormonal compounds of this invention.

EXAMPLE 63

13β-Ethyl-1,3-dimethoxygona-1,3,5(10),8,14-pentaen-17-one

Using the triketone 2-[6-(3,5-dimethoxyphenyl)-3-oxohexyl]-2-ethylcyclopentane-1,3-dione (6.5 g), proceed exactly as described in the preceeding example to obtain 13β-ethyl-1,3-dimethoxygona-1,3,5(10),8,14-pentaen-17-one; infrared absorption peaks at 5.74 μ and 8.00 μ.

This compound has estrogenic activity, lowers the blood lipid level, and is useful as an intermediate for preparing the hormonal compounds of this invention.

EXAMPLE 64

13β-Methyl-3-methoxy-D-homogona-1,3,5(10),8-tetraen-17a-one

To 13β-methyl-3-methoxy-D-homogona-1,3,5(10),8,14-pentaen-17a-one (0.3 g) in dioxan (20 cc) add a moderately active Raney nickel catalyst (ca. 0.2 g). Hydrogenate at room temperature and atmospheric pressure until 24 cc. hydrogen has been absorbed. Filter off the catalyst and evaporate the filtrate to obtain a solid; recrystallize from a mixture of ethanol and ethyl acetate to obtain the title product (0.15 g), m.p. 120°–150°C. Ultraviolet absorption peak at 275 mµ (ε14,000).

This compound has estrogenic activity, lowers the blood lipid level, and is useful as an intermediate for preparing the hormonal compounds of this invention.

EXAMPLE 65

13β-Methyl-3-methoxygona-1,3,5(10),8-tetraen-17-one

Dissolve 13β-methyl-3-methoxygona-1,3,5(10),8,14-pentaen-17-one (1 g) in dioxan (33 cc). To the solution add Raney nickel catalyst (ca. 0.5 g) which has been prepared by the method of Pavlic and Adkins, J. Amer. Chem. Soc., 1946, 68, 1471 and allow to stand for 24 hours. Hydrogenate at room temperature and pressure until the theoretical amount of hydrogen (92 cc) for saturation of one ethylenic linkage has been absorbed. Towards the end of this period (5 hours) the rate of hydrogenation drops markedly. Evaporate the solvent after removal of catalyst to obtain a gum which readily crystallizes. Recrystallize once from ethanol to obtain the crude title product (0.69 g), m.p. 110°–120°; ultraviolet absorption peak at 278 mµ (ε14,700).

This compound has estrogenic activity, lowers the blood lipid level, and is useful as an intermediate for preparing the hormonal compounds of this invention.

EXAMPLE 66

13β-Methyl-3-methoxygona-1,3,5(10),8-tetraen-17-one

Shake 13β-methyl-3-methoxygona-1,3,5(10),8,14-pentaen-17-one (1 g) in benzene (35 cc) with a 10% palladium or barium sulfate catalyst (0.3 g) in the presence of hydrogen at atmospheric pressure until 90 cc hydrogen has been absorbed. By the end of this period (1½ hours) the rate of hydrogenation will have slowed down. Filter the mixture and evaporate the solvent to obtain a gum which solidifies; recrystallize from ethanol to obtain the title product (0.68 g), m.p. 110°–120°; ultraviolet absorption peak at 278 mµ (ε13,200).

This compound has estrogenic activity, lowers the blood lipid level, and is useful as an intermediate for preparing the hormonal compounds of this invention.

EXAMPLE 67

13β-Ethyl-3-methoxy-D-homogona-1,3,5(10),8-tetraen-17a-one

Shake 13β-ethyl-3-methoxy-D-homogona-1,3,5(10),8,14-pentaen-17a-one (1.175 g) in tetrahydrofuran (100 cc) with 2% palladium on calcium carbonate (0.5 g., prereduced) in an atmosphere of hydrogen until one molecular equivalent of hydrogen has been absorbed. Filter the catalyst; evaporate the solvent; recrystallize the residue from ethanol to obtain the title product (0.925 g), m.p. 104°–107°; ultraviolet absorption peak at 278 mµ (ε15,680).

This compound has estrogenic activity, lowers the blood lipid level, and is useful as an intermediate for preparing the hormonal compounds of this invention.

EXAMPLE 68

13-Ethyl-3-methoxygona-1,3,5(10),8-tetraen-17-one

Dissolve 13β-ethyl-3-methoxygona-1,3,5(10),8,14-pentaen-17-one (2 g) in dioxan (50 cc) containing Raney nickel (ca. 0.5 g) of moderate activity and shake with hydrogen until 160 cc., the amount corresponding to one molecular proportion has been absorbed. Recrystallize the isolated product from methanol to obtain the title product (1.2 g), m.p. 110°–125°; ultraviolet absorption peak at 280 mµ (ε13,200).

This compound has estrogenic activity, lowers the blood lipid level, and is useful as an intermediate for preparing the hormonal compounds of this invention.

EXAMPLE 69

13β-Propyl-3-methoxygona-1,3,5(10),8-tetraen-17-one

Condense 2-propyl-1,3-cyclopentanedione (13.1 g) in 0.12% methanolic potassium hydroxide solution (90 cc) with 6-m-methoxyphenylhex-1-en-3-one (19.0 g), to obtain crude 2-propyl-2-(6-m-methoxyphenyl-3-oxohexyl)cyclopentane-1,3-dione (25.5 g). Submit this Michael condensation product (23.4 g) to double cyclodehydration; distil the product at 200°/10$^{-4}$ mm. and crystallize the distillate from ethanol, to obtain the tetracyclic diene ketone, m.p. 82°–84°; ultraviolet absorption peak at 310 mµ (ε24,700).

Selectively hydrogenate the diene ketone (5 g) in benzene solution with a palladium on calcium carbonate catalyst until sufficient hydrogen has been taken up to saturate the 14,15-ethylenic bond. Isolate the product (3.5 g) as pink crystals from methanol, m.p. 111°–113°.

This compound has estrogenic activity, lowers the blood lipid level, and is useful as an intermediate for preparing the hormonal compounds of this invention.

EXAMPLE 70

13β-Isopropyl-3-methoxygona-1,3,5(10),8-tetraen-17-one

Shake 13β-isopropyl-3-methoxygona-1,3,5(10),8,14-pentaen-17-one (2 g) in dioxan (50 cc) with a freshly prepared but moderately active Raney nickel catalyst (ca. 0.5 g) in hydrogen at atmospheric pressure. When, after several hours the theoretical amount of hydrogen for half-hydrogenation (160 cc) has been absorbed, filtered off the nickel catalyst and remove the solvent by evaporation. Crystallize the residual gum from methanol to obtain the title product (1.2 g), m.p. 85°–100°C; ultraviolet absorption peak at 280 mµ (ε11,800).

This compound has estrogenic activity, lowers the blood lipid level, and is useful as an intermediate for preparing the hormonal compounds of this invention.

EXAMPLE 71

13β-Butyl-3-methoxygona-1,3,5(10),8-tetraen-17-one

Condense 2-butyl-1,3-cyclopentanedione (2.8 g) in 0.12% methanolic potassium hydroxide solution (8 cc) with 6-m-methoxyphenylhex-1-en-3-one (5 g) by heating the mixture at 80° for 10 hours. Evaporate the solvent under reduced pressure and heat the residue with toluene-p-sulfonic acid (2 g) in benzene (50 cc) for 45 minutes using a Dean-Stark trap, to effect double cyclodehydration. Add ether to the cooled reaction mixture and evaporate the washed and dried ether solution; recrystallize the residue from ethanol to obtain the tetracyclic diene (1.9 g), m.p. 53°–55°; ultraviolet absorption peak at 312 mμ (ε29,200).

Shake this tetracyclic diene (1.38 g) in benzene (45 cc) in hydrogen at atmosphere pressure with a previously reduced 2% palladium on calcium carbonate catalyst (0.5 g). When 100 cc. hydrogen has been absorbed discontinue the hydrogenation and filter off the catalyst. Evaporate solvent and recrystallize the residue from methanol to obtain the title product (1.02 g), m.p. 105°–108°; ultraviolet absorption peak at 278 mμ (ε16,700).

This compound has estrogenic activity, lowers the blood lipid level, and is useful as an intermediate for preparing the hormonal compounds of this invention.

EXAMPLE 72

13β-Isobutyl-3-methoxygona-1,3,5(10), 8-tetraen-17-one

To a pre-reduced suspension of 2% palladium on calcium carbonate catalyst (7.0 g) in benzene (30 cc) add a solution of 13β-isobutyl-3-methoxygona-1,3,5(10),8,14-pentaen-17-one (20.0 g) in benzene (500 cc) and hydrogenate the mixture at atmospheric pressure until one mole equivalent of hydrogen is consumed. After the catalyst is removed by filtration, evaporate the solvent to obtain a gum which on crystallization from ethanol affords the title product (17.1 g.; 71%), m.p. 117°–119°; ultraviolet absorption peak at 278 mμ (ε14,560).

To prepare 6,13β-dimethyl-3-methoxygona-1,3,5(10),8-tetraen-17-one hydrogenate 6,13β-dimethyl-3-methoxygona-1,3,5(10),8,14-pentaen-17-one over a 2% palladium on calcium carbonate catalyst in benzene according to the manipulative procedure described above.

To prepare 7,13β-dimethyl-3-methoxygona-1,3,5(10),8-tetraen-17-one hydrogenate 7,13β-dimethyl-3-methoxygona-1,3,5(10),8,14-pentaen-17-one over a 2% palladium on calcium carbbonate catalyst in benzene according to the manipulative procedure described above.

To prepare 13β-ethyl-1,3-dimethoxygona-1,3,5(10),8-tetraen-17-one hydrogenate 13β-ethyl-1,3-dimethoxygona-1,3,5(10),8,14-pentaen-17-one over a 2% palladium on calcium carbonate catalyst in benzene according to the manipulative procedure described above.

To prepare 13β-ethyl-3-acetoxygona-1,3,5(10),8-tetraen-17-one hydrogenate 13β-ethyl-3-acetoxygona-1,3,5(10),8,14-pentaen-17-one over a 2% palladium on calcium carbonate catalyst in benzene according to the manipulative procedure described above.

To prepare 13β-(3-hydroxypropyl)-3-methoxygona-1,3,5(10),8-tetraen-17-one hydrogenate 13β-(3-hydroxypropyl)-3-methoxygona-1,3,5(10),8,14-pentaen-17-one over a 2% palladium on calcium carbonate catalyst in benzene according to the manipulative procedure described above.

To prepare 13β-ethyl-3-ethoxygona-1,3,5(10),8-tetraen-17-one hydrogenate 13β-ethyl-3-ethoxygona-1,3,5(10),8,14-pentaen-17-one over a 2% palladium on calcium carbonate catalyst in benzene according to the manipulative procedure described above.

To prepare 13β-phenethyl-3-propoxygona-1,3,5(10),8-tetraen-17-one hydrogenate 13β-phenethyl-3-propoxygona-1,3,5(10),8,14-pentaen-17-one over a 2% palladium on calcium carbonate catalyst in benzene according to the manipulative procedure described above.

To prepare 13β-isobutyl-3-pentyloxygona-1,3,5(10),8-tetraen-17-one hydrogenate 13β-isobutyl-3-pentyloxygona-1,3,5(10),8,14-pentaen-17-one over a 2% palladium on calcium carbonate catalyst in benzene according to the manipulative procedure described above.

To prepare 13β-(3-hydroxypropyl)-3-cyclopentyloxygona-1,3,5(10),8-tetraen-17-one hydrogenate 13β-(3-hydroxypropyl)-3-cyclopentyloxygona-1,3,5(10),8,14-pentaen-17-one over a 2% palladium on calcium carbonate catalyst in benzene according to the manipulative procedure described above.

To prepare 13β-phenethyl-3-hydroxygona-1,3,5(10),8-tetraen-17-one hydrogenate 13β-phenethyl-3-hydroxygona-1,3,5(10),8,14-pentaen-17-one over a 2% palladium on calcium carbonate catalyst in benzene according to the manipulative procedure described above.

To prepare 13β(2-diethylaminoethyl)-2,3-dimethoxygona-1,3,5(10),8-tetraen-17-one hydrogenate 13β-(2-diethylaminoethyl)-2,3-dimethoxygona-1,3,5(10),8,14-pentaen-17-one over a 17-one over a 2% palladium on calcium carbonate catalyst in benzene according to the manipulative procedure described above.

To prepare 13β-(3-dimethylaminopropyl)-1-methoxy-3-ethoxy-6-methylgona-1,3,5(10),8-tetraen-17-one hydrogenate 13β-(3-dimethylamino-propyl)-1-methoxy-3-ethoxy-6-methylgona-1,3,5(10),8,14-pentaen-17-one over a 2% palladium on calcium carbonate catalyst in benzene according to the manipulative procedure described above.

To prepare 13β-propyl-2-ethoxy-3-methoxygona-1,3,5(10),8-tetraen-17-one hydrogenate 13β-propyl-2-ethoxy-3-methoxygona-1,3,5(10),8,14-pentaen-17-one over a 2% palladium on calcium carbonate catalyst in benzene according to the manipulative procedure described above.

These compounds have estrogenic activity, lower the blood lipid level, and are useful as intermediates in the preparation of the hormonal compounds of the invention.

EXAMPLE 73

13β-Cetyl-3-methoxygona-1,3,5(10),8-tetraen-17-one

Hydrogenate 13β-cetyl-3-methoxygona-1,3,5(10),8,14-pentaen-17-one (2.39 g) in benzene (140 cc) at atmospheric pressure with a previously reduced 2% palladium oxide on calcium carbonate catalyst (0.3 g) until one molecular equivalent of hydrogen has been absorbed. Remove the catalyst and evaporate to obtain a residue which one crystallizes from ethanol to obtain the title product (2.4 g), as colorless crystals, m.p. 54°–56°; ultraviolet absorption peak at 278 mμ(ε11,500).

$C_{34}H_{52}O_2$ Calculated: C, 82.85%; H, 10.65%. Found: C, 82.75%; H, 10.75.

This compound has estrogenic activity and is useful as an intermediate for preparing the hormonal compounds of this invention.

EXAMPLE 74

13β-Methyl-3-hydroxygona-1,3,5(10),8-tetraen-17-one

Hydrogenate 13β-methyl-3-acetoxygona-1,3,5(10),8,14-pentaen-17-one (0.05 g), obtained by the acetylation of 13βmethyl-3-hydroxygona-1,3,5(10),8,14-pentaen-17-one using pyridine and acetic anhydride in benzene (15 cc) at atmospheric pressure using a 10% palladized charcoal catalyst (0.025 g). Hydrogenation slows down markedly after the requisite quantity of hydrogen for monohydrogenation has been absorbed. Remove the catalyst by filtration and evaporate the solvent to obtain as residue the crude title product.

Immediately take the product up in methanol (4 cc), add 3N sodium hydroxide solution (1 cc) and shake the mixture for 20 minutes. Acidify and extract with ether to obtain a product which one dissolves in benzene and passes through a column of activated Fuller's earth. Evaporate the resulting solution and recrystallize the residue from methanol to obtain the title product, m.p. 225°–227°; ultraviolet absorption peak at 278 mμ (ε15,300).

This compound has estrogenic activity, lowers the blood lipid level, and is useful as an intermediate for preparing the hormonal compounds of this invention.

EXAMPLE 75

13β-Methyl-3-hydroxygona-1,3,5(10),8-tetraen-17-one

Shake 13β-methyl-3-hydroxygona-1,3,5(10),8,14-pentaen-17-one (0.05 g) in benzene (25 cc) in hydrogen at atmospheric pressure using a 10% palladized charcoal catalyst (0.025 g). Hydrogenation becomes very slow when 1.1 moles hydrogen has been absorbed. Filter and evaporate to obtain the title product (0.035 g), recrystallize from methanol to get pale blue crystals, m.p. 225°–228°, melting to a red liquid; ultraviolet absorption peak at 280 mμ (ε12,000).

This compound has estrogenic activity, lowers the blood lipid level, and is useful as an intermediate for preparing the hormonal compounds of this invention.

EXAMPLE 76

13β-Ethyl-3-hydroxygona-1,3,5(10),8-tetraen-17-one

Hydrogenate 13β-ethyl-3-hydroxygona-1,3,5(10),8,14-pentaen-17-one (0.5 g.) in benzene (25 cc.) at atmospheric pressure using a 10% palladized charcoal catalyst (0.025 g.). After the absorption of 1.1 molar equivalents of hydrogen, hydrogenation becomes very slow; remove the catalyst by filtration and evaporate the filtrate to obtain the title product which crystallizes from methanol in colorless plates (0.35 g.), m.p. 235°–9°; ultra-violet absorption peak at 280.5 mμ (ε 15,500).

This compound has estrogenic activity, lowers the blood lipid level, and is useful as an intermediate for preparing the hormonal compounds of this invention.

EXAMPLE 77

13β-Ethyl-3-acetoxygona-1,3,5(10),8-tetraen-17-one

Hydrogenate 13β-ethyl-3-acetoxygona-1,3,5(10),8,14-pentaen-17-one (1.8 g.) dissolved in benzene (25 ml.) at atmospheric pressure in the presence of 10% palladized charcoal (100 mg.). After 1.1 molar equivalents of hydrogen has been absorbed (ca. 12hr.) filter off the catalyst, evaporate the filtrate under reduced pressure and recrystallize the residue from ethanol. Filter the red product through 'Florisil' (60 g.) with benzene-petroleum (3:1), remove the solvent and recrystallize the product from ethanol to obtain the title product, m.p. 132.5°–134.5°; ultra-violet absorption peak at 277 mμ (ε 12,800).

This compound has estrogenic activity, lowers the blood lipid level, and is useful as an intermediate for preparing the hormonal compounds of this invention.

EXAMPLe 78

13β-Propyl-3-hydroxygona-1,3,5(10),8-tetraen-17-one

Shake 13β-propyl-3-hydroxygona-1,3,5(10),8,14-pentaen-17-one (0.59 g.) in benzene (30 cc.) with hydrogen at atmospheric pressure in the presence of a palladized charcoal catalyst (0.3 g.) until the requisite amount of hydrogen for selective semihydrogenation has been absorbed. Filter the catalyst and evaporate the solvent to obtain green crystalline material which one recrystallizes from methanol to obtain the title product (0.36 g.), m.p. 210°–20°, with much decomposition to a red liquid; ultra-violet absorption peak at 281 mμ (ε 11,800).

This compound has estrogenic activity, lowers the blood lipid level, and is useful as an intermediate for preparing the hormonal compounds of this invention.

EXAMPLE 79

13β-Methyl-3-acetoxygona-1,3,5(10),8-tetraen-17-one

Hydrogenate 13β-methyl-3-acetoxygona-1,3,5-(10),8,14,-pentaen-17-one (0.05 g., obtained by the acetylation of 13β-methyl-3-hydroxygona-1,3,5(10),8,14-pentaen-17-one using pyridine and acetic anhydride) in benzene (15 cc.) at atmospheric pressure using a 10% palladized charcoal catalyst (0.025 g.). Hydrogenation slows down markedly after the requisite quantity of hydrogen for monohydrogenation has been absorbed. Remove the catalyst by filtration and evaporate the solvent, to obtain a residue the crude title product.

This compound has estrogenic acitivity, lowers the blood lipid level, and is useful as an intermediate for preparing the hormonal compounds of this invention.

EXAMPLE 80

13β-Methyl-3-methoxy-D-homogona-1,3,5(10),8-tetraen-17aβ-ol

Add 13β-methyl-3-methoxy-D-homogena-1,3,5(10),8-tetraen-17β-one to sodium borohydride (7 g.) in methanol (400 cc.) and reflux for 30 minutes. Acidify the mixture with 50% aqueous acetic acid and evaporate almost to dryness. Add water and extract the product with ether. Wash, dry and evaporate the ethereal solution and crystallize the residue from ethanol to obtain the title product, (19 g.), m.p. 83°–6°; ultra-violet absorption peak at 278 mμ (ε15,800); infrared absorption peaks at 2.96 μ and 6.22 μ.

To prepare 7, 13β-dimethyl-3-methoxygona-1,3,5(10),8-tetraen-17β-ol treat 7, 13β-dimethyl-3-methoxygona-1,3,5-(10),8,-tetraen-17-one with sodium borohydride according to the manipulative procedure described above.

To prepare 13β-methylgona-1,3,5(10),8-tetraene-3,17β-ol treat 13β-methyl-3-hydroxygona-1,3,5(10),8-tetraen-17-one with sodium borohydride according to the manipulative procedure described above.

To prepare 13β-ethyl-2,3-dimethoxygona-1,3,5(10),8-tetraen-17β-ol treat 13β-ethyl-2,3-dimethoxygona-1,3,5(10),8-tetraen-17-one with sodium borohydride according to the manipulative procedure described above.

To prepare 13β-ethyl-3-ethoxygona-1,3,5(10),8-tetraen-17β-ol treat 13β-ethyl-3-ethoxygona-1,3,5(10),8-tetraen-17-one with sodium borohydride according to the manipulative procedure described above.

To prepare 13β-isobutyl-3-pentyloxygona-1,3,5(10),8-tetraen-17β-ol treat 13β-isobutyl-3-pentyloxygona-1,3,5(10),8-tetraen-17-one with sodium borohydride according to the manipulative procedure described above.

To prepare 13β-(3-dimethylaminopropyl)-1,3-dimethoxygona-1,3,5(10),8-tetraen-17β-ol treat 13β-(3-dimethylaminopropyl)-1,3-dimethoxygona-1,3,5(10),8-tetraen-17-one with sodium borohydride according to the manipulative procedure described above.

These compounds have estrogenic activity, lower the blood lipid level, and are useful as intermediates in the preparation of the hormonal compounds of the invention.

EXAMPLE 81

13β-Methyl-3-methoxygona-1,3,5(10),8-tetraen-17β-ol

Add sodium borohydride (0.5 g.) in ethanol (60 cc.) with stirring to 13-methyl-3-methoxygona-1,3,5(10),8-tetraen-17-one (2.0 g.) in ethanol (150 cc.) at 14°–15°. Leave the mixture at room temperature for 1 hour, acidify with glacial acetic acid and evaporate to dryness under reduced pressure. Treat the residue with water, ether-extract and wash and dry. Evaporate the extracts. Recrystallize the residue from a mixture of methanol (15 cc.) and water (3 cc.) to obtain the title product (0.90 g.), m.p. 110°–2°. A sample sublimes at 110°/10$^{-4}$ mm. and has an ultra-violet absorption peak at 277 mβ (ε 14,500).

$C_{19}H_{24}O_2$ Calculated: C, 80.2%; H, 8.5%. Found: C, 79.3%; H, 8.4%.

This compound has estrogenic activity, lowers the blood lipid level, and is useful as an intermediate for preparing the hormonal compounds of this invention.

EXAMPLE 82

13β-Ethyl-3-methoxygona-1,3,5(10),8-tetraen-17β-ol

Hydrogenate 13β-ethyl-3-methoxygona-1,3,5(10),8,14-pentaen-17β-ol (0.31 g.) and recrystallize the product from hexane-ethyl acetate to obtain the title product; ultra-violet absorption peak at 280 mμ (ε 15,000).

This compound has estrogenic activity, lowers the blood lipid level, and is useful as an intermediate for preparing the hormonal compounds of this invention.

EXAMPLE 83

13β-Ethyl-3-methoxygona-1,3,5(10),8-tetraen-17β-ol

Add 13β-ethyl-3-methoxygona-1,3,5(10),8-tetraen-17-one (16.8 g.) to a solution of sodium borohydride (6 g.) in methanol (500 cc.), swirl the mixture which boils spontaneously. When all the material has been added and the reaction has subsided, add acetic acid (15 cc.). Reduce the mixture in volume by evaporation of most of the solvent, add water and extract the product with ether. Evaporate the washed and dried extracts to obtain crude crystalline product (16.8 g.), m.p. 102°–5° on recrystallization from acetonitrile.

This compound has estrogenic activity, lowers the blood lipid level, and is useful as an intermediate for preparing the hormonal compounds of the invention.

EXAMPLE 84

13β-Ethyl-3-methoxy-D-homogona-1,3,5(10),8-tetraen-17aβ-ol

Reduce 13β-ethyl-3-methoxy-D-homogona-1,3,5(10),8-tetraen-17α-one (20.9 g.) exactly as described for the preparation of the 13β-methyl compound to obtain the title product (20 g.), m.p. 110°–112°; infrared absorption peaks at 2.96 μ and 6.23 μ.

This compound has estrogenic activity, lowers the blood lipid level, and is useful as an intermediate for preparing the hormonal compounds of this invention.

EXAMPLE 85

13β-Propyl-3-methoxygona-1,3,5(10),8-tetraen-17β-ol

Hydrogenate 13β-propyl-3-methoxygona-1,3,5(10),8,14-pentaen-17β-ol (0.32 g.) and recrystallize the product from hexane-ethyl acetate to obtain the title product; ultra-violet absorption peak at 280mμ (ε15,000).

This compound has estrogenic activity, lowers the blood lipid level, and is useful as an intermediate for preparing the hormonal compounds of this invention.

EXAMPLE 86

13β-Propyl-3-methoxygona-1,3,5(10),8-tetraen-17β-ol

Add 13β-propyl-3-methoxygona-1,3,5(10),8-tetraen-17-one (3.5 g.) to a solution of sodium borohydride (1.16 g.) in methanol (120 cc.). Heat the reaction mixture to reflux with stirring for 30 minutes. Concentrate the resulting solution, adjust its pH to 6 with aqueous acetic acid and filter off the resulting white precipitate which is the title product, (3.1 g.), m.p. 134°–8°; ultra-violet absorption peak at 278 mμ (ε15,350); infrared showed a band due to hydroxyl but no ketone present.

$C_{21}H_{28}O_2$ Calculated: C, 80.7%; H, 9.0%. Found: C, 80.5%; H, 9.0%.

This compound has estrogenic activity, lowers the blood lipid level, and is useful as an intermediate for preparing the hormonal compounds of this invention.

EXAMPLE 87

13β-Butyl-3-methoxygona-1,3,5(10),8-tetraen-17β-ol

Add sodium borohydride (12.1 g.) to 13β-butyl-3-methoxygona-1,3-5(10),8-tetraen-17-one (36.2 g.) in ethanol (1200 cc.) and reflux the mixture for 1 hour. On cooling, acidify the mixture with aqueous acetic acid and evaporate to dryness under reduced pressure. Add water to the residue and extract the product with ether. Work up in the usual manner to obtain a residue; recrystallize from hexane to obtain the 13-n-butyl-title product (26.9 g.) m.p. 90°–100°; ultraviolet absorption peak at 279 mμ (ε15,600); infrared absorption peak at 2.88 μ, no absorption in the 5.71-5.88 region.

$C_{22}H_{30}O_2$ Calculated: C, 80.9%; H, 9.3%. Found: C, 81.0%; H, 9.0%.

This compound possesses estrogenic activity, lowers the blood lipid level, and is useful as an intermediate for preparing the hormonal compounds of this invention.

EXAMPLE 88

13β-Isobutyl-3-methoxygona-1,3,5(10),8-tetraen-17β-ol

To a stirred solution of sodium borohydride (6.0 g.) in methanol (500 cc. under nitrogen) add 13β-isobutyl-3-methoxygona-1,3,5(10),8-tetraen-17-one (17 g.). Gently heat the reaction mixture for one minute to initiate the reaction and then allow to stand for one hour at room temperature. After adding cautiously glacial acetic acid (20 cc.), concentrate the solution in vacuo to ⅓ of its volume followed by addition of water. Extract the product with ether. Wash the ethereal solution successively with water, sodium bicarbonate, and water, and dry. Evaporate the ether to obtain 13β-isobutyl-3-methoxygona-1,3,5(10),8-tetraen-17β-ol as a gum, (17.0 g.; 99%); ultraviolet absorption peak at 278 mμ (ε14,560).

This compound has estrogenic activity, lowers the blood lipid level, and is useful as an intermediate for preparing the hormonal compounds of this invention.

EXAMPLE 89

13β-Cetyl-3-methoxygona-1,3,5(10),8-tetraen-17β-ol

Stir a solution of 13β-cetyl-3-methoxygona-1,3,5(10),8-tetraen-17-one (0.60 g.) and sodium borohydride (0.20 g.) in ethanol (110cc.) for 2 hours and leave overnight. Reflux with stirring for 2 hours, cool, and add an excess of 50% aqueous acetic acid. Evaporate the mixture to dryness under reduced pressure and partition the residue between ether and water. Work up in the usual manner to get an ether solution of the title product as a gum; infrared absorption peak at 3.37 μ (hydroxyl) with no band in the 5.71–5.88 mμ region; ultraviolet absorption peak at 278 mμ.

This compound has estrogenic activity, lowers the blood lipid level, and is useful as an intermediate for preparing the hormonal compounds of this invention.

EXAMPLE 90

13β-Ethylgona-1,3,5(10),8-tetraene-3,17β-diol

Shake 13β-ethylgona-1,3,5-(10),8,14-pentaene-3,17β-diol (0.28 g.) in benzene (35 cc.) with 10% palladised charcoal (300 mg.) in an atmosphere of hydrogen until 25 cc. of hydrogen has been absorbed. Filter off the catalyst, evaporate the solvent and recrystallize the residue from methanol to obtain the title product, m.p. 234°-8°; ultraviolet absorption peak at 280 mμ (ε 41,200).

This compound has estrogenic activity, lowers the blood lipid level and is useful as an intermediate for preparing the hormonal compounds of this invention.

EXAMPLe 91

13β-Propylgona-1,3,5(10),8-tetraene-3,17β-diol

Hydrogenate 13β-propylgona-1,3,5(10),8,14-pentaene-3,17β-diol (0.31 g.) exactly as described in the previous example to obtain the title product, m.p. 210°–218°; ultraviolet absorption peak at 280 mμ (ε12,000), This compound possesses estrogenic activity, lowers the blood lipid level, and is useful as an intermediate for preparing the hormonal compounds of this invention.

EXAMPLE 92

13β-Ethyl-3,17β-dimethoxygona-1,3,5(10),8-tetraene

Shake 13β-ethyl-3,17β-dimethoxygona-1,3,5(10),8,14-pentaene (1 g.) in 10),(50 cc.) with 2% palladium on calcium carbonate (0.5 g.) in an atmosphere of hydrogen until 1 molar equivalent of hydrogen (85cc.) has been absorbed. Filter the catalyst and evaporate the solvent to obtain the title product, m.p. 94°–7°; ultraviolet absorption peak at 278 mμ (ε16,400.).

This compound possesses estrogenic activity, lowers the blood lipid level, and is useful as an intermediate for preparing the hormonal compounds of this invention.

EXAMPLE 93

13β-Ethyl-3-methoxy-17,17-ethylenedioxygona-1,3,5(10),8-tetraene

Hydrogenate 13β-ethyl-3-methoxy-17,17-ethylenedioxygona-1,3,5(10),8,14-pentaene (2.0 g.) in benzene (70 cc.) at atmospheric pressure using a 5% palladium on calcium carbonate catalyst (0.70 g.). Uptake of hydrogen ceases after 150 cc. has been absorbed. Isolate the product and recrystallize from 95% ethanol to obtain the title product (1.3 g.), m.p. 135°–137°; ultraviolet absorption peak at 2.78 mμ (15,100).

$C_{22}H_{28}O_3$ Calculated: C, 77.6%; H, 8.3%. Found: C, 77.5%; H, 8.6%.

This compound possesses estrogenic activity and blood lipid lowering activity, and is useful as an intermediate for preparing the hormonal compounds of this invention.

To prepare 6, 13β-dimethyl-3-methoxy-17,17-ethylenedioxygona-1,3,5(10),8-tetraene hydrogenate 6,13β-dimethyl-3-methoxy-17,17-ethylenedioxygona-1,3,5(10),8,14-pentaene using a 5% palladium on calcium carbonate catalyst according to the manipulative procedure described above.

To prepare 13β-ethyl-1,3-dimethoxy-17,17-ethylenedioxygona-1,3,5(10),8-tetraene hydrogenate 13β-ethyl-1,3-dimethoxy-17,17-ethylenedioxy-gona-1,3,5(10),8,14-pentaene using a 5% palladium on calcium carbonate catalyst according to the manipulative procedure described above.

To prepare 13β-phenethyl-3-propoxy-17,17-ethylenedioxygona-1,3,5(10),8-tetraene hydrogenate 13β-phenethyl-3-propoxy-17,17-ethylenedioxygona-1,3,5(10),8,14-pentaene using a 5% palladium on calcium carbonate catalyst according to the manipulative procedure described above.

To prepare 13β-(3-hydroxypropyl)-3-cyclopentyloxy-17,17-ethylenedioxygona-1,3,5-(10),8-tetraene hydrogenate 13β-(3-hydroxypropyl)-3-cyclopentyloxy-17,17-ethylenedioxygona-1,3,5(10),8,14-pentaene using a 5% palladium on calcium carbonate catalyst according to the manipulative procedure described above.

These compounds possess estrogenic and blood lipid lowering activity and are useful as intermediates in the preparation of the hormonal compounds of this invention.

EXAMPLE 94

13β-Ethyl-3-methoxy-17,17-(2,2-dimethylpropylenedioxy)-gona-1,3,5,(10),8-tetraene Shake the 13β-ethyl-3-methoxy-17,17-(2,2-dimethylpropylenedioxy) gona-1,3,5(10),8,14-pentaene (5 g.) in benzene (75 cc.) containing 2% palladised calcium carbonate (1.75 g.) with hydrogen at atmospheric pressure until one molecular equivalent has been absorbed. Recrystalize the product from 95% ethanol to obtain the title product; ultraviolet absorption peak at 276.5 mμ (ε13,500).

This compound has estrogenic activity, lowers the blood lipid level, and is useful as an intermediate for preparing the hormonal compounds of this invention.

EXAMPLE 95

13β-Propyl-3-methoxy-17,17-ethylenedioxygona-1,3,5(10),8-tetraene

Shake 13β-propyl-3-methoxy-17,17-ethylenedioxygona-1,3,5(10),8,14-pentaene (2.5 g.) in benzene (80 cc.) with hydrogen at atmospheric pressure in the presence of a 2% palladium on calcium carbonate catalyst (0.9 g.); hydrogen uptake ceases after the requisite amount (161 cc.) for monohydrogenation has been absorbed. Filter and evaporate to obtain a gum, which one crystallizes from ethanol to obtain the title product (1.8 g.), m.p. 119°–120°; ultraviolet absorption peak at 278 mμ (ε15,300).

$C_{23}H_{30}O_3$ Calculated: C, 77.9%; H, 8.5%. Found: C, 77.7%; H, 8.5%.

This compound possesses estrogenic and blood lipid lowering activities and is useful as an intermediate for preparing the hormonal compounds of this invention.

EXAMPLE 96

13β,17α-Diethyl-3-methoxygona-1,3,5(10),8-tetraen-17β-ol

Shake 13β-ethyl-3-methoxy-17α-ethynylgona-1,3,5(10),8-tetraen-17β-ol (1.9 g.) in benzene (100 cc.) with hydrogen at atmospheric pressure in the presence of a prereduced 2% palladium on calcium carbonate catalyst (0.6 g.) until no more hydrogen for selective saturation of the ethynyl group has been absorbed. Filter and evaporate the solvent to obtain a crystalline residue which one recrystallizes from methanol, to obtain the title product (1.5 g.), m.p. 139°–140°; ultraviolet absorption peak at 276 mμ (ε 15,500); infrared absorption peak at 2.79 μ.

To obtain 13β-cetyl-3-methoxy-17β-ethylgona-1,3,5910),8-tetraen-17β-ol hydrogenate 13β-cetyl-3-methoxy-17α-ethynylgona-1,3,5(10),8-tetraen-17β-ol using a prereduced 2% palladium on calcium carbonate catalyst according to the manipulative procedure described above.

To obtain 6, 13β-dimethyl-3-methoxy-17α-ethylgona-1,3,5(10),8-tetraen-17β-ol hydrogenate 6, 13β-dimethyl-3-methoxy-17α-ethynylgona-1,3,5(10),8-tetraen-17β-ol using a prereduced 2% palladium on calcium carbonate catalyst according to the manipulative procedure described above.

To obtain 7, 13β-dimethyl-3-methoxy-17α-ethylgona-1,3,5(10),8-tetraen-17β-ol hydrogenate 7, 13β-dimethyl-3-methoxy-17α-ethynylgona-1,3,5(10),8-tetraen-17β-ol using a prereduced 2% palladium on calcium carbonate catalyst according to the manipulative procedure described above.

To obtain 13β,17α-diethyl-2,3-dimethoxygona-1,3,5(10),8-tetraen-17β-ol hydrogenate 13β-ethyl-2,3-dimethoxy-17α-ethynylgona-1,3,5(10),8-tetraen-17β-ol using a prereduced 2% palladium on calcium carbonate catalyst according to the manipulative procedure described above.

To obtain 13β, 17α-diethyl-3-ethoxygona-1,3,5(10),8-tetraen-17β-ol hydrogenate 13β-ethyl-3-ethoxy-17α-ethynylgona-1,3,5(10),8-tetraen-17β-ol using a prereduced 2% palladium on calcium carbonate catalyst according to the manipulative procedure described above.

To obtain 13β-phenethyl-3-propoxy-17α-ethylgona-1,3,5(10), 8-tetraen-17β-ol hydrogenate 13β-phenethyl-3-propoxy-17α-ethynylgona-1,3,5(10),8-tetraen-17β-ol using a prereduced 2% palladium on calcium carbonate catalyst according to the manipulative procedure described above.

To obtain 13β-(3-hydroxypropyl)-3-cyclopentyloxy-17α-ethylgona-1,3,5(10),8-tetraen-17β-ol hydrogenate 13β-(3-hydroxypropyl)-3-cyclopentyloxy-17α-ethynylgona-1,3,5(10),8-tetraen-17β-ol using a prereduced 2% palladium on calcium carbonate catalyst according to the manipulative procedure described above.

To obtain 13β-(2-diethylaminoethyl)-2,3-dimethoxy-17α-ethylgona-1,3,5(10),8-tetraen-17β-ol hydrogenate 13β-(2-diethylaminoethyl)-2,3-dimethoxy-17α-ethynylgona-1,3,5(10),8-tetraen-17β-ol using a prereduced 2% palladium on calcium carbonate catalyst according to the manipulative procedure described above.

These compounds possess estrogenic activity, and are useful as intermediates in the preparation of the hormonal compounds of this invention.

EXAMPLE 97

13β-Propyl-3-methoxy-17α-ethylgona-1,3,5(10),8-tetraen-17β-ol

Shake 13β-propyl-3-methoxy-17α-ethynylgona-1,3,5(10),8tetraen-17β-ol (1 g.) in benzene (100 cc.) with hydrogen at atmospheric pressure in the presence of a prereduced 2% palladium on calcium carbonate catalyst (0.35 g.). Hydrogenation is interrupted after the requisite amount of hydrogen for selective saturation of the ethynyl group has been absorbed; filter and evaporate to obtain a residue; crystallize from methanol to obtain the title product (0.5 g.), m.p. 106°–108°; ultraviolet absorption peak at 278 mμ (ε14,700); infrared absorption peak at 2.80 μ.

This compound possesses estrogenic activity, and is useful as an intermediate in the preparation of the hormonal compounds of this invention.

EXAMPLE 98

13β-Butyl-3-methoxy-17α-ethynylgona-1,3,5(10),8-tetraen-17β-ol

Shake 13β-butyl-3-methoxy-17α-ethynylgona-1,3,5(10),8-tetraen-17β-ol (3.7 g.) in benzene (150 cc.) with hydrogen at atmospheric pressure in the presence of a prereduced 2% palladium on calcium carbonate catalyst (1.2 g.) until the amount of hydrogen required for selective saturation of the ethynyl group has been absorbed. Crystallize the red gum (3.7 g.) obtained on filtration and evaporation from methanol to obtain crude product (2.9 g.); a portion is further recrystallized from aqueous acetonitrile to give the pure compound, m.p. 72°–76°; ultraviolet absorption peak at 278 mµ (ε15,600); infrared absorption peak at 2.97 µ.

This compound has estrogenic activity, and is useful in the preparation of the hormonal compounds of this invention.

EXAMPLE 99

-D-Homo-13β-ethyl-3-methoxy-gona-1,3,5(10)-trien-17aβ-ol

Add D-homo-13β-ethyl-3-methoxy-gona-1,3,5(10),8-tetraen-17aβ-ol (20 g.) in tetrahydrofuran (525 cc.) to liquid ammonia (1500 cc.) and aniline (250 cc.) and add lithium (5 g.) in pieces. After stirring for 1½ hours discharge the blue color by the addition of sodium nitrite followed by water and isolate the product with ether. Recrystallize the product from methanol to obtain D-homo-13β-ethyl-3-methoxy-gona-1,3,5(10)-trien-17aβ-ol (15 g.), m.p. 103°–105° after previous softening; ultraviolet absorption peak at 280 mµ (ε 2,800); infrared absorption peaks at 2.96 and 6.23 µ.

This compound has estrogenic activity, lowers the blood lipid level, and is useful as an intermediate for preparing the hormonal compounds of this invention.

EXAMPLE 100

13-n-Propyl-3-methoxy-gona-1,3,5(10)-trien-17β-ol

Add 13β-n-propyl-3-methoxy-gona-1,3,5(10),8-tetraen-17β-ol (3.1 g.) dissolved in a mixture of tetrahydrofuran (10 cc.) and freshly distilled aniline (60 cc.) to liquid ammonia (160 cc.) and add lithium metal (1.5 g.) in small pieces. Stir the reaction mixture for 3 hours, then quench with solid ammonium chloride (12.5 g.) and take up in water. Ether-extract the product and evaporate the washed and dried extracts to obtain a semisolid residue of crude 13β-n-propyl-3-methoxy-gona-1,3,5(10)-trien-17β-ol (3.1 g.); ultraviolet absorption peak at 279 mµ (ε1,800).

Dissolve the crude material in ether (75 cc.), add heptane (30 cc.) and distill off the ether, filter the small amount of brown flocculent precipitate, and finally cool the filtrate to precipitate the purified product as an off-white solid (2.3 g.), m.p. 141°–143° C.

This compound possesses estrogenic and blood lipid lowering activity and is useful as an intermediate for preparing the hormonal compounds of this invention.

EXAMPLE 101

13-n-Butyl-3-methoxygona-1,3,5(10)-trien-17β-ol

To 13-n-butyl-3-methoxygona-1,3,5(10),8-tetraen-17β-ol (0.8 g.) in aniline (20 cc.) and tetrahydrofuran (10 cc.) add liquid ammonia (100 cc.), followed by sodium (0.8 g.) in small pieces during 5 minutes while stirring the mixture. After a further 15 minutes stirring, discharge the blue color with solid ammonium chloride. Work up the product with ether in the usual way, and evaporate the resulting ether solution to leave as residue a gum; take this up in hot methanol (10 cc.), filter a little insoluble material and allow the solution to stand for 12 hours at 0° C. Crystals of 13-n-butyl-3-methoxygona-1,3,5(10)-trien-17β-ol are deposited and filtered off (0.6 g.), m.p. 123°–125° C after previous softening and a little melting at 60°–70° C.; ultraviolet absorption peak at 278 mµ (ε2,100); infrared absorption peaks at 2.86–2.97 (broad band), 6.21, 7.94, 9.62 µ.

This compound possesses estrogenic and blood lipid lowering activities and is useful as an intermediate for preparing the hormonal compounds of this invention.

EXAMPLE 102

13β-Isobutyl-3-methoxygona-1,3,5(10)-trien-17β-ol

Add a solution of 13β-isobutyl-3-methoxygona-1,3,5(10),8-tetraen-17β-ol (17.0 g.) in dry tetrahydrofuran (125 cc.; distilled) slowly to a mixture of liquid ammonia (680 cc., distilled), aniline (85 cc., distilled) and tetrahydrofuran (125 cc.) with stirring. Then add lithium (7.9 g.) in small portions. After the addition of lithium is completed, stir the blue mixture for another 3 hours. Discharge the blue color by the cautious addition of ammonium chloride followed by warm (50°) water. Extract the crude product with benzene. Wash the extracts with water, hydrochloric acid, (20%) sodium bicarbonate, water and dry. Evaporate the solvent in vacuo to obtain a gum which on crystallization from ether-petroleum ether gives 13β-isobutyl-3-methoxygona-1,3,5(10)-trien-17β-ol (13.0 g.; 76%); m.p. 103°–104° C.: ultraviolet absorption peak at 2.78 mµ (ε 1,975); infrared absorption peak at 2.83 µ.

This compound possesses estrogenic and blood lipid lowering activity and is useful as an intermediate for preparing the hormonal compounds of this invention.

EXAMPLE 103

13β-Ethyl-3-methoxy-gona-1,3,5(10)-trien-17β-ol

To 13β-ethyl-3-methoxy-gona-1,3,5(10), 8-tetraen-17β-ol (16.8 g.) dissolved in a mixture of aniline (150 cc.) and tetrahydrofuran (50 cc.) add liquid ammonia (400 cc.). Add lithium metal (6.0 g.) gradually in small pieces during 10 minutes, and stir the blue suspension obtained. After 2 hours, add ammonium chloride (50 g.) to the reaction mixture until a clear solution is obtained; then add water (600 cc.) and ether-extract the mixture. Evaporate the washed and dried extracts to obtain as residue a crystalline solid. Recrystallize from hexane (300 cc.), to obtain 13β-ethyl-3-methoxy-gona-1,3,5(10)-trien-17β-ol (14 g.), m.p. 126°–30°.

This compound possesses estrogenic and blood lipid lowering activity and is useful as an intermediate for preparing the hormonal compounds of this invention.

To obtain 13β-cetyl-3-methoxy-gona-1,3,5(10)-trien-17β-ol treat 13β-cetyl-3-methoxy-gona-1,3,5(10),8-tetraen-17β-ol with lithium and aniline in liquid ammonia according to the manipulative procedure described above.

To obtain 7,13β-dimethyl-3-methoxy-gona-1,3,5(10)-trien-17β-ol treat 7,13β-dimethyl-3-methoxy-gona-1,3,5(10),8-tetraen-17β-ol with lithium and aniline in liquid ammonia according to the manipulative procedure described above.

To obtain 13β-ethyl-2,3-dimethoxy-gona-1,3,5(10)-trien-17β-ol treat 13β-ethyl-2,3-dimethoxy-gona-1,3,5(10),8-tetraen-17β-ol with lithium and aniline in liquid ammonia according to the manipulative procedure described above.

To obtain 13β-ethyl-1,3-dimethoxy-gona-1,3,5(10)-trien-17β-ol treat 13β-ethyl-1,3-dimethoxy-gona-1,3,5(10),8-tetraen-17β-ol with lithium and aniline in liquid ammonia according to the manipulative procedure described above.

To prepare 13β-ethyl-3-ethoxy-gona-1,3,5(10)-trien-17β-ol treat 13β-ethyl-3-ethoxy-gona-1,3,5(10),8-tetraen-17β-ol with lithium and aniline in liquid ammonia according to the manipulative procedure described above.

To prepare 13β-phenethyl-3-propoxy-gona-1,3,5(10)-trien-17β-ol treat 13β-phenethyl-3-propoxy-gona-1,3,5(10),8-tetraen-17β-ol with lithium and aniline in liquid ammonia according to the manipulative procedure described above.

To prepare 13β-isobutyl-3-pentyloxy-gona-1,3,5(10)-trien-17β-ol treat 13β-isobutyl-3-pentyloxy-gona-1,3,5(10),8-tetraen-17β-ol with lithium and aniline in liquid ammonia according to the manipulative procedure described above.

To prepare 13β-(3-hydroxypropyl)-3-cyclopentyloxy-gona-1,3,5(10)-trien-17β-ol treat 13β-(3-hydroxypropyl)-3-cyclopentyloxy-gona-1,3,5(10),8tetraen-17β-ol with lithium and aniline in liquid ammonia according to the manipulative procedure described above.

To obtain 13β-(3-dimethylaminopropyl)-3-methoxygona-1,3,5(10), 8-trien-17β-ol treat 13β-(3-dimethylaminopropyl)-3-methoxy-gona-1,3,5(10), 8-tetraen-17β-ol with lithium and aniline in liquid ammonia according to the manipulative procedure described above.

These compounds possess estrogenic and blood lipid lowering activity and are useful as intermediates for preparing the hormonal compounds of this invention.

EXAMPLE 104

13β, 17α-Diethyl-3-methoxygona-1,3,5(10)-trien-17β-ol

Shake 13β-ethyl-3-methoxy-17α-ethylgona-1,3,5(10),9-tetraen-17β-ol (0.3 g.) in ethanol (10 cc.) with 10% palladised charcoal (0.3 g.) in an atmosphere of hydrogen until uptake ceases (25 cc. absorbed). Filter the catalyst and remove the solvent and recrystallize the residue from ethanol to obtain 13β, 17α-diethyl-3-methoxygona-1,3,5(10)-trien-17β-ol (0.11 g.), m.p. 160°–161°.

This compound has estrogenic activity, and is useful as an intermediate for preparing the hormonal compounds of this invention.

EXAMPLE 105

13β-Methyl-3-methoxy-D-homogona-2,5(10)-dien-17aβ-ol

Add 13β-methyl-3-methoxy-D-homogona-1,3,5(10)-trien-17aβ-ol (13 g.) in tetrahydrofuran (300 cc.) to liquid ammonia (650 cc.) followed by the addition of lithium (4.3 g.). After stirring for 30 minutes add absolute ethanol dropwise over a period of 1 hour to discharge the blue color. Precipitate the product with water, filter and dry to give 13β-methyl-3-methoxy-D-homogona-2,5(10)-dien-17aβ-ol, m.p. 148°–155°; infrared absorption peaks at 2.98 μ, 5.88 μ and 5.98 μ.

This compound has estrogenic activity, lowers the blood lipid level, and is useful as an intermediate for preparing the hormonal compounds of this invention.

EXAMPLE 106

13β-Ethyl-3-methoxy-D-homogona-2,5(10)-dien-17aβ-ol

Substitute 13β-ethyl-3-methoxy-D-homogona-1,3,5(10)-trien-17aβ-ol for 13β-methyl-3-methoxy-D-homogona-1,3,5(10)-trien-17aβ-ol to give 13β-ethyl-3-methoxy-D-homogona-2,5(10)-dien-17aβ-ol; m.p. 135°–138°; infrared absorption peaks at 3.03, 5.92, 6.01 μ.

This compound has estrogenic activity, lowers the blood lipid level, and is useful as an intermediate for preparing the hormonal compounds of this invention.

EXAMPLE 107

13β-Ethyl-3-methoxy-gona-2,5(10)-dien-17β-ol

Add 13β-Ethyl-3-methoxy-gona-1,3,5(10)-trien-17β-ol (0.5 g.) in tetrahydrofuran (50 cc.) to stirred liquid ammonia (150 cc.), followed by lithium foil (0.5 g.) and then add ethanol (6 cc.) during 20 minutes. When the blue color is discharged, add water and work up the product with ether, to yield 13β-ethyl-3-methoxy-gona-2,5(10)-dien-17β-ol as a solid (0.47 g.).

To prepare 13β-ethyl-2,3-dimethoxy-gona-2,5(10)-dien-17β-ol react 13β-ethyl-2,3-dimethoxy-gona-1,3,5(10) -trien-17β-ol in tetrahydrofuran with lithium in liquid ammonia according to the manipulative procedure described above.

To prepare 13β-ethyl-1,3-dimethoxy-gona-1(10), 3-dien-17β-ol react 13β-ethyl-1,3-dimethoxy-gona-1,3,5,(10)-trien-17β-ol in tetrahydrofuran with lithium in liquid ammonia according to the manipulative procedure described above.

To prepare 13β-ethyl-3-ethoxy-gona-2,5(10)-dien-17β-ol react 13β-ethyl-3-ethoxy-gona-1,3,5(10)-trien-17β-ol in tetrahydrofuran with lithium in liquid ammonia according to the manipulative procedure described above.

To prepare 13β-phenethyl-3-n-propoxy-gona-2,5(10)-dien-17β-ol react 13β-phenethyl-3-n-propoxy-gona-1,3,5(10)-trien-17β-ol in tetrahydrofuran with lithium in liquid ammonia according to the manipulative procedure described above.

To prepare isobutyl-3-n-pentoxy-gona-2,5(10)-dien-17β-ol react 13β-isobutyl-3-n-pentoxy-gona-1,3,5(10)-trien-17β-ol in tetrahydrofuran with lithium in liquid ammonia according to the manipulative procedure described above.

To prepare 13β-(3-hydroxypropyl)-3-cyclopentoxy-gona-2,5(10)-dien-17β-ol react 13β-(3-hydroxypropyl)-3-cyclopentoxy-gona-1,3,5(10)-trien-17β-ol in tetrahydrofuran with lithium in liquid ammonia according to the manipulative procedure described above.

To prepare 13β-(3-dimethylaminopropyl)-1,3-dimethoxy-gona-1(10),3-dien-17β-ol react 13β-(3-dimethylaminopropyl)-1,3-dimethoxy-gona-1,3,5(10)-trien 17β-ol in tetrahydrofuran with lithium in liquid ammonia according to the manipulative procedure described above.

These compounds have estrogenic acitivty, lower the blood lipid level, and are useful as intermediates in the preparation of the hormonal compounds of the invention.

EXAMPLE 108

13β-Ethyl-3-methoxy-gona-2,5(10)-dien-17β-ol

To 13β-ethyl-3-methoxy-gona-1,3,5(10)-trien-17β-ol (1.0 g.) in 1-methoxypropan-2-ol (100 cc.) add liquid ammonia (200 cc.), followed by lithium metal (1.2 g.) in small pieces with stirring. After discharge of the blue color add an excess of ammonium chloride, followed by water; filter off the crude 13β-ethyl-3-methoxy-gona-2,5(10)-dien-17β-ol and dry, m.p. 98°–104°. No selective ultra-violet absorption beyond 220 mμ; infrared absorption peaks at 3.03, 5.92, 6.01 μ.

This compound has estrogenic activity, lowers the blood lipid level, and is useful as an intermediate for preparing the hormonal compounds of this invention.

EXAMPLE 109

13β-n-Propyl-3-methoxy-gona-2,5(10)-dien-17β-ol

Dissolve 13β-n-propyl-3-methoxy-gona-1,3,5(10)-dien-17β-ol in a mixture of freshly distilled pyrrole (50 cc.) and liquid ammonia (100 cc.) and then add lithium (1.0 g.) in small pieces as quickly as the production of foam permits. When the blue color is discharged, add excess ammonium chloride, followed by water (100 cc.) Extract the product into ether, wash, dry and evaporate. Recrystallize the residue (0.9 g.), from methanol, to give 13β-n-propyl-3-methoxy-gona-2,5(10)-dien-17β-ol (0.65 g.), m.p. 153°–6°; no selective ultra-violet absorption beyond 220 mμ; infrared absorption peaks at 2.91, 5.90, 6.04 μ.

This compound has estrogenic activity, lowers the blood lipid level, and is useful as an intermediate for preparing the hormonal compounds of this invention.

EXAMPLE 110

13β-isopropyl-3-methoxy-gona-2,5(10)-dien-17β-ol

Add liquid ammonia (100 cc.) to 13β-isopropyl-3-methoxy-gona-1,3,5(10)-trien-17β-ol (0.5 g.) in tetrahydrofuran (50 cc.) followed by lithium metal (0.5 g.), and stir the solution for 10 minutes. Then add ethanol (6 cc.) dropwise. When the blue color is discharged, add water and extract the product with ether. Evaporate the washed and dried extracts to give crude 13β-isopropyl -3-methoxy-gona-2,5(10)-dien-17β-ol (0.5 g.) as colorless gum.

This compound has estrogenic activity, lowers the blood lipid level, and is useful as in intermediate for preparing the hormonal compounds of this invention.

EXAMPLE 111

13β-n-Butyl-3-methoxy-gona-2,5(10)-dien-17β-ol

Add 13β-n-butyl-3-methoxy-gona-1,3,5(10)-trien-17β-ol (0.5 g.) in a mixture of tetrahydrofuran (5 cc.) and ether (15 cc.) dropwise to a stirred solution of lithium (0.5 g.) in liquid ammonia (60 cc.). After 5 minutes beyond completion of addition, add ethanol (8 cc.) dropwise and when the blue color is discharged, add water and extract the mixture with ether. Work up in the usual way to give 13β-n-butyl-3-methoxy-gona-2,5(10)-dien-17β-ol as a crystalline solid, m.p. 135°–9°; infrared absorption peaks at 2.97, 6.25, 6.38 and 8.16 μ.

This compound has estrogenic activity, lowers the blood lipid level, and is useful as an intermediate for preparing the hormonal compounds of this invention.

EXAMPLE 112

13β-Ethyl-3-ethoxy-gona-2,5(10)-dien-17β-ol

Heat under reflux 13β-ethyl-3-hydroxy-gona-1,3,5(10)-trien-17β-ol (1.75 g.) and potassium carbonate (3 g.) for six hours with ethanol (40 cc.) and ethyl iodide (20 cc.) in a nitrogen atmosphere. Then concentrate the solution to half its original volume, add water and take the product up in ether. Wash, dry and evaporate the ethereal solution and recyrstallize the residue from hexane to give 13β-ethyl-3-ethoxy-gona-1,3,5(10)-trien-17β-ol. Add this product (0.5 g.), tetrahydrofuran (50 cc.) to liquid ammonia (100 cc.) and add lithium (0.5 g.). After stirring for 10 minutes add a mixture of ethanol (6 cc.) and tetrahydrofuran (10 cc.) over a period of 20 minutes, and when the blue color is discharged add water and extract the mixture with ether. Wash, dry and evaporate the ethereal solution and recrystallize the residue from ethanol to give 13β-ethyl-3-ethoxy-gona-2,5(10)-dien-17β-ol. No selective ultra-violet absorption beyond 220 mμ.

This compound has estrogenic activity, lowers the blood lipid level, and is useful as an intermediate for preparing the hormonal compounds of this invention.

EXAMPLE 113

13β-Ethyl-3-n-propoxy-gona-2,5(10)-dien-17β-ol

Use n-propyl iodide (20 cc.) instead of ethyl iodide and proceed exactly as described for the 3-ethoxy compound to give 13β-ethyl-3-n-propoxy-gona-2,5(10)-dien-17β-ol; no selective ultra-violet absorption beyond 220 mμ.

This compound has estrogenic activity, lowers the blood lipid level, and is useful as an intermediate for preparing the hormonal compounds of this invention.

EXAMPLE 114

13β-Methyl-3-methoxy-D-homo-gona-2,5(10)-dien-17a-one

Reflux 13β-methyl-3-methoxy-D-homo-gona-2,5(10)-dien-17aβ-ol (4 g.) under nitrogen in toluene (130 cc.) containing cyclohexanone (40 cc.) and aluminum isopropylate (1.8 g.) for 3 hours. Cool, add water (40 cc.) followed by anhydrous sodium sulphate (40 g.) and filter the mixture. Evaporate the filtrate to dryness, first at 30°/20 mm. then at 50°/0.1 mm. to afford 13β-methyl-3-methoxy-D-homo-gona-2,5(10)-dien-17a-one. Infrared absorption peaks at 5.85, 5.92, 6.01 μ.

This compound has estrogenic activity, lowers the blood lipid level, and is useful as an intermediate for preparing the hormonal compounds of this invention.

EXAMPLE 115

13β-Ethyl-3-methoxy-D-homo-gona-2,5(10)-dien-17a-one

Reflux 13β-ethyl-3-methoxy-D-homo-gona-2,5(10)-dien-17aβ-ol (10 g.) with aluminum isopropylate (8 g.) in dry toluene (450 cc.) and dry cyclohexanone (140 cc.) for 4 hours in an atmosphere of nitrogen. Decompose the cooled solution with water (ca. 25 cc.) and dry by the addition of sodium sulphate. Filter the mixture and remove the solvents first at 20 mm. Hg. and then at 90° 0.2 mm. Hg. Dry the residue over phosphorus pentoxide in a desiccator to give 13β-ethyl-3-methoxy-D- homo-gona-2,5(10)-dien-17a-one (11.1 g.), m.p. 138°–145°C; infrared absorption peaks at 5.88, 6μ.

This compound has estrogenic activity, lowers the blood lipid level, and is useful as an intermediate for preparing the hormonal compounds of this invention.

EXAMPLE 116

13β-Ethyl-3-methoxy-gona-2,5(10)-dien-17-one

Reflux a mixture of 13β-ethyl-3-methoxy-gona-2,5(10)-dien-17β-ol (0.8 g.), aluminium isopropoxide (0.36 g.), toluene (26 cc.) and cyclohexanone (8 cc.) under nitrogen for 3 hours. Allow the solution to cool under nitrogen, add water (5 cc.) and shake the mixture vigorously. Add anhydrous sodium sulphate (5 g.), shake the mixture again, and then allow to stand for 30 minutes. Filter the solution, combine the filtrate with ether-washings of the residue, and evaporate, first at 30°/20 mm., then at 50°/0.1 mm. to leave as a crystalline solid 13β-ethyl-3-methoxy-gona-2,5(10)-dien-17-one; infrared absorption peaks at 5.78, 5.92, 6.01 μ, with no absorption due to hydroxyl.

To prepare 13β-n-propyl-3-methoxy-gona-2,5(10)-dien-17-one react 13β-n-propyl-3-methoxy-gona-2,5(10)-dien-17β-ol in toluene with cyclohexanone and aluminium isopropoxide according to the manipulative procedure described above.

To prepare 13β-isopropyl-3-methoxy-gona-2,5(10)-dien-17-one react 13β-isopropyl-3-methoxy-gona-2,5(10)-dien-17β-ol in toluene with cyclohexanone and aluminium isopropoxide according to the manipulative procedure described above.

To prepare 13β-isobutyl-3-methoxy-gona-2,5(10)-dien-17-one react 13β-isobutyl-3-methoxy-gona-2,5(10)-dien-17β-ol in toluene with cyclohexanone and aluminium isopropoxide according to the manipulative procedure described above.

To prepare 13β-ethyl-3-ethoxy-gona-2,5(10)-dien-17-one react 13β-ethyl-3-methoxy-gona-2,5(10)-dien-17β-ol in toluene with cyclohexanone and aluminium isopropoxide according to the manipulative procedure described above.

To prepare 13β-ethyl-3-n-propoxy-gona-2,5(10)-dien-17-one react 13β-ethyl-3-n-propoxy-gona-2,5(10) -dien-17β-ol intoluene with cyclohexanone and aluminium isopropoxide according to the manipulative procedure described above.

To prepare 13β-ethyl-2,3-dimethoxy-gona-2,5(10)-dien-17-one react 13β-ethyl-2,3-dimethoxy-gona-2,5(10)-dien-17β-ol in toluene with cyclohexanone and aluminium isopropoxide according to the manipulative procedure described above.

To prepare 13β-ethyl-1,3-dimethoxy-gona-1(10),3-dien-17-one react 13β-ethyl-1,3-dimethoxy-gona-1(10),3-dien-17β-ol in toluene with cyclohexanone and aluminium isopropoxide according to the manipulative procedure described above.

To prepare 13β-phenethyl-3-n-propoxy-gona-2,5(10)-dien-17-one react 13β-phenethyl-3-n-propoxy-gona-2,5(10)-dien-17β-ol intoluene with cyclohexanone and aluminium isopropoxide according to the manipulative procedure described above.

To prepare 13β-isobutyl-3-n-pentoxy-gona-2,5(10)-dien-17-one react 13β-isobutyl-3-n-pentoxy-gona-2,5(10)-dien-17β-ol in toluene with cyclohexanone and aluminium isopropoxide according to the manipulative procedure described above.

To prepare 13β-(3-hydroxypropyl)-3-cyclopentoxy-gona-2,5(10)-dien-17-one react 13β-(3-hydroxypropyl)-3-cyclopentoxy-gona-2,5(10)-dien-17β-ol in toluene with cyclohexanone and aluminium isopropoxide according to the manipulative procedure described above.

To prepare 13β-(3-dimethylaminopropyl)-1,3-dimethoxy-gona-1(10), 3-dien-17-one react 13β-(3-dimethylaminopropyl)-1,3-dimethoxy-gona-1(10),3-dien-17β-ol intoluene with cyclohexanone and aluminium isopropoxide according to the manipulative procedure described above.

These compounds have estrogenic activity and are useful as intermediates in the preparation of the hormonal compounds of the invention.

EXAMPLE 117

13β-n-Propyl-3-methoxy-gona-2,5(10)-dien-17-one

Reflux 13β-n-propyl-3-methoxy-gona-2,5(10)-dien-17β-ol (3.0 g.) with aluminium isopropoxide in toluene and cyclohexanone according to the conditions of Oppenauer oxidation. Isolate and recrystallize the product from methanol to give 13β-n-propyl-3-methoxy-gona-2,5(10)-dien-17-one (2.0 g.), m.p. 128°–31° C. with softening at 125°.

$C_{21}H_{30}O_2$ Calculated: C, 80.2 H, 9.6%. Found: C, 80.0 H, 9.55%.

This compound has estrogenic activity and is useful as an intermediate for preparing the hormonal compounds of this invention.

EXAMPLE 118

13β-n-Butyl-3-methoxy-gona-2,5(10)-dien-17-one

Reflux 13β-n-butyl-3-methoxy-gona-2,5(10)-dien-17β-ol (8 g.) in toluene (450 cc.) containing cyclohexanone (120 cc.) and aluminium isopropoxide (5 g.) under nitrogen for 4 hours. Cool, and add water (15 cc.) dropwise, followed by anhydrous sodium sulphate. Filter the mixture, wash the residue with ether and combine the filtrate and washings, dry and evaporate finally at 90°/1.05 mm. to give 13β-n-butyl-3-methoxy-gona-2,5(10)-dien-17-one (6.0 g.), m.p. 124°–128°, (from methanol); infrared absorption peaks at 5.80, 6.02 μ.

This compound has estrogenic activity, and is useful as an intermediate for preparing the hormonal compounds of this invention.

EXAMPLE 119

13β-Methyl-3-methoxy-17aα-ethynyl-D-homo-gona-2,5(10)-dien-17aβ-ol

Add a solution of 13β-methyl-3-methoxy-D-homo-gona-2,5(10) diene-17a-one (6.5 g.) in dimethylacetamide (50 cc.) to a stirred suspension of lithium acetylide (4.25 g.) in dioxane (25 cc.), ethylene diamine (1 cc.), and dimethylacetamide (25 cc.) in an atmosphere of acetylene. After stirring for 20 hours pour the mixture onto crushed ice (150 g.) and extract with benzene. Wash, dry and evaporate the extracts and recrystallize the residue from ethanol to give 13β-methyl-3-methoxy-17a α-ethynyl-D-homogona-2,5(10)-dien-17aβ-ol; infrared absorption peaks at 2.88, 3.05, 5.90, 6.01 μ.

This compound is useful as an intermediate for preparing the novel compositions of this invention which have hormonal activity.

EXAMPLE 120

13β-Ethyl-3-methoxy-17aα-ethynyl-D-homo-gona-2,5(10)-dien-17aβ-ol

Dissolve 13β-ethyl-3-methoxy-D-homo-gona-2,5(10)-diene-17-one (8.8 g.) in dimethylacetamide (70 cc.) and add a suspension of lithium acetylide (10 g.) in ethylenediamine-dioxan (1:1; 60 cc.). Then pass acetylene over the surface of the stirred mixture for 15 hours. Decompose the reaction mixture by pouring onto ice, collect the product in ether and evaporate the washed, dried ether solution to bide 13β-ethyl-3-methoxy-17aα-ethynyl-D-homo-gona-2,5(10)-diene1-7aβ-ol; m.p. 118-124° (7 g.) 74%. Infrared absorption peaks at 2.85, 3.06, 5.90, 6.0 μ.

This compound is useful as an intermediate for preparing the novel compositions of this invention which have hormonal activity.

EXAMPLE 121

13β-Ethyl-3-methoxy-17α-ethynyl-gona-2,5(10)-diene-17β-ol

Add a suspension of lithium aluminum acetylide (obtained by passing excess acetylene through a solution of lithium aluminum hydride (2.0 g.). in tetrahydrofuran (25 cc.) with stirring to 13β-ethyl-3-methoxy-gona-2,5(10)-dien-17-one (0.6 g.) in tetrahydrofuran (5 cc.). After standing for 18 hours, add ether (40 cc.) folowed by the careful dropwise addition of water until effervescence ceases. Add anhydrous magnesium sulphate (10 g.) and filter the solution and evaporate the filtrate under reduced pressure to give 13β-ethyl-3-methoxy-17α-ethynyl-gona-2,5(10)-dien-17β-ol (0.6 g.). Infrared absorption peaks at 2.80, 3.05, 4.59, 6.00 μ.

This compound is useful as an intermediate for preparing the novel compositions of this invention which have hormonal activity.

EXAMPLE 122

13β-Ethyl-3-methoxy-17α-propynyl-gona-2,5-(10)-diene-17β-ol

Add 13β-ethyl-3-methoxy-gona-2,5(10)-dien-17-one (10 g.) to a solution of propynyl magnesium bromide (prepared from magnesium (6 g.) and ethyl bromide (25 g.) in tetrahydrofuran (500 cc.) and propyne). Stir the mixture for 6 hours under reflux, cool and decompose the water (100 cc.). Add "Celite", filter the resultant sludge and wash the residue thoroughly with ether. Separate the organic phase in the filtrate, wash, dry and evaporate. Reflux the product in methanol for 20 minutes, cool and filter to give 13β-ethyl-3-methoxy-17α-propynyl-gona-2,5(10) -dien-17β-ol (9.5 g.), m.p. 158°-61° after softening at 144°; infrared absorption peaks at 2.90, 3,08, 4.50, 5.88, 6.00 μ; no selective ultra-violet absorption beyond 220 mμ.

This compound is useful as an intermediate for preparing the novel compositions of this invention which have hormonal activity.

EXAMPLE 123

13β-Ethyl-3-methoxy-17α-allyl-gona-2,5(10)-dien-17β-ol

Dissolve 13β-ethyl-3-methoxy-gona-2,5(10) -dien-17-one in tetrahydrofuran (100 cc.) and allyl bromide (11.5 g.), and add the solution dropwise to a refluxing suspension of magnesium (1 g.) in allyl bromide (0.6 g.) and tetrahydrofuran (50 cc.). Allow the mixture to reflux for 6 hours, and then add water (100 cc.) to the cooled solution followed by enough "Celite" to make a thick paste. Filter the mixture, wash the residue thoroughly with ether and separate the organic phase from the filtrate, wash, dry and evaporate the ether solution and crystallize the residue from methanol to give 13β-ethyl-3-methoxy-17 α-allyl-gona-2,5(10) dien-17β-ol (3.8 g.); infrared absorption peaks at 3.03, 5.88. 6.01, 6.10 μ; no selective ultraviolet absorption beyond 220 mμ.

This compound is useful as an intermediate for preparing the novel compositions of this invention which have hormonal activity.

EXAMPLE 124

13β-Ethyl-3-methoxy-17α-(2-isobutenyl)-gona-2,5(10)-dien-17β-ol

Add a suspension of 13β-ethyl-3-methoxy-gona-2,5(10)-dien-17-one (4 g.) in ether (500 cc.) and methallyl chloride (8 g.) to a Grignard solution, prepared from methallyl chloride (8 g.) and magnesium (20 g.) in ether (100 cc.), at such a rate that gentle reflux is maintained. Reflux the mixture for 4 hours and then decompose the cooled solution with water (ca. 100 cc). Add "Celite", filter the resultant pasty mass and wash the residue thoroughly with ether. Separate the organic phase from the filtrate, wash, dry and evaporate, and recrystallize the residue from methanol to give 13β-ethyl-3-methoxy-17α-(2-isobutenyl)gona-2,5(10)-dien-17β-ol (4 g.). Infrared absorption peaks at 2.86, 5.88, 6.01, 6.10 μ; no selective ultraviolet absorption beyond 220 mμ.

This compound is useful as an intermediate for preparing the novel compositions of this invention which have hormonal activity.

EXAMPLE 125

13β-n-Propyl-3-methoxy-17α-ethyl-gona-2,5(10)-dien-17β-ol

Add a solution of 13β-n-propyl-3-methoxy-gona-2,5(10)-dien-17-one (1.74 g.) in dry tetrahydrofuran (25 cc.) slowly to a stirred suspension of acetylene dimagnesium bromide (from magnesium, 0.36 g.) in tetrahydrofuran. After completion of the reaction decompose the Grignard complex with saturated ammonium chloride solution (100 cc.) and work up the product by means of ethyl acetate, purify by chromatography on neutral alumina, and recrystallize from methanol to give 13β-n-propyl-3-methoxy-17α-ethynyl-gona2,5(10)-dien-17β-ol (0.33 g.), m.p. 91-6° (decomp,); infrared absorption peaks at 3.77, 3.03, 5.88, 5.99 μ (a hydroxyl, a methine group and a dihydroanisole system).

This compound is useful as an intermediate for preparing the novel compositions of this invention which have hormonal activity.

EXAMPLE 126

13β-n-Propyl-3-methoxy-17α-allyl-gona-2,5(10)-dien-17β-ol

Warm allyl bromide (4.5 cc.) with magnesium turnings (107 g.) in ether (40 cc.) and then add 13β-n-propyl-3-methoxy-gona-2,5(10)-dien-17-one (2 g.) in ether (70 cc. ) containing allyl bromide (2.5 cc.) slowly with stirring. Reflux the mixture with stirring for 3 hours, and to the cooled mixture add aqueous sodium potassium tartrate and extract the product with ether. Wash, dry and evaporate the extracts to give a residue which is mainly 13β-n-propyl-3-methoxy-17α-allkyl-gona-2,5(10)-dien-17β-ol.

This compound is useful as an intermediate for preparing the novel compositions of this invention which have hormonal activity.

EXAMPLE 127

13β-n-Propyl-3-methoxy-17α-propynyl-gona-2,5(10)-dien-17β-ol

Add a solution of 13β-n-propyl-3-methoxy-gona-2,5(10)-dien-17-one (7.5 g.) in tetrahydrofuran (250 cc.) with stirring under nitrogen to propynyl magnesium bromide (from ethyl magnesium bromide 39 g. and propyne in tetrahydrofuran (500 cc.). Reflux the mixture with stirring for 3 hours, and on cooling add saturated aqueous ammonium chloride (120 cc.) and extract the product obtained from the washed, dry extracts with ether. Dissolve the residue in boiling methanol and store for 18 hours at −10°. Filter off the crystalline deposit to yield 13β-n-propyl-3-methoxy-17α-propynylgona-2,5(10)-dien-17-β-ol (6.9 g.), m.p. 104°–111°.

To prepare 13β-n-propyl-3-methoxy-17α-methyl-gona-2,5(10)-dien-17β-ol treat 13β-n-propyl-3-methoxy-gona-2,5(10)-dien-17-one with methyl magnesium bromide according to the manipulative procedure described above.

To prepare 13β-isobutyl-3-methoxy-17α-ethyl-gona-2,5(10)-dien-17β-ol treat 13β-isobutyl-3-methoxy-gona-2,5(10)-dien-17-one with ethyl magnesium bromide according to the manipulative procedure described above.

To prepare 13β-isobutyl-3-methoxy-17α-methyl-gona-2,5(10)-dien-17β-ol treat 13β-isobutyl-3-methoxy-gona-2,5(10)-dien-17-one with methyl magnesium bromide according to the manipulative procedure described above.

To prepare 13β,17α-di-ethyl-3-ethoxy-gona-2,5(10)-dien-17β-ol treat 13β-ethyl-3-ethoxy-gona-2,5(10)-dien-17-one with ethyl magnesium bromide according to the manipulative procedure described above.

To prepare 13β-ethyl-3-n-propoxy-17α-methyl-gona-2,5(10)-dien-17β-ol treat 13β-ethyl-3-n-propoxy-gona-2,5(10)-dien-17-one with methyl magnesium bromide according to the manipulative procedure described above.

To prepare 13β, 17α-diethyl-2,3-dimethoxy-gona-2,5(10)-dien-17β-ol treat 13β-ethyl-2,3-dimethoxy-gona-2,5(10)-dien-17-one with ethyl magnesium bromide according to the manipulative procedure described above.

To prepare 13β-ethyl-1,3-dimethoxy-17α-methyl-gona-1(10),3-dien-17β-ol treat 13β-ethyl-1,3-dimethoxy-gona-1(10),3-dien-17-one with methyl magnesium bromide according to the manipulative procedure described above.

To prepare 13β-phenethyl-3-n-propoxy-17α-ethyl-gona-2,5(10)-dien-17β-ol treat 13β-phenethyl-3-n-propoxy-gona-2,5(10)-dien-17-one with ethyl magnesium bromide according to the manipulative procedure described above.

To prepare 13β-isobutyl-3-n-pentoxy-17α-methyl-gona-2,5(10)-dien-17β-ol treat 13β-isobutyl-3-n-pentoxy-gona-2,5(10)-dien-17-one woth methyl magnesium bromide according to the manipulative procedure described above.

To prepare 13β-(3-hydroxypropyl)-3-cyclopentoxy-17α-ethyl-gona-2,5-(10)-dien-17β-ol treat 13β-(3-hydroxypropyl)-3-cyclopentoxy-gona-2,5(10)-dien-17-one with ethyl magnesium bromide according to the manipulative procedure described above.

To prepare 13β-(3-dimethylaminopropyl)-1,3-dimethoxy-17α-methyl-gona-1(10),3-dien-17β-ol treat 13β-(3-dimethylaminopropyl)-1,3-dimethoxy-gona-1(10),3-dien-17-one with methyl magnesium bromide according to the manipulative procedure described above.

These compounds are useful as intemediates for preparing the novel compositions of this invention which have hormonal activity.

EXAMPLE 128

13β-n-Propyl-3-methoxy-17α-(1-methallyl)-gona-2,5(10)-dien-17β-ol

Add a solution of 13β-n-propyl-3-methoxy-gona-2,5(10)-dien-17-one (3.1 g.) in ether (130 cc.) with stirring under nitrogen to crotyl magnesium bromide (from crotyl bromide, 13.5 g., and magnesium, 9.7 g.) in ether. Reflux the mixture for 4 hours, and leave at room temperature overnight. Add saturated aqueous ammonium chloride (70 cc.) and extract the product with ether. Wash, dry and evaporate the extracts to yield 13β-n-propyl-3-methoxy-17α-(1-methallyl)-gona-2,5(10)-dien-17β-ol; infrared absorption peak at 11.0μ.

This compound is useful as an intermediate for preparing the novel compositions of this invention which have hormonal activity.

EXAMPLE 129

13β-n-Propyl-3-methoxy-17α-(2-methallyl)-gona-2,5(10)-dien-17β-ol

Employ the method of the previous example but react 13β-n-propyl-3-methoxygona-2,5(10)-dien-17-one (3.66 g. with 2-methallyl magnesium chloride (from the metal, 8.76 g. and 2-methallyl chloride, 10.9 g.). Purify the crude product by extraction with boiling methanol to afford a residue of 13β-n-propyl-3-methoxy-17α-(2-methallyl)-gona-2,5(10)-dien-17β-ol (3.87 g.), m.p. 135-140°; infrared absorption peaks at 2.87, 5.90, 6.00, 6.09 μ.

This compound is useful as an intermediate for preparing the novel compositions of this invention which have hormonal activity.

EXAMPLE 130

13β-n-Butyl-3-methoxy-17α-ethynyl-gona-2,5(10)-dien-17β-ol

Add a solution of 13β-n-butyl-3-methoxy-gona-2,5(10)-dien-17-one (2 g.) in dimethylacetamide (200 cc.) slowly to a suspension of lithium carbide (2.5 g.) in dimethylacetamide (50 cc.) at 0° in an atmosphere of nitrogen. Stir the mixture at room temperature for 48 hours, cool to 0° and decompose by the dropwise addition of water (100 cc.). Add water and extract with ether to give after removal of the solvent, 13β-n-butyl-3-methoxy-17α-ethynyl-gona-2,5(10)-dien-17β-ol (1.8 g.) as a gum; infrared absorption peaks at 2.95, 3.05, 5.90, 5.99 μ.

EXAMPLE 131

13β-Methyl-D-homo-17a-hydroxy-gon-4-en-3-one

Add 13β-methyl-D-homo-3-methoxy-gona-2,5(10)-dien-17a-ol (0.7 g.) in dioxane (20 cc.) with stirring to methanol (20 cc.) containing 11N hydrochloric acid (2.7 cc.) and water (1 cc.). Continue stirring for 2 hours, add water and extract the mixture with ether. Evaporate the washed and dried extracts, dissolve the residue in benzene and chromatograph on Florex to give 13β-methyl-D-homo-17a-hydroxy-gon-4-en-3-one; ultra-violet absorption peak at 242 m$_{82}$ ($\epsilon$ 17,000); infrared absorption peaks at 3.03, 5.92, 6.01 $\mu$.

This compound has androgenic and anabolic activity and is useful as an intermediate for preparing the hormonal compounds of this invention.

EXAMPLE 132

13β-Ethyl-D-homo-17a-hydroxy-gon-4-en-3-one

Substitute 13β-ethyl-D-homo-3-methoxy-gona-2,5(10)-dien-17a-ol for 13β-methyl-D-homo-3-methoxy-gona-2,5(10)-dien-17a-ol to give 13β-ethyl-D-homo-17a-hydroxy-gon-4-en-3-one; ultra-violet absorption peak at 242m$\mu$($\epsilon$17,000); infrared absorption peaks at 3.03, 5.92, 6.01 $\mu$.

This compound has androgenic and anabolic activity and is useful as an intermediate for preparing the hormonal compounds of this invention.

EXAMPLE 133

13β-Ethyl-17β-hydroxy-gon-4-en-3-one

Add 13β-ethyl-3-methoxy-gona-1,3,5(10)-trien-17β-ol (0.5 g.) in 100 ml. of tetrahydrofuran to 150 ml. of liquid ammonia, followed by 0.5 g. of lithium foil, and stir the mixture for 10 minutes. Add ethanol (6 ml.) and tetrahydrofuran (10 ml.) over a period of 20 minutes. After disappearance of the blue color add water, extract the mixture well with ether and evaporate the washed and dried ether extract. Dissolve the crystalline residue in 50 ml. of methanol and reflux for 30 minutes with 30 ml. of 3N HCL. Remove most of the methanol under reduced pressure, and extract the residue with ether. Chromatograph the ether extract on alumina. Use benzene-ether (1:1) to elute 13-β-ethyl-17β-hydroxy-gon-4-en-3-one; m.p. 152°–55°C.

$C_{19}H_{28}O_2$ Calculated: C, 79.1% H, 9.8%. Found: C, 79.25% H, 9.65%.

This compound has androgenic and anabolic activity and is useful as an intermediate for preparing the hormonal compounds of this invention.

EXAMPLE 134

13β-Ethyl-17β-hydroxy-gon-4-en-3-one

Dissolve 13β-ethyl-3-methoxy-gona-2,5(10)-dien-17β-ol (0.47 g.) in hot methanol (25 cc.). Add 3N hydrochloric acid (15 cc.) and keep the mixture at 70° C. under nitrogen for 1 hour. Add water and work up with ether and chromatograph the resulting gum on activated alumina (40 g.). Elute with ether to give a fraction (0.2 g.) which on recrystallization from light petroleum gives 13β-ethyl-17β-hydroxy-gon-4-en-3-one; m.p. 153-5° C; ultra-violet absorption peak at 240 m$\mu$($\epsilon$ 16,300).

$C_{19}H_{26}O_2$ Calculated: C, 79.1% H, 9.8%. Found: C,79.2% H, 9.7%.

This compound has anabolic and androgenic activity and is useful as an intermediate for preparing the hormonal compounds of this invention.

EXAMPLE 135

13β-Ethyl-17β-hydroxy-gon-4-en-3-one

Add to 13β-ethyl-3-methoxy-gona-2,5(10)-dien-17β-ol (1.0 g.) in methanol (50 cc.), 3N hydrochloric acid (20 cc.); shake the mixture for 2 hours, pour into water, and extract the product with ether. Work up in the usual way and take up the resulting gum in benzene and chromatograph on neutral alumina. Elute with ether to give a crystalline material and recrystallize from a mixture of ether and pentane to yield 13β-ethyl-17β-hydroxy-gon-4-en-3-one (0.5 g.), m.p. 144°–7°; ultra-violet absorption peak at 240 m$\mu$ ($\epsilon$15,500); infrared absorption peaks at 2,94, 6.06, 6.23 $\mu$.

This compound has anabolic and androgenic activity and is useful as an intermediate for preparing the hormonal compounds of this invention.

To prepare 13β-cetyl-17β-hydroxy-gon-4-en-3-one treat 13β-cetyl-3-methoxy-gona-2,5(10)dien-17β-ol with methanolic hydrochloric acid according to the manipulative procedure described above.

To prepare 13β-ethyl-2-methoxy-17β-hydroxy-gon-4-en-3-one treat 13β-ethyl-2,3-dimethoxy-gona-2,5(10)-diene-17β-ol with methanolic hydrochloric acid according to the manipulative procedure described above.

To prepare 13β-phenethyl-17β-hydroxy-gon-4-en-3-one treat 13β-phenethyl-3-methoxy-gona-2,5(10)-diene-17β-ol with methanolic hydrochloric acid according to the manipulative procedure described above.

To prepare 13β-(3-hydroxypropyl)-17β-hydroxy-gon-4-en-3-one treat 13β-(3-hydroxypropyl)-3-methoxy-gona-2,5(10)-diene-17β-ol with methanolic hydrochloric acid according to the manipulative procedure described above.

To prepare 13β-(3-dimethylaminopropyl)-1-oxo-17β-hydroxygonan-3-one treat 13β-(3-dimethylaminopropyl)-1,3-dimethoxy-gona-1(10),3-diene-17β-ol with methanolic hydrochloric acid according to the manipulative procedure described above.

These compounds possess androgenic and anabolic activity and are useful as an intermediate for preparing the hormonal compounds of this invention.

EXAMPLE 136

13β-Ethyl-17β-hydroxy-gon-4en-3-one

Stir 13β-ethyl-17β-hydroxy-gon-5(10)-en-3-one (300 mg.) for 2 hours under nitrogen at room temperature with methanol (10 cc.)-11N hydrochloric acid (0.5 cc.)-water (0.3 cc.). Add sodium bicarbonate (2 g.) and ether (50cc.), filter the mixture, evaporate the ether and recrystallize the residue from ethyl acetate-ether to give 13β-ethyl-17β-hydroxy-gon-4-en-3-one (0.2 g.), m.p. 147°–149°; ultraviolet absorption peak at 242 m$\mu$($\epsilon$ 17,600); infrared absorption peaks at 2.78, 2.90, 6.02, 6.17.

This compound has anabolic and androgenic activity and is useful as an intermediate for preparing the hormonal compounds of this invention.

EXAMPLE 137

13β-Ethyl-17β-hydroxy-gon-4-en-3-one

Add sodium borohydride (200 mg.) in ethanol (25 cc.) to 13β-ethylgon-4-en-3,17-dione (1 g.) in ethanol (50 cc.) at 8°. After 15 minutes add an excess of acetic acid and evaporate the solution to dryness under reduced pressure. Add water, collect the product in ether, and after this work up in the usual manner, recrystallize from a mixture of ether and pentane to obtain 13β-ethyl-17β-hydroxy-gon-4-en-3-one; u;traviolet absorption peak at 240 mμ (ε 15,500); infrared absorption peaks at 2.94, 6.06, 6.23.

This compound has androgenic and anabolic activity and is useful as an intermediate for preparing the hormonal compounds of this invention.

EXAMPLE 138

13β-n-Propyl-17β-hydroxy-gon-4-en-3-one

Add 3N hydrochloric acid (1 cc.) to a solution of 13β-n-propyl-3-methoxy-gona-2,5(10)-dien-17β-ol (0.61 g.) in boiling methanol (70 cc.) and cool the mixture immediately and allow to stand for 4 ½ hours. Pour the product into water (300 cc.) and extract the mixture with ether; work up in the usual way to give as residue an amorphous solid (0.6 g.). Crystallize this solid from a mixture of ether and hexane. Take up the resulting solid in benzene (20 cc.) and chromatograph on a column of neutral alumina. Elute the product with ether and recrystallize from a mixture of ether and hexane to obtain 13β-n-propyl-17β-hydroxy-gon-4-en-3-one (0.08 g.), mp. 126°-7°; ultraviolet absorption peak at 240 mμ ε15,000); infrared absorption peaks at 2.92, 6.01, 6.20 μ. Evaporation of the mother liquors gives a second, polymorphic, form of the same substance (0.17 g.), m.p. 144°-5°, having ultraviolet and infrared spectra identical with the first material; a mixture of the two forms has m.p. 144°-5°.

This compound has androgenic and anabolic activity and is useful as an intermediate for preparing the hormonal compounds of this invention.

EXAMPLE 139

13β-n-Propyl-17β-hydroxy-gon-4-en-3-one

By substituting an equivalent amount of 13β-n-propyl-17β-hydroxy gon-5 (10)-en-3-one for 13β-ethyl-17β-hydroxy-gon-5(10)-en-3-one in example 136, there is obtained 13β-n-propyl-17β-hydroxy-gon-4-en-3-one; infrared absorption peaks at 2.92, 6.01, 6.20 μ; ultraviolet peak at 240 mμ (ε15,000).

This compound has androgenic and anabolic activity and is useful as an intermediate for preparing the hormonal compounds of this invention.

EXAMPLE 140

13β-Isopropyl-17β-hydroxy-gon-4-en-3-one

Dissolve 13β-isopropyl-3-methoxy-gona-2,5(10)-dien-17β-ol in methanol (36 cc.), concentrated hydrochloric acid (2.4 cc.) and water (1.6 cc.) and allow the mixture to stand at room temperature for 2 hours. Add water and collect the product in ether. Wash, dry and evaporate the ethereal solution and chromatograph the residue on alumina (30 g.). elute with benzene containing 30% ether and evaporate the solvent to obtain 13β-isopropyl-17β-hydroxy-gon4-ne-3-one as a gum; infrared absorption peak at 5.99 μ; ultraviolet absorption peak at 249 mμ (ε12,000).

This compound has progestational activity and is useful as an intermediate for preparing the hormonal compounds of this invention.

EXAMPLE 141

13β-n-Butyl-17β-hydroxy-gon-4-en-3-one

Shake 13β-n-butyl-3-methoxy-gona-2,5(10)-dien-17β-ol (0.49 g.) with concentrated hydrochloric acid (1.2 cc.) in water (0.8 cc.) and methanol (18 cc.) until solution is complete. Allow to stand 2 hours at room temperature, pour the mixture into water and extract the product with ether. Evaporate the washed and dried ether extracts and recrystallize the solid from a mixture of ethyl acetate and ether to obtain the title compound (0.32 g.), m.p. 169°-70°; ultraviolet absorption peak at 240 mμ (ε17,000); infrared absorption peaks at 2.92, 6.01 μ.

This compound has androgenic and anabolic activity and is useful as an intermediate for preparing the hormonal compounds of this invention.

EXAMPLE 142

13β-Isobutyl-17β-hydroxy-gon-4-en-3-one

Add to a mixture of concentrated hydrochloric acid (4.8 cc.), water (3.2 cc.) and methanol (.72 cc.) 13β-isobutyl-3-methoxy-gona-2,5(10)-dien-17βol (2.0 g.). Heat the resulting solution on a steam bath for 30 minutes with stirring. Cool to room temperature, dilute the solution with water (160 cc.) and extract with ether. Wash the ethereal solution with water, sodium bicarbonate, and water, dry over anhydrous sodium sulfate. Filter and remove the solvent under reduced pressure to give a gum. Recrystallize from ethyl acetate to obtain the title compound (0.8 g., 43%, m.p. 124.0°-125.5°; ultraviolet absorption peak at 240 mμ (ε18,200).

$C_{21}H_{32}O_2$ Calculated: C, 79.7%; H, 10.2%. Found : C, 79.5%, H, 10.0%.

This compound has estrogen antagonistic activity and is useful as an intermediate for preparing the hormonal compounds of this invention.

EXAMPLE 143

13β, 17α-diethyl-17β-hydroxy-gon-4-en-3-one

Dissolve 13β, 17α-diethyl-gon-5-en-3, 17β-diol (0.1 g.) in acetone (30cc.) and add a few pieces of solid carbon dioxide. Add 8N-chromic acid dropwise until the color of the solution remains reddish orange (3 drops) and then add isopropanol (1 cc.). Shake the mixture for 5 minutes with 10% aqueous sodium hydroxide (50 cc.) and then add benzene (30 cc.) and remove the organic layer. Wash the organic layer thoroughly with brine and dry over $Na_2SO_4$. Remove the solvent and triturate the residue with ether to give a crystalline precipitate. Recrystallize from ether to obtain the title compound, m.p, 138°-142° undepressed on admixture with authentic material.

This compound has anabolic and androgenic activity and is useful as an intermediate for preparing the hormonal compounds of this invention.

EXAMPLE 144

13β-Ethyl-17β-methoxy-gon-4-en-3-one

Add 13β-ethyl-3, 17β-dimethoxy-gona-2,5(10)-diene (0.8 g.) in tetrahydrofuran (5 cc.) to methanol (72 cc.) in an atmosphere of nitrogen and add a mixture of hydrochloric acid (4.8 cc.) and water (3.2 cc.). Add a further 10 cc. of tetrahydrofuran and after 1 hour dilute the solution with water and extract with ether. Wash, dry and evaporate the ethereal extracts and chromatograph the residue on neutral alumina. Remove impurities by elution with benzene. Wash the column with ether, evaporate the eluate and recrystallize the residue from hexane to obtain the title compound (0.2 g.), m.p. 117-119°; ultraviolet absorption λ max. 240 mμ (ε15,800); infrared spectrum (KBr disc) 6.0, 6.2, 8.8, 9.05 μ.

This compound has anabolic and androgenic activity and is useful as an intermediate for preparing the hormonal compounds of this invention.

EXAMPLE 145

13β-Ethyl-gon-4-en-3,17-dione

Add 13β-ethyl-3-methoxy-gona-2,5(10)-dien-17-one (12.9 g.) with stirring under nitrogen to methanol (300 cc.) containing 11N hydrochloric acid (20 cc) and water (13 cc.). Stir two hours and add sodium bicarbonate (21 g.) portionwise. Filter the mixture and evaporate the filtrate to dryness. Recrystallize the residue from ethyl acetate (75 cc.) to obtain the title compound (10 g.), m.p. 158-161° C; ultraviolet absorption peak at 240 mμ (ε17,800); infrared absorption peaks at 5.78, 6.00, 6.17 μ.

$C_{19}H_{26}O_2$ Calculated: C, 79.76%; H, 9.15%; Found: C, 80.0%; H, 9.0%.

This compound is useful as an intermediate for preparing the hormonal compounds of this invention.

EXAMPLE 146

13β-Ethyl-gon-4-en-3,17-dione

Add 13β-ethyl-gon-5(10)-en-3,17-dione (1 g.) with stirring under nitrogen to methanol (25 cc.) containing 11N hydrochloric acid (1.75 cc.) and water (1.1 cc.). Stir for 2 hours, add sodium bicarbonate (1.75 g.) and filter the mixture. Evaporate the filtrate to dryness and recrystallize the residue from ethyl acetate to obtain the title compound; ultraviolet absorption peak at 240 mμ (ε17,800); infrared absorption peaks at 5.78, 6.00, 6.17 μ.

This compound is useful as an intermediate for preparing the hormonal compounds of this invention.

EXAMPLE 147

13β-Ethyl-gon-4-en-3,17-dione

Heat 13β-ethyl-3-methoxy-17,17-ethylenedioxy-gona-2,5(10)-diene (0.1 g.) in glacial acetic acid (2.5 cc.) and water (1 cc.) on a steam bath for 20 minutes, bring finally to boiling and allow to cool. Add aqueous sodium bicarbonate to neturalize the solution and ether extract the product. Wash, dry and evaporate the ether extracts to furnish a residue (0.065 g.); crystallize from a mixture of acetone and light petroleum to obtain the title compound (0.01 g.), m.p. 154°-5°; ultraviolet absorption peak at 239 mμ (ε15,000); infrared absorption peaks at 5.75, 5.96 μ.

This compound is useful as an intermediate for preparing the hormonal compounds of this invention.

EXAMPLE 148

13β-Methyl-D-homo-17aβ-(3-phenylpropionoxy)-gon-4-en-3-one

Add 3-phenylpropionyl chloride (1 cc.) in benzene (3 cc.) to 13β-methyl-D-homo-17aβ-hydroxy-gon-4-en-3-one (1 g.) in pyridine (3.5 cc.) at −20°. Keep the mixture overnight at −10°, add crushed ice and extract the mixture with ether-benzene (1:1). Wash the extracts in turn with 2N aqueous potassium hydroxide, water, 2N hydrochloric acid, and brine, and dry. Evaporate the solvent to give a residue. Dissolve the residue in benzene and chromatograph on silica gel to obtain the title compound: infrared absorption peaks at 5.80, 5.99 μ.

This compound has androgenic and anabolic activity and is useful as an intermediate for preparing the hormonal compounds of this invention.

EXAMPLE 149

13β-Ethyl-D-homo-17aβ-(3-phenylpropionoxy)-gon-4-en-3-one

Substitution of 13β-ethyl-D-homo-17aβhydroxy-gon-4-en-3-one for 13β-methyl-D-homo-17aβhydroxy-gon-4-en-3-one in the preceding example gives the title compound; infrared absorption peaks at 5.78, 5.99 μ.

This compound has anabolic and androgenic activity and is useful as an intermediate for preparing the hormonal compounds of this invention.

EXAMPLE 150

13β-Ethyl-17β-acetoxy-gon-4-en-3-one

Add acetyl chloride (1 cc.) in benzene 95 cc.) to 13 β-ethyl-17β-hydroxy-gon-4-en-3-one (1.5 g.) in pyridine (5 cc.) at −20°. Keep the mixture at −10° for 18 hours, work up and recrystallize the product from methanol to obtain the title compound (0.9 g.); ultraviolet absorption peak at 240 mμ (ε16,700); infrared absorption peaks at 5.75, 5.99 μ.

This compound has anabolic and androgenic activity and is useful as an intermediate for preparing the hormonal compounds of this invention.

To prepare 13β-ethyl-17β-propionoxy-gon-4-en-3-one treat 13β-ethyl-17β-hydroxy-gon-4-en-3-one with propionyl chloride according to the manipulative procedure described above.

To prepare 13β-ethyl-17β-hexanoyloxy-gon-4-en-3-one treat 13β-ethyl-17β-hydroxy-gon-4-en-3-one with hexanoyl chloride according to the manipulative procedure described above.

To prepare 13β-ethyl-17β-heptanoyloxy-gon-4-en-3-one treat 13β-ethyl-17β-hydroxy-gon-4-en-3-one with heptanoyl chloride according to the manipulative procedure described above.

To prepare 13β-ethyl-17β-octanoyloxy-gon-4-en-3-one treat 13β-ethyl-17β-hydroxy-gon-4-en-3-one with octanoyl chloride according to the manipulative procedure described above.

To prepare 13β-ethyl-17β-lauroyloxy-gon-4-en-3-one treat 13β-ethyl-17β-hydroxy-gon-4-en-3-one with lauroyl chloride according to the manipulative procedure described above.

To prepare 13β-ethyl-17β-myristoyloxy-gon-4-en-3-one treat 13β-ethyl-17β-hydroxy-gon-4-en-3-one with myristoyl chloride according to the manipulative procedure described above.

To prepare 13β-ethyl-17β-palmitoyloxy-gon-4-en-3-one treat 13β-ethyl-17β-hydroxy-gon-4-en-3-one with palmitoyl chloride according to the manipulative procedure described above.

To prepare 13β-ethyl-17β-oleoyloxy-gon-4-en-3-one treat 13β-ethyl-17β-hydroxy-gon-4-en-3-one with oleoyl chloride according to the manipulative procedure described above.

To prepare 13β-ethyl-17β-cyclohexylacetoxy-gon-4-en-3-one treat 13β-ethyl-17β-hydroxy-gon-4-en-3-one with cyclohexylacetyl chloride according to the manipulative procedure described above.

To prepare 13β-ethyl-17β-2-phenylpropionoxy-gon-4-en-3-one treat 13β-ethyl-17β-hydroxy-gon-4-en-3-one with 2-phenylpropionyl chloride according to the manipulative procedure described above.

EXAMPLE 151

13β-Ethyl-17β-isovaleroyloxy-gon-4-en-3-one

Keep 13β-ethyl-17β-hydroxy-gon-4-en-3-one (6 g.) with isovaleroyl chloride (7.2 g.) in pyridine at room temperature for 20 hours. Add aqueous sodium bicarbonate and extract the product with ether. Wash, dry and evaporate the extracts and purify the residue by chromatography upon neutral alumina. Distill at 200°–230°/.01 mm. and crystallize from hexane to obtain the title compound, m.p. 82°–89°; ultraviolet absorption peak at 240 mμ (ε15,650); infrared absorption peaks at 5.76, 5.99, 6.18 μ.

$C_{24}H_{36}O_3$ Calculated: C, 77.4%; H, 9.7%. Found: C, 77.1%; H, 9.7%.

This compound has androgenic and anabolic activity and is useful as an intermediate for preparing the hormonal compounds of this invention.

EXAMPLE 152

13β-Ethyl-17β-decanoyloxy-gon-4-en-3-one

Add decanoyl chloride (1.9 g.) to 13β-ethyl-17β-hydroxy-gon-4-en-3-one (1.3 g.) in pyridine (12.5 cc.) and allow the mixture to stand at room temperature overnight. Pour the mixture in 2N hydrochloric acid and extract with ether. Wash, dry and evaporate the extracts and recrystallize the residue from benzene-hexane to give the title compound (1.0 g.), m.p. 97°–97.5°; ultraviolet absorption peak at 239 mμ (ε16,500); infrared absorption peaks at 5.74, 5.99, 6.17 μ.

$C_{29}H_{46}O_3$ Calculated: C, 78.7%; H, 10.5%. Found: C, 78.7%; H. 10.5%.

This compound has anabolic and androgenic activity and is useful as an intermediate for preparing the hormonal compounds of this invention.

EXAMPLE 153

13β-Ethyl-17β-(undec-10-enoyloxy)-gon-4-en-3-one

Add undec-10-enoyl chloride (2 g.) in benzene (6 cc.) to 13β-ethyl-17β-hydroxy-gon-4-en-3-one (2 g.) in pyridine (6 cc.) at −15°. Keep the mixture at −10° for 17 hours, add to water and extract with benzene. Wash, dry and evaporate the extracts and recrystallize the residue from methanol to obtain the title compound, m.p. 87°–88°; ultraviolet absorption peak at 240 mμ (ε17,000); infrared absorption peaks at 5.79, 6.00, 6.20 μ.

$C_{30}H_{46}O_3$ Calculated: C, 79.2%; H, 10.2%. Found: C, 79.0%; H, 10.0%.

This compound has anabolic and androgenic activity and is useful as an intermediate for preparing the hormonal compounds of this invention.

EXAMPLE 154

13β-Ethyl-17β-(3-cyclopentylpropionoxy)-gon-4-en-3-one

Add 3-cyclopentylpropionyl chloride (2 g.) in benzene (6 cc.) to 13β-ethyl-17β-hydroxy-gon-4-en-3-one (2 g.) in pyridine (6 cc.) at −15°. Keep the mixture at −10° for 17 hours, work up and recrystallize the product from methanol to give the title compound, m.p. 88°–89°; ultraviolet absorption peak at 241 mμ (ε17,000); infrared absorption peaks at 5.80, 6.00, 6.18 μ.

$C_{27}H_{39}O_3$ Calculated: C, 78.8%; H, 9.55%. Found: C, 78.5%; H, 9.65%.

This compound has anabolic and androgenic activity and is useful as an intermediate for preparing the hormonal compounds of this invention.

EXAMPLE 155

13β-Ethyl-17β-hemisuccinoyloxy-gon-4-en-3-one

Reflux 13β-ethyl-17β-hydroxy-gon-4-en-3-one (1.5 g.) with succinic anhydride (1.0 g.) in pyridine (10 cc.) for 2 hours. Cool the mixture and pour into an excess of 4N hydrochloric acid and extract the mixture with ether-chloroform. Wash the extract with 2N HCl, dilute with ether and exhaustively extract with aqueous sodium bicarbonate. Acidify the bicarbonate extracts and extract the product with chloroform. Recrystallize it twice from chloroform-ether to obtain the title compound, (0.8 g.), m.p. 179°–182°; ultraviolet absorption peak at 239 mμ (ε15,600); infrared absorption peaks at 5.81, 6.02, 8.13 μ.

$C_{23}H_{32}O_5$ Calculated: C, 71.1%; H, 8.3%. Found: C, 71.0%; H, 8.2%.

This compound has anabolic and androgenic activity and is useful as an intermediate for preparing the hormonal compounds of this invention.

EXAMPLE 156

13β-Ethyl-17β-benzoyloxy-gon-4-en-3-one

Treat 13β-ethyl-17β-hydroxy-gon-4-en-3-one (2 g.) in pyridine (20 cc.) with benzoyl chloride (3 cc.) in benzene (10 cc.) at −10°. Keep the mixture at that temperature for 18 hours and then pour into 2N hydrochloric acid (200 cc.). Extract the product with ether and wash, dry and evaporate the extracts. Triturate the residue with a mixture of ether and hexane. Filter the crystalline material obtained and dissolve in benzene and purify by chromatography on neutral alumina. Recrystallize from a mixture of ethyl acetate and hexane to give the title compound, m.p. 141°–9°; ultraviolet light absorption peak at 237 mμ (ε27,300).

$C_{26}H_{32}O_3$ Calculated: C, 79.55%; H, 8.2%. Found: C, 79.3%; H, 8.0%.

This compound has anabolic and androgenic activity and is useful as an intermediate for preparing the hormonal compounds of this invention.

EXAMPLE 157

17β-Ethyl-17β-phenylacetoxy-gon-4-en-3-one

Add phenylacetyl chloride (1.5 cc.) in benzene (4.5 cc.) to 13,3-ethyl-17β-hydroxy-gon-4-en-3-one (1.5 g.) in pyridine (5 cc.) at −18°. Keep the mixture at −10° for 16 hours, add ice-water and extract the product with ether. Wash, dry and evaporate the extracts to a residue and chromatograph on neutral alumina to obtain a crystalline product and recrystalize from methanol to obtain the title compound, m.p. 143°–145°; ultraviolet absorption peak at 240 mμ (ε16,300); infrared absorption peaks at 5.75, 6.00 μ.

This compound has androgenic and anabolic activity and is useful as an intermediate for preparing the hormonal compounds of this invention.

EXAMPLE 158

13β-Ethyl-17β-(3-phenylpropionoxy)-gon-4-en-3-one

Add 13β-ethyl-17β-hydroxy-gon-4-en-3-one (0.11 g.) in dry pyridine (0.35 cc.) at −20° to 3-phenylpropionyl chloride (0.11 g.) in benzene (0.3 cc.). Keep this at −10° for 16 hours, add ice-cold water and extract with a mixture of equal volumes of ether and benzene. Wash the extracts in turn with 2N potassium hydroxide solution, water, 2N hydrochloric acid solution, and brine, and dry. Evaporate solvent to give a residue and recrystallize from a mixture of ether and ethyl acetate to obtain the title compound (0.10 g.), m.p. 135°–40°; infrared absorption peaks at 5.81, 5.99, 8.51, 13.3, 14.3 μ, showing no absorption due to hydroxyl.

This compound has anabolic and androgenic activity and is useful as an intermediate for preparing the hormonal compounds of this invention.

EXAMPLE 159

13β-Ethyl-17β-nicotinoyloxy-gon-4-en-3-one

Reflux 13β-ethyl-17β-hydroxy-gon-4-en-3-one (1 g.) with nicotinic anhydride (2 g.) in pyridine (20 cc.) for 3 hours. Cool, add water, evaporate the mixture to dryness and extract with benzene. Wash, dry and evaporate the extracts to a residue and recrystallize from methanol to obtain the title compound; ultraviolet absorption peak at 239 mμ (ε20,000); infrared absorption peaks at 5.81, 6.00, 6.28 μ.

$C_{25}H_{31}NO_3$ Calculated: C, 76.3%; H, 7.9%; N, 3.6%. Found: C, 76.1%; H, 7.9%; N, 3.7%.

This compound has anabolic and androgenic activity and is useful as an intermediate for preparing the hormonal compounds of this invention.

EXAMPLE 160

13β-Propyl-17β-benzyloxy-gon-4-en-3-one

Esterify 13β-propyl-17β-hydroxy-gon-4-en-3-one (2.5 g.) with benzoyl chloride (2.0 g.). Purify the product by chromatography on Florex and recrystallize from ethyl acetate to obtain the title compound, m.p. 198°–200°; ultraviolet absorption peak at 240 mμ (ε25,000); infrared absorption peaks at 5.84, 6.00 μ.

This compound is useful as an intermediate for preparing the hormonal compounds of this invention.

EXAMPLE 161

13β-Propyl-17β-(3-phenylpropionoxy)-gon-4-en-3-one

Add 3-phenylpropionyl chloride (2.9 g.) in benzene (10 cc.) to 13β-propyl-17β-hydroxy-gon-4-en-3-one (2.5 g.) in pyridine at −10°. Pour the mixture into ice water and extract with benzene-ether. Wash, dry and evaporate the extracts to a gum and purify by chromatography upon Florex. Recrystallize from ethyl acetate-hexane to obtain the title compound, m.p. 104°–108°. Ultraviolet absorption peak at 240 mμ (ε16,000); infrared absorption peaks at 5.76, 6.00 μ.

This compound has anabolic and androgenic activity and is useful as an intermediate for preparing the hormonal compounds of this invention.

EXAMPLE 162

13β-Butyl-17β-(3-phenylpropionoxy)-gon-4-en-3-one

Cool 13β-butyl-17β-hydroxy-gon-4-en-3-one (0.10 g.) in pyridine (0.3 cc.) to −20° and add 3-phenylpropionyl chloride (0.10 g.) in benzene (0.3 cc.). Stir the mixture at −10° for 16 hours, add ice-cold water, ether (15 cc.) and benzene (15 cc.). Separate the organic layers and wash in turn with 2N sodium hydroxide solution, water and brine, and dry. Evaporate the solvent to an uncrystallizable gum, and take up in a little benzene and filter through neutral alumina (5 g.), then wash with more benzene. Evaporate the resulting benzene solution to obtain the title compound as a gum (0.085 g.); infrared absorption peaks at 5.78, 5.99, 13.3, 14.3 μ, with no absorption due to hydroxyl.

This compound has anabolic and androgenic activity and is useful as an intermediate for preparing the hormonal compounds of this invention.

EXAMPLE 163

13β-Isobutyl-17β-(3-phenylpropionoxy)-gon-4-en-3-one

Add 3-phenylpropionyl chloride (.5 g.) in benzene (1.5 cc.) with swirling to 13β-isobutyl-17β-hydroxy-gon-4-en-3-one (.5 g.) in pyridine (2 cc.) at −20°. Store the mixture at −10° for 18 hours, add water and extract the product with ether. Wash, dry and evaporate the extracts to give a residue and recrystallize from methanol to give the title compound, m.p. 101°–106°; ultraviolet absorption peak at 240 mμ (ε15,300); infrared absorption peaks at 5.75, 5.95 μ.

This compound is useful as an intermediate for preparing the hormonal compounds of this invention.

EXAMPLE 164

13β-Ethyl-3,3-ethylenedithio-gon-4-en-17β-ol

Treat 13β-ethyl-17β-hydroxy-gon-4-en-3-one (0.47 g.) in methanol (5 cc.) and ethanedithiol (0.25 cc.) with boron trifluoride etherate (0.25 cc.). Allow the mixture to stand at room temperature for 15 minutes, cool to 0°, filter the precipitate and wash with cold methanol to obtain the title compound, (0.38 g.), m.p. 167°–169°.

$C_{21}H_{32}OS_2$ Calculated: C, 69.2%; H, 8.85%. Found: C, 69.1%; H, 8.9%.

This compound is useful as an intermediate for preparing the hormonal compounds of this invention.

EXAMPLE 165

13β-Methyl-D-homo-17aα-ethynyl-17aβ-hydroxy-gon-4-en-3-one

Add 13β-methyl-D-homo-3-methoxy-17aα-ethynyl-gona-2,5(10)-diene-17aβ-ol (0.7 g.) in dioxane (20 cc.) with stirring to methanol (20 cc.) containing 11N hydrochloric acid (2.8 cc.) and water (1.6 cc.). Stir at room temperature for 2 hours, add water and extract the mixture with ether. Evaporate the washed and dried extracts to give a residue and dissolve in benzene and chromatograph on Florex to obtain the title compound; infrared absorption peaks at 2.97, 3.03, 6.02 μ.

This compound has progestational activity and is useful as an intermediate for preparing the hormonal compounds of this invention.

EXAMPLE 166

13β-Methyl-D-homo-17aα-ethyl-17aβ-hydroxy-gon-4-en-3-one

Add 13β-methyl-D-homo-3-methoxy-17aα-ethyl-gona-2,5(10)-diene-17aβ-ol (0.6 g.) in dioxane (20 cc.) with stirring to methanol (20 cc.) containing 11N hydrochloric acid (2.4 cc.) and water (1.6 cc.). Stir for 2 hours at room temperature, add water and extract the mixture with ether. Wash, dry and evaporate the extracts to give a residue and recrystallize from ethyl acetate to obtain the title compound; ultra violet absorption peak at 240 mμ (ε15,000); infrared absorption peaks at 2.86, 6.01 μ.

This compound has anabolic and androgenic activity and is useful as an intermediate for preparing the hormonal compounds of this invention.

EXAMPLE 167

13β-Ethyl-D-homo-17aα-ethynyl-17aβ-hydroxy-gon-4-en-3-one

Dissolve 13β-ethyl-D-homo-3-methoxy-17aα-ethynyl-gona-2,5(10)-diene-17aβ-ol (3.5 g.) in methanol (180 cc.) containing hydrochloric acid (12 cc.) and water (8 cc.). After 2 hours at room temperature add water and extract the mixture with ether. Wash, dry and evaporate the organic extract and recrystallize the residue from ethyl acetate to obtain the title compound 1.95 g., m.p. 171°–4°. Ultra violet absorption peak at 240 mμ (ε17,400); infrared absorption peaks at 2.99, 3.1, 6.03 μ.

$C_{22}H_{30}O_2$ Calculated: C, 80.94%; H, 9.26%. Found: C, 80.73%; H, 9.35%.

This compound has progestational activity and is useful as an intermediate for preparing the hormonal compounds of this invention.

EXAMPLE 168

13β,17aα-Diethyl-17aβ-hydroxy-D-homo-gon-4-en-3-one

Dissolve 13β,17aα-diethyl-3-methoxy-D-homo-gona-2,5(10)-dien-17aβ-ol (3.5 g.) in methanol (135 cc.) containing water (6 cc.) and hydrochloric acid (9 cc.). Stir the mixture for 1 hour and then pour into brine and extract with ether. Evaporate the washed and dried ether extracts and recrystallize the residue from acetone-hexane to obtain the title compound 2.225 g., m.p. 153°–155°. Ultra violet absorption peak at 240 mμ (ε16,320); infrared absorption peaks at 2.92, 6.03 μ.

$C_{22}H_{34}O_2$ Calculated: C, 79.95%; H, 10.36%. Found: C, 79.93%; H, 10.34%.

This compound has anabolic and androgenic activity and is useful as an intermediate for preparing the hormonal compounds of this invention.

EXAMPLE 169

13β-Ethyl-17α-methyl-17β-hydroxy-gon-4-en-3-one

Heat a solution of 13β-ethyl-3-methoxy-17α-methyl-gona-2,5(10)-dien-17β-ol (0.5 g.) in methanol (55 cc.) under nitrogen to boiling and add 3N hydrochloric acid (0.6 cc.). Allow the solution to cool to room temperature and keep under nitrogen for 3 hours; then add water and extract the mixture with ether. Evaporate the washed and dried extracts and recrystallize the residue from a mixture of ether and hexane, and subsequently from benzene, to yield the title compound as a benzene solvate. Remove the benzene by drying at 100° for 7 hours to obtain the free compound (0.2 g.), m.p. 128°–9°. Ultraviolet absorption peak at 240 mμ (ε16,200). Infrared absorption peaks at 2.95, 6.01 μ.

This compound has anabolic and androgenic activity and is useful as an intermediate for preparing the hormonal compounds of this invention.

EXAMPLE 170

13β-Ethyl-17α-ethynyl-17β-hydroxy-gon-4-en-3-one

To 13β-ethyl-3-methoxy-17α-ethynyl-gona-2,5(10)-dien-17β-ol (0.7 g.) in methanol (36 cc.) add water (1.6 cc.) and concentrated hydrochloric acid (2.4 cc.). After standing at room temperature for 2 hours, add ether and evaporate the washed and dried ethereal solution to yield a gum. Dissolve the gum in benzene (5 cc.) and absorb the solution on an activated Fuller's earth (50 g.). Elute with light petroleum containing increasing proportions of benzene to yield a crystalline by-product; then elute with benzene containing a small proportion of ether to yield a crystalline product. Recrystallise the latter from ethyl acetate, to obtain the title compound (0.11 g.), m.p. 203°–6°; infrared absorption peaks at 2.97, 3.03, 6.02 μ.

This compound has progestational activity and is useful as an intermediate for preparing the hormonal compounds of this invention.

EXAMPLE 171

13β-Ethyl-17α-vinyl-17β-hydroxy-gon-4-en-3-one

Shake 13β-ethyl-17α-ethynyl-17β-hydroxy-gon-4-en-3-one (0.5 g.) in pyridine (20 cc.) containing a 2% palladium-calcium carbonate catalyst (150 mg.) with hydrogen at atmospheric pressure until one molecular equivalent of hydrogen has been absorbed. Recrystallise the product twice from ether-hexane and dry for 4 hours at 65°/.005 mm. to yield the title compound, m.p. 108°–111°; ultraviolet absorption peak at 240 (ε15,200); infrared absorption peak at 10.9μ.

$C_{21}H_{30}O_2$ Calculated: C, 80.2%; H, 9.6%. Found: C, 80.4%; H, 9.7%.

This compound has anabolic and androgenic activity and is useful as an intermediate for preparing the hormonal compounds of this invention.

EXAMPLE 172

13β,17α-Diethyl-17β-hydroxy-gon-4-en-3-one

Add 13β,17α-diethyl-3-methoxy-gona-2,5(10)-dien-17β-ol (0.29 g.) to 15 cc. of a solution prepared by mixing concentrated hydrochloric acid (2.4 cc.), water (1.6 cc.) and methanol (36 cc.). Shake the mixture for 10 minutes, during which time the solid dissolves. After 2 hours pour the solution into water (50 cc.) and extract the mixture with ether. Wash, dry and evaporate the extracts and recrystallise the residue (0.255 g.) from a mixture of ethyl acetate and light petroleum, to yield the title compound (0.196 g.), m.p. 139°–41°. Ultraviolet absorption peak at 240 mµ (ε15,000). Infrared absorption peaks at 2.86, 6.01 µ.

This compound has anabolic and androgenic activity and is useful as an intermediate for preparing the hormonal compounds of this invention.

EXAMPLE 173

13β-Ethyl-17α-propynyl-17β-hydroxy-gon-4-en-3-one

Suspend 13β-ethyl-3-methoxy-17α-propynyl-gona-2,5(10)-dien-17β-ol in methanol (36 cc.) and stir with concentrated hydrochloric acid (2.4 cc.), water (1.6 cc.) and dioxane (10 cc.) until dissolution is complete, and then for a further 20 minutes. Precipitate the product by the addition of water, filter, wash and dry. Recrystallise from ethyl acetate-hexane to yield the title compound, m.p. 124°–5°; infrared absorption peaks at 3.03, 4.55, 6.02 µ; ultraviolet absorption peak at 240 mµ (ε15,600).

This compound has progestational activity and is useful as an intermediate for preparing the hormonal compounds of this invention.

EXAMPLE 174

13β-Ethyl-17α-(2-propenyl)-17β-hydroxy-gon-4-en-3-one

Suspend 13β-ethyl-3-methoxy-17α-(2-propenyl)-gona-2,5(10)-dien-17β-ol in methanol (72 cc.), concentrated hydrochloric acid (4.8 cc.) and water (3.2 cc.) in an atmosphere of nitrogen. Add dioxane (20 cc.) and stir the mixture until dissolution is complete, and then for a further 20 minutes. Add water and extract the mixture with ether. Wash the ethereal solution with saturated sodium bicarbonate solution and water, and dry. Evaporate the solvent to obtain the title compound; infrared absorption peaks at 2.94, 6.02, 6.19 µ. Ultraviolet absorption peak at 240 mµ (ε15,600).

This compound has progestational activity and is useful as an intermediate for preparing the hormonal compounds of this invention.

EXAMPLE 175

13β-Ethyl-17α-n-propyl-17β-hydroxy-gon-4-en-3-one

Keep a solution of 13β-ethyl-3-methoxy-17α-n-propyl-gona-2,5(10)-dien-17β-ol (0.53 g.) in a mixture of methanol (22.5 cc.), 12N hydrochloric acid (1.5 cc.), and water (1.5 cc.) under nitrogen for 2½ hours at room temperature. Then add ice-water (75 cc.), filter off the precipitated solid and dissolve in ether (50 cc.); wash, dry and evaporate the ether solution, to yield a solid residue. Recrystallise the residue repeatedly from ethyl acetate, to obtain the title compound (0.23 g.), m.p. 132°–4.5°. Ultraviolet absorption peak at 240 mµ (ε15,900); infrared absorption peaks at 2.92, 6.02, 6.18 µ.

C₇₉H₃₄O₂ Calculated: C, 79.5%; H, 10.4%. Found: C, 79.8%; H, 10.2%.

This compound has anabolic and androgenic activity and is useful as an intermediate for preparing the hormonal compounds of this invention.

EXAMPLE 176

13β-Ethyl-17α-(2-isobutenyl)-17β-hydroxy-gon-4-en-3-one

Suspend 13β-ethyl-3-methoxy-17α-(2-isobutenyl)-gona-2,5(10)-dien-17β-ol (1.5 g.) in methanol (36 cc.), concentrated hydrochloric acid (2.4 cc.), water (1.6 cc.) and dioxane (10 cc.). When the material has dissolved, add water, filter the precipitate and again stir with methanol (36 cc.), concentrated hydrochloric acid (2.4 cc.) and water (1.66 cc.) for 20 minutes. Then gradually add water and filter the precipitate; wash with water, dry and crystallise from ethyl acetate-hexane and then from acetonitrile to yield the title compound (2 g.); infrared absorption peaks at 2.90, 6.01, 6.20, 11.3 µ; ultraviolet absorption peak at 240 mµ (ε16,800).

This compound has estrogen antagonistic activity and is useful as an intermediate for preparing the hormonal compounds of this invention.

EXAMPLE 177

13β-n-Propyl-17α-methyl-17β-hydroxy-gon-4-en-3-one

Shake 13β-n-propyl-3-methoxy-17α-methyl-gona-2,5(10)-dien-17β-ol (1.0 g.) with 44 cc. of an aqueous methanolic hydrochloric acid solution and stir for 2 hours; then pour the product into water and work up with ether. Purify by chromatography on silica gel (elute with ether), and recrystallise from a mixture of ethyl acetate and hexane to obtain the title compound (0.35 g.), m.p. 134°–5.5°; ultraviolet absorption peak at 240 mµ (ε18,100); infrared absorption peak at 6.02 µ.

This compound has anabolic and androgenic activity and is useful as an intermediate for preparing the hormonal compounds of this invention.

EXAMPLE 178

13β-n-Propyl-17α-ethynyl-17β-hydroxy-gon-4-en-3-one

Shake 13β-n-propyl-3-methoxy-17α-ethynyl-gona-2,5(10)-dien-17β-ol (0.31 g.) with a solution prepared by mixing concentrated hydrochloric acid (0.81 cc.), water (0.54 cc.) and methanol (12.15 cc.), until the solid dissolves. After addition of water, work up with ether, purify by recrystallization from cyclohexane to obtain the title compound (0.1 g.), m.p. 149°–50.5°; ultraviolet absorption peak at 240 mµ (ε15,700); infrared absorption peaks at 2.99, 3.06, 6.04, 6.16 µ.

C₂₂H₃₀O₂ Calculated: C, 80.9%; H, 9.3%. Found: C, 81.0%; H, 9.31%.

This compound has progestational activity and is useful as an intermediate for preparing the hormonal compounds of this invention.

EXAMPLE 179

13β-n-Propyl-17α-vinyl-17β-hydroxy-gon-4-en-3-one

Hydrogenate 13β-n-propyl-17α-ethynyl-17β-hydroxy-gon-4-en-3-one (0.5 g.) to yield the title compound (.425 g.), m.p. 94°–97°; ultraviolet absorption peak at 240 mµ (ε15,600); infrared absorption peak at 10.9 µ.

$C_{22}H_{32}O_2$ Calculated: C, 80.4%; H, 9.8%; Found: C, 81.1%; H, 9.9%.

This compound has anabolic and androgenic activity and is useful as an intermediate for preparing the hormonal compounds of this invention.

EXAMPLE 180

13β-n-Propyl-17α-ethyl-17β-hydroxy-gon-4-en-3-one

Stir a mixture of 13β-n-propyl-3-methoxy-17α-ethyl-gona-2,5(10)-dien-17β-ol (0.8 g.) in tetrahydrofuran (20 cc.), methanol (50 cc.), 12N hydrochloric acid (3.3 cc.) and water (2.2 cc.) at room temperature for 2½ hours and then pour into sodium chloride solution; extract the mixture with ether and wash, dry and evaporate the extracts. Dissolve the crystalline residue obtained (0.8 g.) in a mixture (25 cc.) of equal volumes of benzene and hexane and chromatograph on silica gel; elute with a mixture of equal volumes of benzene and chloroform to yield a crystalline material. Recrystallise this product from a mixture of benzene and light petroleum, to give a benzene solvate, m.p. 93°–5°; and then recrystallise this material from a mixture of hexane and ethyl acetate to obtain the solvent free product, 13β-n-propyl-17α-ethyl-17β-hydroxy-gon-4-en-3-one (0.2 g.), m.p. 98°–100°; ultraviolet absorption peak at 240 mμ (ε15,700); infrared absorption peaks at 2.92, 6.02, 6.18 μ.

This compound has anabolic and androgenic activity and is useful as an intermediate for preparing the hormonal compounds of this invention.

EXAMPLE 181

13β-n-Propyl-17α-propynyl-17β-hydroxy-gon-4-en-3-one

Stir 13β-n-propyl-3-methoxy-17α-propynyl-gona-2,5(10)-dien-17β-ol (2.5 g.) under nitrogen with methanol (135 cc.) containing 11N hydrochloric acid (9 cc.) and water (6 cc.). After two hours add isopropyl alcohol (35 cc.) and continue stirring for a further 30 minutes. Add the mixture to brine and extract the product with ether. Evaporate the washed and dry extracts to a glass, dissolve in benzene and chromatograph on Florex. Elute with benzene containing 5% ether and recrystallise the product so obtained from ethyl acetate-hexane to yield the title compound, m.p. 182–184°; ultraviolet absorption peak at 240 mμ (ε16,700).

$C_{23}H_{32}O_2$ Calculated: C, 81.1%; H, 9.5%. Found: C, 80.95%; H, 9.4%

This compound has progestational and estrogen antagonistic activity and is useful as an intermediate for preparing the hormonal compounds of this invention.

EXAMPLE 182

13β-n-Propyl-17α-allyl-17β-hydroxy-gon-4-en-3-one

Stir 13β-n-propyl-3-methoxy-17α-allyl-gona-2,5(10)-dien-17β-ol (0.77 g.) under nitrogen in isopropyl alcohol (25 cc.) containing 11N hydrochloric acid (2.5 cc.) and water (1.6 cc.) for 2.5 hours. Filter the mixture, add to brine and extract the product with ether. Evaporate the washed and dry extracts and purify the residue by chromatography on Florex and by recrystallisation from ethyl acetate to obtain the title compound, m.p. 135°–137°; ultraviolet absorption peak at 241.5 mμ (ε17,500); infrared absorption peaks at 2.95, 6.02, 6.18 μ.

$C_{23}H_{34}O_2$ Calculated: C, 80.65%; H, 10.0%. Found: C, 80.4%; H, 9.8%.

This compound has progestational anabolic and androgenic activity and is useful as an intermediate for preparing the hormonal compounds of this invention.

EXAMPLE 183

13β,17α-Di-n-propyl-17β-hydroxy-gon-4-en-3-one

Stir 13β,17α-di-n-propyl-3-methoxy-gona-2,5(10)-dien-17β-ol (1.07 g.) under nitrogen in methanol (50 cc.) containing water (2.5 cc.) and 11N hydrochloric acid (3.5 cc.) at room temperature for 2 hours. Then add water and extract the product with ether. Evaporate the washed and dry extracts and purify the residue by chromatography on alumina, by repeated recrystallization from ethyl acetate, and by sublimation at 145°/.003 mm. to obtain the title compound, (.34 g.), m.p. 147°–49°. Ultraviolet absorption peak at 241.5 mμ (ε16,600); infrared absorption peaks at 2.91, 6.02, 6.19 μ.

This compound has anabolic and androgenic activity and is useful as an intermediate for preparing the hormonal compounds of this invention.

EXAMPLE 184

13β-n-Propyl-17α-(1-methallyl)-17β-hydroxy-gon-4-en-3-one

Stir 13β-n-propyl-3-methoxy-17α-(1-methallyl)-gona-2,5(10)-dien-17β-ol (1.5 g.) under nitrogen with methanol (90 cc.) containing 11N hydrochloric acid (9 cc.) and water (6 cc.). Add the mixture to brine and extract the product with ether. Evaporate the washed and dried extracts to yield the title compound; ultraviolet absorption peak at 240 mμ (ε13,500); infrared absorption peak at 11.0 μ.

This compound has progestational activity and is useful as an intermediate for preparing the hormonal compounds of this invention.

EXAMPLE 185

13β-n-Propyl-17α-(2-methallyl)-17β-hydroxy-gon-4-en-3-one

Employ the method of Example 184 to hydrolyse 13β-n-propyl-3-methoxy-17α-(2-methallyl)-gona-2,5(10)-dien-17β-ol. Purify the product by chromatography on Florex and recrystallisation from ethyl acetate to afford the title compound, m.p. 141.5°–143.5°; ultraviolet absorption peak at 241 mμ (ε16,700); infrared absorption peaks at 2.87, 6.01, 6.18 μ.

$C_{24}H_{36}O_2$ Calculated: C, 80.85%; H, 10.2%. Found: C, 80.8%, H, 9.9%.

This compound has progestational activity and is useful as an intermediate for preparing the hormonal compounds of this invention.

EXAMPLE 186

13β-n-Butyl-17α-ethynyl-17β-hydroxy-gon-4-en-3-one

Hydrolyse 13β-n-butyl-3-methoxy-17α-ethynyl-gona-2,5(10)-dien-17β-ol (2 g.) by the method of Example 184 and purify the product by chromatography on Florex and by recrystallization from ether-hexane to afford the title compound (.71 g.), m.p. 159°–163°; ultraviolet absorption peak at 240 mμ (ε15,900); infrared absorption peaks at 6.00 μ.

$C_{23}H_{32}O_2$ Calculated: C, 81.1%; H, 9.5%. Found: C, 80.8%; H, 9.3%.

The compound has progestational activity and is useful as an intermediate for preparing the hormonal compounds of this invention.

EXAMPLE 187

13β-n-Butyl-17α-ethyl-17β-hydroxy-gon-4-en-3-one

Keep a solution of 13β-n-butyl-3-methoxy-17α-ethylgona-2,5(10)-dien-17β-ol (1.05 g.) in a mixture of tetrahydrofuran (15 cc.), methanol (54 cc.), 12N hydrochloric acid (3.6 cc.) and water (2.4 cc.) for 2 hours at room temperature and then pour into brine (350 cc.). Work up with ether and dissolve the product, a gum (1.0 g.), in a mixture of light petroleum and benzene (25 cc.) and chromatograph on silica gel. Elute with benzene containing a small proportion of ether to give a crystalline by-product (0.1 g.); subsequently elute with a mixture of ether, benzene and chloroform (in the proportions 5:4:1 by volume) to yield a crystalline product. Recrystallize the latter from hexane, and subsequently from hexane containing a little ethyl acetate to obtain the title compound (0.23 g.), m.p. 78°–80°; ultraviolet absorption peak at 240 mμ (ε14,700); infrared absorption peaks at 2.88, 6.00, 6.18 μ.

This compound has anabolic, androgenic and estrogen antagonistic activity and is useful as an intermediate for preparing the hormonal compounds of this invention.

EXAMPLE 188

13β,17α-Diethyl-17β-hydroxy-gon-4-en-3-one

Treat 13β,17α-diethyl-17β-hydroxy-gon-5(10)-en-3-one (12.2 g.) with a solution of methanol (442 cc.), water (22 cc.) and concentrated hydrochloric acid (30 cc.) and allow the mixture to stand at room temperature for 2 hours. Precipitate the product by the addition of water, extract the reaction mixture with ether and wash the ethereal solution with 10% aqueous sodium carbonate, brine and dry ($MgSO_4$). Evaporate the solvent and recrystallize the residue from acetonitrile to give the title compound 7.9 g. (64.8%), m.p. 144°–5°; infrared absorption 2.92, 6.0, 6.2 μ; ultraviolet absorption λmax. 240 mμ (ε15,680).

$C_{21}H_{32}O_3$ Calculated: C, 79.86%; H, 10.04%. Found: C, 79.70%; H, 10.19%.

This compound has anabolic and androgenic activity and is useful as an intermediate for preparing the hormonal compounds of this invention.

EXAMPLE 189

13β-Ethyl-17α-ethynyl-17β-hydroxy-gon-4-en-3-one

Stir 13β-ethyl-17α-ethynyl-17β-hydroxy-gon-5(10)-en-3-one (0.1 g.) with a mixture of methanol (36 cc.), water (1.6 cc.) and concentrated hydrochloric acid (2.4 cc.) for 1 hour. Add water and extract the mixture with ether. Wash, dry and evaporate the ethereal solution and recrystallize the residue from ether-hexane to obtain the title compound, m.p. 203°–6° undepressed on admixture with authentic material. Infrared spectrum 3.05, 3.5, 6.05, 9.4 μ.

This compound has progestational activity and is useful as an intermediate for preparing the hormonal compounds of this invention.

EXAMPLE 190

13β,17α-Diethyl-17β-hydroxy-gon-4-en-3-one

Add 13β-ethyl-17α-ethynyl-17β-hydroxy-gon-4-en-3-one (1 g.) in benzene (15 cc.) and ethanol (5 cc.) to a pre-reduced suspension of 2% palladium on calcium carbonate (0.3 g.) in benzene (10 cc.) and shake the mixture in an atmosphere of hydrogen until 163 cc. (2.1 moles) of hydrogen has been absorbed. Filter off the catalyst, evaporate the solvent and shake the product (0.55 g.) in methanol (10 cc.) with a solution of sodium metabisulphite (1.7 g.) in water (8 cc.) for 5 minutes. Add water, extract the mixture with ether; wash, dry and evaporate the ethereal solution and recrystallize the product from acetone to obtain the title compound (0.4 g.), m.p. 144° undepressed on admixture with authentic material; infrared spectrum 2.9, 6.0, 6.18; ultraviolet spectrum max. 241 mμ (ε17,250).

This compound has anabolic and androgenic activity and is useful as an intermediate for preparing the hormonal compounds of this invention.

EXAMPLE 191

17β-Ethyl-17α-ethynyl-17β-hydroxy-gon-4-en-3-one

Treat 13β-ethyl-3-ethoxy-17α-ethynyl-gona-3,5-dien-17β-ol (0.1 g.) with a mixture of methanol (10 cc.) and 50% hydrochloric acid (1 cc.) and allow the mixture to stand at room temperature for 1 hour. Add water, filter off the precipitated product and recrystallize from ethyl acetate-hexane to yield the title compound, identical with authentic material by mixed melting point determination and comparison of infrared spectra.

This compound has progestational activity and is useful as an intermediate for preparing the hormonal compounds of this invention.

EXAMPLE 192

13β, 17α-Diethyl-17β-hydroxy-gonan-3-one

Dissolve 13β-ethyl-17α-ethynyl-17β-hydroxy-gon-4-en-3-one (1.5 g.) in ethanol (50 cc.) and shake with 10% palladium on charcoal (0.9 g.) in an atmosphere of hydrogen until uptake of hydrogen ceases. Filter off the catalyst, evaporate the solvent and recrystallize the residue from etherhexane to afford title compound, m.p. 192°–196°.

$C_{21}H_{34}O_2$ Calculated: C, 79.19%; H, 10.76%. Found: C, 79.4%; H, 10.43%.

This compound has estrogen antogonistic activity and is useful as an intermediate for preparing the hormonal compounds of this invention.

EXAMPLE 193

13β-Ethyl-3-methoxy-17α-ethynyl-17β-acetoxy-gona-1,3,5(10)-triene

Shake 13β-ethyl-3-methoxy-17α-ethynyl-gona-1,3,5(10)-trien-17β-ol (1.1 g.) with toluene-p-sulphonic acid (0.3 g.) and acetic anhydride (10 cc.) until the solution is homogeneous and then allow to stand at room temperature for 12 hours. Decompose the reaction mixture by stirring with water containing a little pyridine and extract with ether. Wash the ethereal solution with water, 2N aqueous sodium hydroxide, water, dilute hydrochloric acid, brine and dry ($MgSO_4$). Evaporate the solvent and dissolve the crystalline residue in benzene and filter through a short column of alumina. Recrystallize the product from methanol-ethyl acetate to obtain the title compound 0.98 g., m.p. 178°–182°; infrared absorption peaks at 3.02, 5.75 μ.

This compound has estrogenic activity and is useful as an intermediate for preparing the hormonal compounds of this invention.

EXAMPLE 194

13β-Ethyl-3-methoxy-17α-dibromoacetyl-17β-acetoxy-gona-1,3,5(10)-triene

Dissolve 13β-ethyl-3-methoxy-17α-ethynyl-17β-acetoxy-gona-1,3,5(10)-triene (0.6 g.) in tertiary butanol (25 cc.) and water (0.4 cc.) and add N-bromoacetamide (0.55 g.). Allow the mixture to stand for 15 hours, then add water (10 cc.), cool to 0° and allow to stand for 3 hours. Filter the precipitated product, wash with aqueous methanol and dry to obtain the title product (0.72 g.), m.p. 85°–92°.

This compound is useful as an intermediate for preparing the hormonal compounds of this invention.

EXAMPLE 195

13β-Ethyl-3-methoxy-17α-acetyl-17β-acetoxy-gona-1,3,5(10)-triene

Heat 13β-ethyl-3-methoxy-17α-dibromoacetyl-17β-acetoxy-gona-1,3,5(10)-triene (0.7 g.) in acetic acid (27 cc.) and water (2.7 cc.) with sodium acetate (0.7 g.) and zinc dust (0.99 g.) at 100° for 15 minutes with stirring. Filter the mixture, add water to the filtrate and filter the precipitated product. Dry the residue and recrystallize from ethyl acetate-methanol to obtain the title product (0.25 g.), m.p. 144°–8°; infrared absorption peaks at 5.8, 5.9 μ.

This compound is useful as in intermediate for preparing the hormonal compounds of this invention.

EXAMPLE 196

13β-Ethyl-17β-acetylgon-4-en-3-one

Add 13β-ethyl-3-methoxy-17α-acetyl-17β-acetoxy-gona-1,3,5(10)triene (0.24 g.) in dioxan (5 cc.) to a stirred solution of lithium (0.15 g.) in liquid ammonia (100 cc.). After 30 minutes add methanol (8 cc.) followed by lithium (0.5 g.) in small pieces. Add water, extract with ether and work up to a gum (0.218 g.). Reflux this product with 4N hydrochloric acid (5 cc.) and methanol (8 cc.) for 15 minutes. Add water, extract with ether, work up and dissolve the resulting gum in acetone (30 cc.) containing anhydrous magnesium sulphate (0.5 g.) and add 8N-chromic acid dropwise with swirling until the solution assumes a permanent yellowish-orange color. Add excess isopropanol and evaporate the solution almost to dryness. Add water, extract with ether, wash, dry and evaporate the organic solution, filter the product through alumina with benzene-ether and recrystallize the product from ethyl acetate to obtain the title product (0.072 g.), m.p. 138°–142°; infrared absorption peaks at 5.9, 6 μ.

This compound has progestational activity and is useful as an intermediate for preparing the hormonal compounds of this invention.

EXAMPLE 197

13β-Ethyl-gon-4-en-17β-ol

Add 13β-ethyl-3,3-ethylenedithio gon-4-en-17β-ol in ether (5 cc.) and tetrahydrofuran (2 cc. to a stirred solution of liquid ammonia (50 cc.) and add sodium (0.5 g.) in pieces and then add ethanol dropwise to discharge the blue color. Add ammonium chloride and water, extract with ether and wash, dry and evaporate the organic solution. Recrystallize the residue from light petroleum, b.p. 60°–80°, to obtain 13β-ethyl-gon-4-en-17β-ol, m.p. 118°–120°.

This compound has anabolic and androgenic activity and is useful as an intermediate for preparing the hormonal compounds of this invention.

EXAMPLE 198

13β-Ethyl-gon-4-en-17-one

Dissolve 13β-ethyl-gon-4-en-17β-ol (0.29 g.) in acetone (40 cc.) and 8N-chromic acid dropwise with stirring until the solution becomes permanently orange and then add isopropanol (3 cc.) and evaporate the solution to small bulk (ca. 5 cc.). Add water and extract the mixture with ether. Wash, dry and evaporate the ethereal solution to obtain 13β-ethyl-gon-4-en-17-one (0.24 g.), m.p. 101°–102° C. Purify by recrystallization from methanol to obtain the pure product, m.p. 102.5°–103.5° C.

$C_{19}H_{28}O$ Calculated: 83.8%; H, 10.4%. Found: 83.55%; H, 10.7%.

This compound is useful as an intermediate for preparing the hormonal compounds of this invention.

EXAMPLE 199

13β-Ethyl-17α-allyl-gon-4-en-17β-ol

Reflux magnesium (0.36 g.) and allyl bromide (0.15 cc.) in dry ether (10 cc.) for 15 minutes and then add 13β-ethyl-gon-4-en-17-one (0.9 g.) in ether (40 cc.) containing allyl bromide (2.9 cc.). Reflux the mixture for 3 hours and treat the cooled solution with aqueous ammonium chloride. Extract the product with ether and wash the ethereal solution with water, brine and dry (MgSO$_4$). Evaporate the solvent and recrystallize the residue from methanol to obtain 13β-ethyl-17α-allyl-gon-4-en-17β-ol (0.97 g.), m.p. 88.5°–91° C. Recrystallize further from ether-hexane to obtain the pure product, m.p. 92°–94°C.

$C_{22}H_{34}O$ Calculated: C, 84.0%; H, 10.9%. Found: C, 84.4%; H, 10.9%.

This compound has progestational activity and is useful as an intermediate for preparing the hormonal compounds of this invention.

EXAMPLE 200

13β-n-Propyl-3,3-ethylenedithio-gon-4-en-17β-ol

Treat 13β-n-propyl-17β-hydroxy-gon-4-en-3-one (6 g.) in acetic acid (15 cc.) with ethane dithiol (1.75 cc.) followed by boron trifluoride etherate (1.75 cc.). Allow the mixture to stand at room temperature for 15 minutes then pour into water and filter. Recrystallize the residue from methanol to obtain the title product, (6.05 g.), m.p. 165°–166.5° C. Recrystallize further to obtain the pure compound, m.p. 167°–168.5° C.

$C_{22}H_{34}OS_2$ Calculated: C, 69.8%; H, 9.05%; S, 26.9%. Found: C, 69.6%; H, 8.9%; S, 16.5%.

This compound is useful as an intermediate for preparing the hormonal compounds of this invention.

EXAMPLE 201

13β-n-Propyl-gon-4-en-17β-ol

Add 13β-n-propyl-3,3-ethylenedithio-gon-4-en-17β-ol (5.8 g.) in tetrahydrofuran (40 cc.) and ether (20 cc.) with stirring to a solution of sodium (3 g.) in liquid ammonia (250 cc.). Add more sodium (3 g.) in pieces over 30 minutes followed by the dropwise addition of ethanol to discharge the blue color. Add water, extract with ether and wash, dry and evaporate the organic extracts. Recrystallize the product from ether-hexane to obtain the title product (4.5 g.), m.p. 115°–119° C.

This compound has anabolic and androgenic activity and is useful as an intermediate for preparing the hormonal compounds of this invention.

EXAMPLE 202

13β-n-Propyl-gon-4-en-17-one

Add 8N chromic acid dropwise with stirring to a solution of 13β-n-propyl-gon-4-en-17β-ol in acetone (100 cc.) until the solution becomes permanently orange. Add isopropanol (10 cc.) and potassium carbonate (5 g.), filter and evaporate the filtrate to dryness. Filter the residue in benzene-ether (1:1) through neutral alumina (20 g.), evaporate and recrystallize the product from methanol to obtain 13β-n-propyl-gon-4-en-17-one. Recrystallize from ether-hexane to obtain the pure product, m.p. 89°–90° C.

$C_{20}H_{30}O$ Calculated: C, 83.3; H, 10.6%. Found: C, 83.9; H, 10.5%.

This compound is useful as an intermediate for preparing the hormonal compounds of this invention.

EXAMPLE 203

13β-n-Propyl-17α-ethynyl-gon-4-en-17β-ol

Add 13β-n-propyl-gon-4-en-17-one (1.5 g.) in dimethylacetamide (50 cc.) to a stirred suspension of lithium acetylide (40 cc. of a 15% solution in dioxan-triethylamine) and pass a slow stream of acetylene through the stirred solution for 40 hours. Pour the mixture into iced water and extract with ether. Wash and dry the ethereal solution and evaporate to dryness. Recrystallize the product twice from methanol and once from hexane to obtain the title product, m.p. 118°–119° C.

$C_{22}H_{32}O$ Calculated: C, 84.55%; H, 10.3%. Found: C, 84.8%; H, 10.4%.

This compound has progestational activity and is useful for preparing the hormonal compounds of this invention.

EXAMPLE 204

13β-n-Propyl-17α-allyl-gon-4-en-17β-ol

Reflux magnesium (0.36 g.) and allyl bromide (1.5 cc.) in ether (15 cc.) for 15 minutes and then add a solution of 13β-n-propyl-gon-4-en-17-one in ether (10 cc.) and allyl bromide (2.9 cc.). Reflux for 3 hours and treat the cooled solution with aqueous ammonium chloride. Extract the mixture with ether and wash, dry, and evaporate the ethereal solution. Recrystallize the residue from methanol and then from hexane to obtain 13β-n-propyl-17α-allyl-gon-4-en-17β-ol, m.p. 90°–92° C.

$C_{23}H_{36}O$ Calculated: C, 84.1%; H, 11.1%. Found: C, 84.15%; H, 11.1%.

This compound has progestational activity and is useful as an intermediate for preparing the hormonal compounds of this invention.

EXAMPLE 205

13β,17α-Diethyl-gon-4-en-3,17β-diol

Add 13β,17α-diethyl-17β-hydroxy-gon-4-en-3-one (10 g.) in tetrahydrofuran (100 cc.) and ether (100 cc.) to a stirred suspension of lithium aluminum hydride (5 g.) in ether (1000 cc.). Reflux the mixture for 2 hours, cool and decompose excess reagent by cautiously adding water. Separate the organic phase, wash, dry and evaporate to obtain the title product (10 g.), m.p. 110°–122° C.

This compound has anabolic and androgenic activity and is useful as an intermediate for preparing the hormonal compounds of this invention.

EXAMPLE 206

13β,17α-Diethyl-3-acetoxy-gon-4-en-17β-ol

Allow 13β,17α-diethyl-gon-4-en-3,17β-diol (3 g.) in pyridine (30 cc.) and acetic anhydride (3 cc.) to stand for 12 hours at 0°C. Evaporate the solvents under reduced pressure at less than 50° C. and crystallize the residue from ether-hexane to obtain the title product (2.43 g.), m.p. 85°–100° C.

This compound has anabolic and androgenic activity and is useful as an intermediate for preparing the hormonal compounds of this invention.

EXAMPLE 207

13β,17α-Diethyl-gon-4-en-17β-ol

Add 13β,17α-diethyl-3-acetoxy-gon-4-en-17β-ol (1.35 g.) in ether (50 cc.) to a stirred solution of lithium (0.5 g.) in redistilled ethylamine (100 cc.). Stir the mixture for 15 minutes and decompose excess reagent with sodium nitrite. Allow the ethylamine to evaporate and add sodium sodium sulphate (10 g.) and ether (200 cc.). Evaporate the filtered ethereal solution and recrystallize the residue from ether-hexane to give the title product, m.p. 96°–112° C. Chromatograph on neutral alumina, eluting with benzene containing 5% ether and recrystallize from ether to obtain the pure compound, m.p. 117.5°–118.5° C.

$C_{21}H_{34}O$ Calculated: C, 83.4%; H, 11.3%. Found: C, 83.5%; H, 11.3%.

This compound has anabolic and androgenic activity and is useful as an intermediate for preparing the hormonal compounds of this invention.

EXAMPLE 208 dl-13-Ethyl-17-ethynylgon-4-en-17β-ol

Stir 13-ethylgon-4-en-17-one (2.1 g) with lithium acetylide (4.5 g) in dimethylacetamide (60 ml) for 60 hours. Recrystallize twice from methanol to obtain the title compound (1.13 g), m.p. 106°–108°. Chromatograph on neutral alumina (35 g) and recrystallize from methanol and then from ether-hexane to obtain an analytical sample with m.p. 109°–110°; infrared absorption peaks at 2.8 μ, 3.6 μ.

$C_{21}H_{30}O$ Calculated: C, 84.51%; H, 10.13%. Found: C, 84.43%; H, 9.86%.

This compound has progestational activity.

EXAMPLE 209 dl-17α-Allyl-17-hydroxy-13-propylgon-4-en-3-one

Treat dl-3-methoxy-13-propylgona-2,5(10)-dien-17-one (2.0 g) with allyl magnesium bromide to obtain a glass that is a mixture of dl-17α-allyl-3-methoxy-13-propylgona-2,5(10)-dien-17-ol (minor component) and the $\Delta^{5(10)}$-3-keto and $\Delta^4$-3-keto compounds (major component). Hydrolyze the mixture (in two portions) with hydrochloric acid-isopropanol-water, then chromatograph and crystallize the resultant crude product to obtain the title compound (22% from the starting material), m.p. 135°–137°; ultraviolet absorption peak at 241.5 mµ (ε17,470), infrared maxima at 2.95 µ (OH), 6.03 µ, 6.18 µ (α,β-unsaturated carbonyl), 10.93 µ (R—CH=CH$_2$).

$C_{23}H_{34}O_2$ Calculated: C, 80.65%; H, 10.01%. Found: C, 80.39%; H, 9.77%.

This compound has progestational activity.

EXAMPLE 210 dl-3-(17β-Hydroxy-3-oxo-13-propylgon-4-en-17α-yl)propionic acid, γ-lactone

Add dl-17α-ethynyl-3-methoxy-13-propylgona-1,3,5(10)-trien-17β-ol (8.7 g) in tetrahydrofuran (200 ml) with stirring to 3 moles of ethereal methyl magnesium bromide (100 ml). Stir the mixture, distil until the boiling point of the distillate reaches 63°. Keep the mixture at reflux with stirring for 21 hours and add the cooled mixture with swirling to solid carbon dioxide (ca. 1 kg). After 1.5 hours acidify the mixture with sulfonic acid and extract with ether. Extract the ether solution with aqueous sodium hydrogen carbonate and acidify the extracts to obtain dl-3-(17β-hydroxy-3-methoxy-13-propylgona-1,3,5(10)-trien-17α-yl)prop-2-ynoic acid. Recycle the neutral material to obtain further acid. Hydrogenate this acid (4.3 g) in ethanol (100 cc) containing 5% palladized charcoal (3 g). Add the product (3.05 g), m.p. 183°–191°, to sodium hydroxide (0.32 g) in methanol and evaporate the resulting solution to dryness. Reduce the residue with lithium (5 g) in liquid ammonia (300 cc)-tetrahydrofuran (50 cc)-t-butanol (50 cc). Keep the product at room temperature for two hours in methanol (50 ml)-water (10 ml)-concentrated hydrochloric acid (5 ml). Purify the product by sublimation, chromatography and recrystallization from acetone to obtain the title compound, m.p. 197°–199.5°, λmax. 240.5 mµ (ε16,800); infrared absorption peaks at 5.67, 6.01, and 6.21 µ.

$C_{23}H_{32}O_3$ Calculated: C, 77.5%; H, 9.05%. Found: C, 76.6%; H, 8.95%.

This compound has aldosterone blocking activity.

EXAMPLE 211 dl-17β-Hydroxyestr-4-en-3-one 3-phenylpropionate
(dl-19-Nortestosterone 3-phenylpropionate)

Dissolve dl-17β-hydroxyestr-4-en-3-one (0.3 g) in pyridine (1 ml) cooled to −15°. Allow the mixture to stand at −10° for 15 hours. Pour into water and extract with benzene. Wash the organic extracts successively with 10% aqueous sodium hydroxide, 10% hydrochloric acid, water, and brine. Dry over sodium sulfate and evaporate. Filter the residue through a short column of alumina with benzene and recrystallize from ethyl acetate-light petroleum ether to obtain the title compound, m.p. 120°–122°; ultraviolet absorption peak at 241 mµ (ε16,900), infrared maxima at 5.8 µ, 6.05 µ.

This compound has anabolic activity.

EXAMPLE 212 dl-17α-Chloroethynyl-17-hydroxy-13-propylgon-4-en-3-one

Treat dl-3-methoxy-13-propylgona-2,5(10)-dien-17-one (8.0 g) in ether (250 cc) with chloroethynyl lithium prepared from methyl lithium (5.53%, .35 M) (100 cc) and dichloroethylene (16.9 g, .175 M) in ether. Stir for 20 hours under nitrogen. Wash, dry and evaporate the ether layer. Triturate the residue with hot methanol (225 cc) to obtain dl-3-methoxy-17α-chloroethynyl-17-hydroxy-13-propylgona-2,5(10)-diene (2.5 cc), m.p. 110°–116°, λmax. CHCl$_3$ 4.55, 5.94, 6.04 µ.

Hydrolyze crude dl-3-methoxy-17α-chloroethynyl-17-hydroxy-13-propyl-gona-2,5(10)-diene with water (4 cc), methanol (90.0 cc), HCl (6.0 cc) and isopropanol (10 cc) under nitrogen. Pour into brine and extract with ether. Chromatograph the crude product on Florex (200 g). Elute with 5% ether-95% benzene and recrystallize from ethyl acetatehexane to obtain the title compound (1.10 g), m.p. 179°–181°C; λmax. KBr 2.90, 4.53, 6.03 µ; λmax. EtOH 240 mµ (ε16,900).

$C_{22}H_{32}ClO_2$ Calculated: C, 73.21%; H, 8.10%; Cl, 9.82%. Found: C, 73.51%; H, 8.19%; Cl, 9.9%.

This compound has progestational activity.

EXAMPLE 213 dl-17α-Chloroethynyl-13-ethyl-17-hydroxygon-4-en-3-one

Carry out an Oppenauer oxidation on dl-13-ethyl-3-methoxygona-2,5(10)-dien-17β-ol (70 g) in the usual manner to obtain dl-13-ethyl-3-methoxygona-2,5(10)-dien-17-one (58 g, 83% yield). Combine this material with a further 5.5 g. of dl-13-ethyl-3-methoxygona-2,5(10)-dien-17-one. Prepare a solution of approximately 0.5 mole of lithium chloroacetylide in ether in the following manner. Transfer, under nitrogen, a solution of methyl lithium (23.6 g) in ether (406 g) to a 2-liter, 3-necked flask equipped with dry-ice condenser. Cool in ice to 0°. Add trans-dichloroethylene (60 g) dropwise with stirring. Allow the resultant mixture to come to room temperature before adding the steroid.

Add the enol ether as a slurry in tetrahydrofuran (500 ml) to the solution of lithium chloroacetylide in ether. Stir the steadily darkening solution for 2 hours, then work up by addition of ice water (500 ml), followed by extraction in the usual manner. Evaporate the solvent and triturate the residue with hot methanol to obtain 17α-chloroethynyl-13-ethyl-3-methoxygona-2,5(10)-dien-17β-ol (73 g).

Dissolve 17α-chloroethynyl-13-ethyl-3-methoxygona-2,5(10)-dien-17β-ol (65 g) in the minimum volume of tetrahydrofuran and add to a stirred mixture of methanol (720 ml), concentrated hydrochloric acid (48 ml), and water (32 ml). Stir until all the precipitated material has dissolved. Stir the mixture for a further 30 minutes, when the title compound will begin to crystallize out. Then slowly add water (2 liters) to precipitate the rest of the product, filter off, wash thoroughly with distilled water, and partially dry in a desiccator. Take up the crude material in hot ethyl acetate and charcoal with Norit (30 g). This treatment will remove almost all the color. Evaporate the solvent and crystallize the material from methanol (400 ml) and water (130 ml) to obtain the title compound (54 g); infrared absorption peak at 5.75 μ. Crystallize further from methanol (300 ml) and water (100 ml) to obtain an analytical sample (43 g) with m.p. 186°–189°; ultraviolet absorption peak at 240 mμ (ε16,100); infrared maxima at 3.05 μ, 4.6 μ, 6.05 μ.

$C_{19}H_{27}ClO_2$ Calculated: C, 72.71%; H, 7.85%; Cl, 10.22%. Found: C, 72.75%; H, 7.77%; Cl, 10.20%.

This compound has progestational activity.

EXAMPLE 214 dl-6-Dibromomethylene-13-ethylgon-4-ene-3,17-dione and dl-13-Ethyl-6-methylgon-4-ene-3,17-dione React dl-13-ethyl-3-methoxygona-2,5(10)-dien-17β-ol (50.2 g) according to the Oppenauer oxidation procedure to obtain dl-13-ethyl-3-methoxygona-2,5(10)-dien-17-one, m.p. 126°–143°; no aromatic system shown by ultraviolet absorption, infrared absorption peaks (potassium bromide) at 5.78 μ, 6.09 μ, 6.18 μ.

Treat dl-13-ethyl-3-methoxygona-2,5(10)-dien-17-one with hydrochloric acid in aqueous methanol to obtain dl-13-ethylgon-4-ene-3,17-dione (25.6, 54% from dl-13-ethyl-3-methoxygona-2,5(10)-dien-17β-ol), m.p. 156°–157.5°; ultraviolet absorption peak in 95% ethanol at 240.5 mμ (15,900), infrared maxima (potassium bromide) at 5.77 μ, 5.98 μ. Recrystallize dl-13-ethylgon-4-ene-3,17-dione (1.0 g) three times from ethyl acetate to obtain 484 mg., 157°–159.5°; ultraviolet absorption peak (95% ethanol) at 240 mμ (ε17,200), infrared maxima (potassium bromide) at 5.77 μ, 5.98 μ.

React dl-13-ethylgon-4-ene-3,17-dione (5.0 g) in dioxane with ethyl orthoformate and toluene-p-sulfonic acid at room temperature for 3 hours to obtain 4.12 g. (75%) of dl-3-ethoxy-13-ethylgona-3,5-dien-17-one; ultraviolet absorption peak (95% ethanol) at 242 mμ (ε12,150), infrared absorption peak (potassium bromide) at 5.78 μ.

Stir at room temperature dl-3-ethoxy-13-ethylgona-3,5-diene-17-one (1.88 g) with carbon tetrabromide (4.0 g) in collidine (17.5 ml) and pyridine (2.5 ml) for 40 hours. Filter off the solid and wash with a little pyridine. Acidify the filtrate with cold dilute hydrochloric acid and extract the product into ether. Wash, dry, and concentrate the ethereal solution to approximately 10 ml. Add pyridine (50 ml) and heat at 100° for 30 minutes under nitrogen. Cool and acidify the solution and extract with ether. Evaporate the washed, dried ethereal extracts and crystallize the residue from ether to obtain dl-6-dibromomethylene-13-ethylgon-4-ene-3,17-dione (1.44 g). Purify by chromatography on deactivated alumina (40 g), eluting with benzene-petroleum ether (1:1) to obtain 0.862 g. (29%), m.p. 149°–153°. Recrystallize from tetrahydrofuran-ether to obtain the analytical sample, m.p. 163.5°–165.5°; ultraviolet absorption peaks at 249 mμ (ε10,540), 283–288 mμ (ε6,650); infrared maxima (chloroform) at 5.78 μ, 5.99 μ, 6.21 μ, 6.38 μ.

$C_{20}H_{24}Br_2O_2$ Calculated: C, 52.65%; H, 5.30%; Br, 35.0%. Found: C, 52.85%; H, 5.08%; Br, 32.8%.

Hydrogenate dl-6-dibromomethylene-13-ethylgon-4-ene-3,17-dione for 2 hours in the presence of dioxane and triethylamine, using 2% palladium-strontium carbonate as a catalyst. Filter off the catalyst, acidify the filtrate with 1N hydrochloric acid, and allow to stand for one hour. Extract with ether and triturate with methanol to obtain crystals of starting material (100 mg). Concentrate the liquors to obtain 86 mg. of crystals; ultraviolet absorption peak (95% ethanol) 241.5 mμ (ε13,950). Chromatograph on a column of deactivated neutral alumina, eluting with benzene-petroleum ether (1:1) to obtain dl-13-ethyl-6-methylgon-4-ene-3,17-dione (26 mg), m.p. 141°–149°; ultraviolet absorption peak (95% ethanol) at 242.5 mμ (ε15,450), infrared maxima (potassium bromide) at 5.78 μ, 6.00 μ.

EXAMPLE 215 dl-13-Ethyl-17β-(2-hydroxyethoxy)gon-4-en-3-one, benzoate

Prepare a solution of ether (100 ml), aluminum chloride (13.3 g) and lithium aluminum hydride (15 ml. of a 1 M solution). Stir for 20 minutes. Add to a cool solution of dl-13-ethyl-3-methoxygona-1,3,5(10)-trien-17-one, cyclic ethylene ketal (17.1 g) in ether (1,000 ml). Stir the reaction mixture and cool in an ice-water bath for 4 hours. Dilute with 2 N sulfuric acid until a clear solution results. Separate the ether layer, wash with saturated sodium bicarbonate solution, and evaporate. Treat the residue with ethanol (200 ml), concentrated hydrochloric acid (5 ml) and water (10 ml) on a steam bath for 30 minutes. Evaporate, then recrystallize from ethanol to obtain dl-13-ethyl-17β-(2-hydroxyethoxy)-3-methoxygona-1,3,5(10)-triene (8.1 g), m.p. 131°–132°; ultraviolet absorption peak at 278 mμ (ε2,130), infrared maximum at 2.93 μ.

$C_{22}H_{32}O_3$ Calculated: C, 76.70%; H, 9.36%. Found: C, 76.81%; H, 9.35%.

Dissolve dl-13-ethyl-17β-(2-hydroxyethoxy)-3-methoxygona-1,3,5(10)-triene (4.0 g) in 1-methoxy-2-propanol (60 ml), tetrahydrofuran (120 ml) and liquid ammonia (300 ml). Gradually add lithium (4.0 g) with stirring over a period of 1 hour. Add ammonium chloride (8.0 g) and water. Filter, wash and dry the resulting precipitate. Dissolve the product in tetrahydrofuran (300 ml) and liquid ammonia (300 ml) and treat with lithium (4.0 g). Stir for 1 hour. Add absolute ethanol, then water. Filter the resulting precipitate and wash it with water to obtain dl-13-ethyl-17β-(2-hydroxyethoxy)-3-methoxygona-2,5(10)-diene (3.4 g); essentially no ultraviolet absorption at the 280 mμ region, infrared absorption maxima at 2.91 μ, 5.89 μ, 6.0 μ.

Suspend dl-13-ethyl-17β-(2-hydroxyethoxy)-3-methoxygona-2,5(10)-diene (1.7 g) in methanol (100 ml), concentrated hydrochloric acid (8 ml) and water (5 ml) and stir the suspension for 2 hours under nitrogen. Dilute the clear solution with water and separate the product with ether. Wash the organic layer with a saturated sodium bicarbonate solution and dry over magnesium sulfate. Evaporate the ether to obtain a gum, dl-13-ethyl-17β-(2-hydroxyethoxy)gon-4-en-3-one (1.39 g); ultraviolet absorption peak at 240 mμ (ε13,200), infrared maxima at 2.95 μ, 6.0 μ.

Treat a solution of dl-13-ethyl-17β-(2-hydroxyethoxy)gon-4-en-3-one (1.3 g) in pyridine (6 ml) with benzoyl chloride (1.3 moles) at −10°. Keep the reaction mixture at −10° for 16 hours. Pour over ice and separate the product with ether. Wash the organic layer consecutively with 2 N hydrochloric acid, 2 N sodium hydroxide, water, and brine, then dry over magnesium sulfate. Evaporate the solvent, chromatograph the gum on neutral alumina, and elute with benzene-ethyl acetate to obtain the title compound (800 mg); ultraviolet absorption peak at 233 m$\mu$ ($\epsilon$25,500), infrared maxima at 5.8 $\mu$, 5.98 $\mu$.

$C_{28}H_{36}O_4$ Calculated: C, 77.03%; H, 8.31%. Found: C, 77.44%; H, 8.59%.

This compound has anabolic activity.

EXAMPLE 216 dl-17$\beta$-Hydroxyestr-4-en-3-one

Dissolve dl-3-methoxyestra-2,5(10)-dien-17$\beta$-ol (0.84 g) in methanol (18 ml) containing concentrated hydrochloric acid (1.2 ml) and water (0.8 ml) and allow the mixture to stand at room temperature for 15 hours. Add water and extract the mixture with ether. Wash, dry and evaporate the ethanol solution and dissolve the residue in a little benzene. Filter through a column of alumina (25 g) with benzene-ether (7.3). Evaporate the eluates and recrystallize the residue from etherhexane to obtain the title compound (372 mg), m.p. 123°–124.5° or in an alternate form, m.p. 131°–132°; ultraviolet absorption maximum at 241 m$\mu$ ($\epsilon$16,600); infrared absorption peaks at 6$\mu$, 7.9 $\mu$, 9.4 $\mu$.

$C_{18}H_{26}O_2$ Calculated: C, 78.8%; H, 9.55%. Found: C, 79.08%; H, 9.54%.

This compound has anabolic activity.

EXAMPLE 217 dl-13-Ethylgon-4-ene-3,17-dione, 17-cyclic ethylene ketal

Add dl-13-ethyl-17,17-ethylenedioxy-3-methoxygona-1,3,5(10)-triene (0.35 g) in tetrahydrofuran (20 ml) to a stirred solution of lithium (0.5 g) in liquid ammonia (100 ml). Stir the mixture for 5 minutes and then add ethanol (10 ml) dropwise. When the blue color is discharged, add saturated aqueous ammonium chloride and collect the product in ether. Evaporate the solvent and crystallize the residue from ethanol. Dissolve the product in ethanol (30 ml) and tetrahydrofuran (5 ml) and stir with oxalic acid dihydrate (0.45 g) in water (6 ml) for 1 hour. Add excess 20% aqueous potassium hydroxide, water and collect the product in ether. Wash, dry and evaporate the ethereal solution and filter the residue through a Florex column with benzene-ether (9:1). Recrystallize the product from heptane to obtain the title compound (105 mg), m.p. 129°–131°; ultraviolet absorption peak at 240 m$\mu$ ($\epsilon$16,000), infrared maxima at 6.0 $\mu$, 6.2 $\mu$, 8.6 $\mu$.

$C_{21}H_{30}O_3$ Calculated: C, 76.32%; H, 9.15% Found: C, 76.47%; H, 9.04%

This compound has estrogen antagonistic activity.

EXAMPLE 218 dl-13-Ethyl-17a $\beta$-hydroxy-17a-methyl-D-homogon-4-en-3-one

Reflux dl-13-ethyl-3-methoxy-D-homogona-1,3,5(10),8-tetraen-17a-one (13.3 g) for 8 hours with 3 M methyl magnesium bromide (200 ml) in benzene and recrystallize from methanol to obtain 9.2 g. of the Grignard product, dl-13-ethyl-17a-methyl-17a-hydroxy-D-homogona-1,3,5(10),8-tetraene; ultraviolet absorption peak at 276 m$\mu$ ($\epsilon$15,500), infrared analysis indicating no remaining carbonyl band. Reduce the 8,9-double bond with lithium (1.5 g), liquid ammonia (450 ml), tetrahydrofuran (170 ml) and aniline (30 ml) to obtain the crude D-homo estradiol methyl ether (8.0 g), m.p. 153°–163°; ultraviolet absorption peak at 280 m$\mu$ ($\epsilon$1,314). Reduce further with lithium and ethanol in liquid ammonia to obtain dl-13-ethyl-3-methoxy-17a-methyl-17a-hydroxy-D-homogona-2,5(10)-diene (7.2 g), m.p. 175°–180°. Hydrolyze dl-13-ethyl-3-methoxy-17a-methyl-17a-hydroxy-D-homogona-2,5(10)-diene with hydrochloric acid-methanol-water. Carefully chromatograph on 300 g. Grade III neutral alumina and recrystallize from ethyl acetate-hexane to obtain the title compound (3.35 g), m.p. 129.5°–130.5°; ultraviolet absorption peak at 242 m$\mu$ ($\epsilon$17,100).

$C_{21}H_{32}O_2$ Calculated: C, 79.70%; H, 10.19% Found: C, 79.99%; H, 10.08%

This compound has progestational and anabolic activities.

EXAMPLE 219 dl-17a $\beta$-Hydroxy-13-propyl-D-homogon-4en-3-one

Dissolve 2-propylcyclohexane-1,3-dione (36.3 g) in benzene (400 cc) containing pyridine (21.2 cc). Add 6-m-methoxyphenylhex-1-en-3-one (43.2 g) and reflux the solution over night. Cool the reaction mixture, wash with water, aqueous sodium carbonate, and 10% aqueous sulfuric acid, dry and remove the solvents under reduced pressure to obtain 2-(6-m-methoxyphenyl-3-oxohexyl)-2-propylcyclohexane-1,3-dione.

Heat 2-(6-m-methoxyphenyl-3-oxohexyl)-2-propylcyclohexane-1,3-dione (43.0 g) in benzene (400 cc) with polyphosphoric acid (250 g) for 3 hours at 60° with vigorous stirring. Add ice water (400 cc) and separate the benzene layer. Extract the water with ether, combine the organic layers; wash, dry and evaporate. Recrystallize this residue from ethanol (250 cc) to obtain dl-3-methoxy-13-propyl-D-homogona-1,3,5(10),8,14-pentaen-17a-one (27.6 g), m.p. 86°–89°C, $\lambda$max. KBr 5.87 $\mu$, 6.25 $\mu$; $\lambda$max. EtOH 312 m$\mu$ ($\epsilon$24,300).

$C_{22}H_{26}O_2$ Calculated: C, 81.95%; H, 8.13%. Found: C, 82.11%; H, 8.18%.

Hydrogenate dl-3-methoxy-13-propyl-D-homogona-1,3,5(10),8,14-pentaen-17a-one (27.6 g) dissolved in tetrahydrofuran (250 cc) over 2% Pd/CaCO$_3$ (7.0 g). Uptake of one mole requires 15 minutes. Filter, remove solvent and boil with 95% ethanol (250 cc). Filter to obtain dl-3-methoxy-13-propyl-D-homogona-1,3,5(10),8-tetraen-17a-one (25.5 g), m.p. 146°–148°C, $\lambda$max. EtOH 277 m$\mu$ ($\epsilon$16,130).

$C_{22}H_{28}O_2$ Calculated: C, 81.42%; H, 8.69%. Found: C, 81.30%; H, 8.62%.

Reflux dl-3-methoxy-13-propyl-D-homogona-1,3,5(10),8-tetraen-17a-one (20 g) in ethanol (250 cc) with sodium borohydride (7.0 g) for one hour. Make acid with 50% aqueous acetic acid, add water (500 cc), filter, wash and recrystallize from ethanol (250 cc) to obtain dl-3-methoxy-13-propyl-D-homogona-1,3,5(10),8-tetraen-17a $\beta$-ol (16.0 g), m.p. 122°–124°, $\lambda$max. KBr 3.02 $\mu$, 6.25 $\mu$; $\lambda$max. EtOH 275 m$\mu$ ($\epsilon$16,325).

$C_{22}H_{30}O_2$ Calculated: C, 80.92%; H, 9.27%. Found: C, 80.74%; H, 9.81%.

Add dl-3-methoxy-13-propyl-D-homogona-1,3,5(10),8-tetraen-17a $\beta$-ol (16.0 g) dissolved in tetrahydrofuran (100 cc) and aniline (100 cc) to liquid ammonia (900 cc) containing tetrahydrofuran (250 cc). Add lithium metal (1.0 g), stir for one hour and discharge the blue color by addition of water. Extract the product with ether, remove aniline by shaking with dilute hydrochloric acid, and wash, dry and evaporate the solvent. Recrystallize twice from methanol to obtain dl-3-methoxy-13-propyl-D-homogona-1,3,5(10)-trien-17a β-ol (13.0 g), m.p. 123°–125°, λmax. EtOH 280 mμ (ε1,900).

$C_{22}H_{32}O_2$ Calculated: C, 80.43%; H, 9.82%. Found: C, 80.33%; H, 9.90%.

Treat dl-3-methoxy-13-propyl-D-homogona-1,3,5(10)-trien-17a β-ol (13.0 g) dissolved in tetrahydrofuran (240 cc) and liquid ammonia (500 cc) with lithium metal (3.5 g). Stir 1.5 hours, discharge the blue color by dropwise addition of absolute ethanol, add water and filter the crude product. Triturate with methanol (110 cc) to obtain dl-3-methoxy-13-propyl-D-homogona-2,5(10)-dien-17aβ-ol (11.4 g), m.p. 150°–157°, λmax. KBr 3.09 μ, 5.90 μ, 6.0 μ.

Hydrolyze dl-3-methoxy-13-propyl-D-homogona-2,5(10)-dien-17a β-ol (1.4 g) with methanol (80 cc) concentrated hydrochloric acid (6.0 cc) and water (4.0 cc) and isolate the product. Recrystallize from ethyl acetate to obtain the title compound (0.80 g), m.p. 150°–152°, λmax. KBr 3.0 μ, 6.04 μ; λmax. EtOH 240 mμ (ε16,300).

$C_{21}H_{32}O_2$ Calculated: C, 79.70%; H, 10.19%. Found: C, 79.60%; H, 10.10%.

This compound has anabolic activity.

EXAMPLE 220 dl-17β-Hydroxyestr-4-en-3-one, acetate

Add sodium borohydride (8.5 g) to 3-methoxyestra-1,3,5(10),8-tetraen-17-one (40 g) in ethanol (500 ml) and reflux the mixture for 90 minutes. Acidify the cooled solution with acetic acid, add water and extract with benzene. Wash, dry and evaporate the organic extract to obtain dl-3-methoxyestra-1,3,5(10),8-tetraen-17β-ol (37.5 g), m.p. 130°–133°; ultraviolet absorption peak at 280 mμ(ε16,100); infrared maxima at 3.1 μ, 3.58 μ, 6.25 μ, 6.4 μ, 6.7 μ.

Add dl-3-methoxyestra-1,3,5(10),8-tetraen-17β-ol (37.5 g) in tetrahydrofuran (350 ml) to a stirred solution of liquid ammonia (1 liter) and aniline (45 ml). Add lithium (2 g), stir for 30 minutes, and then add ammonium chloride (20 g) followed by water. Extract with ether-benzene (1:1) and wash the organic solution with water, excess 3N hydrochloric acid, water and dry. Evaporate the solvent and recrystallize the residue from ethyl acetate-hexane to obtain dl-3-methoxyestra-1,3,5(10)-trien-17β-ol (12 g), m.p. 121°–124°; ultraviolet absorption peak at 278 mμ (ε1,810); infrared maxima at 3.0 μ, 6.2 μ, 6.75 μ.

Add dl-3-methoxyestra-1,3,5(10)-trien-17β-ol (1.3 g) in tetrahydrofuran (40 ml) to a stirred solution of lithium (1.3 g) in liquid ammonia (100 ml). After 15 minutes add ethanol (20 ml) dropwise and when the blue color is discharged add ammonium chloride and water and extract the mixture with ether. Wash, dry and evaporate the ethereal solution and recrystallize the residue from ethanol-hexane to obtain dl-3-methoxyestra-2,5(10)-dien-17β-ol (0.84 g), m.p. 120°–123°; infrared absorption maxima at 3.25 μ, 5.8 μ, 6 μ.

Dissolve the foregoing alcohol in ether, add 25% hydrochloric acid. Stir the mixture at room temperature for 15 minutes and add crushed ice. Evaporate the washed and dried ether layer and recrystallize the residue from ether-hexane containing a little ethyl acetate to obtain dl-17β-hydroxyestr-4-en-3-one, m.p. 121°–123°, λmax. 241 mμ (ε17,000). Acetylate the foregoing alcohol with acetic anhydride in pyridine and recrystallize the product from ether-light petroleum to obtain the ester, m.p. 113°–114°, λmax. 242 mμ (ε17,600).

$C_{20}H_{28}O_3$ Calculated: C, 75.9%; H, 8.9%. Found: C, 76.0%; H, 8.8%.

This compound has anabolic activity.

EXAMPLE 221 dl-3-(13-Ethyl-17β-hydroxy-3-oxogon-4-en-17α-yl)propionic acid, γ-lactone

Add 13-ethyl-17α-ethynyl-3-methoxygona-1,3,5(10)-trien-17β-ol (20 g) in tetrahydrofuran with stirring to refluxing 3M ethereal methylmagnesium bromide (240 ml)-tetrahydrofuran (300 ml). Pass gaseous carbon dioxide into the cooled mixture for 22 hours. Add the mixture to crushed ice, acidify with dilute sulfuric acid, remove most of the tetrahydrofuran under reduced pressure and extract the mixture with ether. Extract the ethereal solution with aqueous sodium carbonate and acidify the extracts. Filter off the crude dl-3-(13-ethyl-17β-hydroxy-3-methoxygona-1,3,5(10)-trien-17α-yl)prop-2-ynoic acid, m.p. 172°–173°. Recrystallize an aliquot from methanol to obtain pure substance, m.p. 173°–174° (gas evolution).

$C_{23}H_{28}O_4$ Calculated: C, 75.0%; H, 7.7% Found: C, 74.9%; H, 7.4%

Hydrogenate the foregoing acid (3.7 g) in ethanol (100 ml) over 10% palladized charcoal (1 g) until hydrogen uptake ceases. Recrystallize the product from ethyl acetate-hexane to obtain dl-3-(13-ethyl-17β-hydroxy-3-methoxygona-1,3,5(10)-trien-17α-yl)propionic acid, γ-lactone, m.p. 174°–175°, infrared absorption peak at 5.67 μ.

$C_{23}H_{30}O_3$ Calculated: C, 77.9%; H, 8.5%. Found: C, 77.6%; H, 8.4%.

Reflux the foregoing lactone with triethylamine (180 ml) and sodium hydroxide (1.0 g) in water (33 ml) overnight. Evaporate the mixture to dryness and treat residue with a solution of tert-butyl alcohol (100 ml), 1-methoxy-2-propanol (200 ml) and liquid ammonia (600 ml). Add lithium (5.0 g) and after 40 minutes add ammonium chloride (40 g) followed by water. Acidify with cold hydrochloric acid (18%) in the presence of ice and filter off the precipitate. Add the dried material (2.4 g) to methanol (110 ml), concentrated hydrochloric acid (5 ml) and water (5 ml) and stir for one hour. Dilute with water and filter the precipitate. Recrystallize the dried material from ethyl acetate-hexane to obtain 1.1 g. of the title product; m.p. 214°–215°; ultraviolet absorption peak at 240 mμ (ε17,100).

$C_{22}H_{30}O_3$ Calculated: C, 77.15%; H, 8.83% Found: C, 77.20%; H, 8.61%

EXAMPLE 222 dl-13-Ethyl-17β-hydroxy-17-(1-hydroxyethyl)gon-4-en-3-one

Reduce dl-13-ethyl-17α-acetyl-17-hydroxy-3-methoxygona-1,3,5(10)-triene, acetate (1.0 g) in lithium aluminum hydride and ether to produce a gum, dl-13-ethyl-17β-hydroxy-17-(1-hydroxyethyl)-3-methoxygona-1,3,5(10)-triene (0.9 g); infrared absorption peak very strong at 2.9 μ(OH band). Reduce dl-13-ethyl-17β-hydroxy-17-(1-hydroxyethyl)-3-methoxygona-1,3,5(10)-triene (0.9 g) with tetrahydrofuran (60 ml), liquid ammonia (150 ml), lithium (700 mg) and absolute ethanol, and filter to obtain a crystalline solid, dl-13-ethyl-17β-hydroxy-17-(1-hydroxyethyl)-3-methoxygona-2,5(10)-diene (0.70 g), m.p. 152°–161°; ultraviolet analysis indicating no remaining aromatic system, infrared maxima at 3.0 μ, 5.9 μ, 6.0 μ.

Hydrolyze dl-13-ethyl-17β-hydroxy-17-(1-hydroxyethyl)-3-methoxygona-2,5(10)-diene (0.70 g) in hydrochloric acid-methanol-water. Recrystallize from ethyl acetate to obtain the title compound (0.36 g), m.p. 159°–164°; ultraviolet absorption peak at 240 mμ (ε15,230), infrared absorption peaks at 3.0 μ (strong), 6.05 μ.

$C_{21}H_{32}O_3$ Calculated: C, 75.85%; H, 9.70%. Found: C, 76.12%; H, 9.78%.

This compound has progestational activity.

EXAMPLE 223 dl-17-Hydroxy-17α-ethynylestr-4-en-3-one, acetate

Treat dl-17-hydroxy-17α-ethynylestr-4-en-3-one (1 g) with acetic anhydride (10 ml) and toluene-p-sulfonic acid (0.1 g) and heat at 90° for 1 hour. Pour the cooled solution into water, neutralize with sodium bicarbonate and extract with ether. Wash, dry and evaporate to obtain dl-17-ethynylestra-3,5-diene-3,17β-diol, diacetate; infrared absorption maxima at 3μ, 5.7μ, 5.75μ.

Hydrolyze dl-17-ethynylestra-3,5-diene-3,17β-diol, diacetate (0.4 g) in methanol (60 ml) and tetrahydrofuran (10 ml) with 2% methanolic potassium hydroxide at 0° for 1 hour. Pour into water, neutralize with dilute hydrochloric acid and extract with ether. Wash, dry and evaporate the ethereal solution and chromatograph the product on ethyl acetate washed alumina. Recrystallize the product from ether-light petroleum ether to obtain the title compound (0.3 g), m.p. 153°–155°; ultraviolet absorption peak at 240 mμ (ε16,400); infrared absorption maxima at 3.1 μ, 3.45 μ, 5.22 μ, 6.0 μ.

$C_{22}H_{28}O_2$ Calculated: C, 77.65%; H, 8.29%. Found: c, 78.1%; H, 8.47%.

This compound has progestational activity.

EXAMPLE 224 dl-17α-(3-Diethylamino-1-propynyl)-13-ethylgon-4-en-17-ol

Stir a suspension of 1.1 g. of dl-17α-ethynyl-13-ethylgon-4-en-17-ol, 12 ml. of dioxane, 0.6 ml. of water, 0.6 ml. of formaldehyde (40% in water), 0.5 ml. of diethylaniline, 0.4 ml. of acetic acid, and 20 mg. of cuprous chloride for 22 hours at 60°. Pour into ice, basify with sodium hydroxide and extract with ether. Mix the residue with a solution of aqueous hydrochloric acid and acetic acid and extract with ether. Basifly the aqueous layer with aqueous potassium hydroxide and filter off the product. Recrystallize from 35 ml. of methanol to obtain 900 mg. of the desired product; m.p. 149°–150°.

$C_{26}H_{41}NO$ Calculated: C, 81.40%; H, 10.77%; N, 3.65%. Found: C, 81.44%; H, 10.81%; N, 3.63%. This compound has antiinflammatory activity.

EXAMPLE 225 dl-13-Ethyl-17-ethynylgon-4-en-3,17β-diol-3-acetate

Add sodium borohydride (1.0 g) to 13-ethyl-17α-ethynyl-17β-hydroxygon-4-en-3-one (1.0 g) in ethanol (100 ml) and allow the mixture to stand for 2 hours. Decompose excess reagent with acetic acid and remove most of the solvent under reduced pressure. Dissolve the product in ether and water, and wash, dry and evaporate the ethereal solution. Dissolve the residue in pyridine (5 ml) and acetic anhydride (5 ml) and after 3 hours remove the solvents under vacuum. Add ether, wash, dry and evaporate the ethereal solution and recrystallize the residue from ethyl acetate-methanol to obtain the title compound (0.42 g), m.p. 168°–170°.

$C_{23}H_{32}O_3$ Calculated: C, 77.49%; H, 9.05%. Found: C, 77.12%; H, 9.35%.

This compound has progestational activity.

EXAMPLE 226 dl-13-Ethyl-17β-(tetrahydropyran-2-yloxy)gon-4-en-3-one

Add with swirling a solution of p-toluenesulfonic acid (14 mg) in benzene (0.8 mole) to dl-17β-hydroxy-13-ethylgon-4-en-3-one (450 mg) in 2,3-dihydropyran (3 ml). After 2 hours, neutralize the reaction mixture with methanolic sodium hydroxide. Add water, together with some methanol, scratch the mixture and allow it to stand at 0° for about 70 hours. filter to obtain the title compound (100 mg), m.p. 148°–152°; infrared absorption peaks at 6.0 μ, 6.2 μ, 9.02 μ, 9.42 μ, 9.68 μ, 9.85 μ, 10.25 μ (no hydroxyl band).

$C_{24}H_{36}O_3$ Calculated: C, 77.31%; H, 9.74%. Found: C, 77.15%; H, 9.52%.

This compound has anabolic activity.

EXAMPLE 227 dl-13-Ethyl-17α-ethynyl-17-hydroxy-6α-methylgon-4-en-3-one

Reflux dl-13-ethyl-3-methoxy-6-methylgona-2,5-(10)-dien-17β-ol (5.5 g) in toluene (200 cc) and cyclohexanone (70 cc) with aluminum isopropoxide (4.0 g) for 2.5 hours. Add water and anhydrous sodium sulfate, filter and isolate the crude product. Triturate with ice cold methanol to obtain dl-13-ethyl-3-methoxy-6-methylgona-2,5-(10)-dien-17-one (3.6 g), m.p. 118°–125°, λmax. KBr 5.78 μ, 5.90 μ, 6.0 μ. An analytical sample recrystallized from methanol has m.p. 163°–166°.

Stir dl-13-ethyl-3-methoxy-6-methylgona-2,5-(10)-dien-17-one (3.6 g) in dimethylacetamide (35 cc) in a stream of acetylene for one-half hour. Add lithium acetylide-ethylenediamine (2.7 g) and stir for 4 hours. Pour into ice water, extract with ether and isolate the dl-13-ethyl-3-methoxy-17α-ethynyl-17β-hydroxy-6-methylgona-2,5(10)-diene as a gum (3.5 g), λmax. NaCl 2.90 μ, 3.05 μ, 5.90 μ, 6.03 μ.

Stir dl-13-ethyl-3-methoxy-17α-ethynyl-17-hydroxy-6-methylgona-2,5(10)-diene (3.5 g) in methanol (90 cc) containing hydrochloric acid (60 cc) and water (4.0 ml) under nitrogen for 1 hour. Isolate the crude product, chromatograph on Florex (150 g) and recrystallize from ethyl acetate-hexane to obtain the title compound (0.60 g), m.p. 148°–151°, λmax. $CHCl_3$ 2.55 μ, 3.05 μ, 6.01 μ; λmax. EtOH 240 mμ (ε15,100).

$C_{22}H_{30}O_2$ Calculated: C, 80.92%; H, 9.26%. Found: C, 81.01%; H, 9.56%.

This compound has progestational activity.

EXAMPLE 228

13-Ethyl-17α-ethynyl-17β-hydroxygon-4-en-3-one, 2'-tetrahydropyranyl ether

Keep 13-ethyl-17α-ethynyl-17β-hydroxygon-4-en-3-one (0.5 g) in dihydropyran (5 ml)-benzene (0.8 ml) containing toluene-p-sulfonic acid (14 mg. of the hydrate) over night. Add ether and aqueous sodium bicarbonate. Evaporate the washed and dried ether solution. Purify the product by chromatography on alumina and recyrystallize from hexane to obtain the title substance (0.22 g), m.p. 145°–150°.

$C_{26}H_{30}O_3$ Calculated: C, 78.4%; H, 9.15%. Found: C, 78.7%; H, 9.0%.

This compound has progestational activity.

EXAMPLE 229

17α-Chloroethynyl-13-ethyl-17β-hydroxygon-4-en-3-one, 2'-tetrahydropyranyl ether Keep 17α-chloroethynyl-13-ethyl-17β-hydroxygon-4-en-3-one (0.5 g) in 2,3-dihydropyran (5 ml)-benzene (0.8 ml) containing toluene-p-sulfonic acid (14 mg of the hydrate) over night, then add ether and aqueous sodium bicarbonate. Purify the product by recrystallization from hexane to obtain the title substance, m.p. 125°–131°.

$C_{26}H_{35}O_3Cl$ Calculated: C, 72.45%; H, 8.2%; Cl, 8.2%. Found: C, 72.4%; H, 8.1%; Cl, 8.2%.

This compound has progestational activity.

EXAMPLE 230

13,17α-Diethyl-17β-hydroxygon-4-en-3-one, 2'-tetrahydropyranyl ether

Keep 13,17α-diethyl-17β-hydroxygon-4-en-3-one (0.5 g) in 2,3-dihydropyran (5 ml)-benzene (0.8 ml) containing toluene-p-sulfonic acid overnight, then add ether and aqueous sodium bicarbonate. Purify the product by chromatography on alumina to obtain the title substance.

This compound has anabolic activity.

EXAMPLE 231 dl-13-Ethyl-17β-hydroxy-6α-methylgon-4-en-3-one

Reflux 2-(6-m-methoxyphenyl)-3-oxoheptyl-2-ethylcyclopentane-1,3-dione (53.3 g) in benzene (600 cc) with p-toluenesulfonic acid monohydrate (15 g) using a water separator. Wash, dry and evaporate the benzene solution and distil the residual gum at .003 mm./180°–200°C. Obtain the dl-3-methoxy-6-methyl-13-ethylgona-1,3,5(10),8,14-pentaen-17-one as an orange gum (38.0 g), λ max. EtOH 311 mμ (ε27,200).

Reflux 2-(6-m-methoxyphenyl)-3-oxoheptyl-2-ethylcyclopentane-1,3-dione (39.7 g) in benzene (500 cc) with p-toluenesulfonic acid monohydrate (11.0 g) using a water separator. After removal of two moles of water, add ethylene glycol (50 cc) and reflux the solution 16 hours. Wash, dry and evaporate the benzene solution and dissolve the residue in hexane. Filter the solution several times through Florex, remove the solvent and recrystallize the residue from ethanol to obtain the dl-3-methoxy-6-methyl-17,17-ethylenedioxy-13-ethylgona-1,3,5(10), 8,14-pentaene (16.8 g), m.p. 116°–119°. Recrystallize a small portion to obtain an analytical sample, m.p. 120°–122°C, λmax. EtOH 312 mμ (ε31,000).

Monohydrogenate dl-3-methoxy-6-methyl-17,17-ethylenedioxy-13-ethylgona-1,3,5(10), 8,14-pentaene (15.3 g) in benzene (300 cc) in the presence of 2% Pd/CaCO₃ (5.0 g). Filter, remove the benzene under reduced pressure and recrystallize from 95% ethanol (110 cc) to yield the dl-3-methoxy-6-methyl-17,17-ethylenedioxy-13-ethylgona-1,3,5(10),8-tetraene (11.0 g), m.p. 122°–124°, diamond shaped plates, λmax. EtOH 280 mμ (ε15,140).

Add dl-3-methoxy-6-methyl-17,17-ethylenedioxy-13-ethylgona-1,3,5(10),8-tetraene (11.0 g) in tetrahydrofuran (160 cc) to liquid ammonia (600 cc) containing tetrahydrofuran (170 cc) and aniline (30 cc). Add lithium (0.6 g) in small portions and stir for 2 hours. Add solid ammonium chloride followed by water and extract with ether. Isolate the product which crystallizes on scratching, λmax. EtOH 280 mμ (ε1,975). To obtain an analytical sample recrystallize from isopropanol to obtain the purified title compound, m.p. 130°–134°C.

Suspend dl-3-methoxy-17,17-ethylenedioxy-6-methyl-13-ethylgona-1,3,5-(10)-triene (9.0 g) in methanol (200 cc) and concentrated hydrochloric acid (5.0 cc) and heat on the steam bath for 15 minutes. Remove the solvent under vacuum, partition the residue between ether and aqueous sodium bicarbonate and isolate the product. Recrystallize from methanol to obtain the dl-3-methoxy-6-methyl-13-ethylgona-1,3,5(10)-trien-17-one (7.29 g), m.p. 115°–123°C. Recrystallize a small portion to obtain an analytical sample, m.p. 123°–127°C, λmax. EtOH 280 mμ, λmax. KBr 5.75 μ.

$C_{21}H_{28}O_2$ Calculated: C, 80.73%; H, 9.03%. Found: C, 80.43%; H, 8.96%.

Dissolve dl-3-methoxy-6-methyl-13-ethylgona-1,3,5(10)-trien-17-one (7.0 g) in methanol (300 cc) and treat with sodium borohydride (3.0 g). After spontaneous reflux ceases, make acid with 50% aqueous acetic acid (20 cc). Pour into brine, extract with acid and isolate the dl-3-methoxy-17β-hydroxy-6-methyl-13-ethylgona-1,3,5(10)-triene (6.8 g), m.p. 158°–160°C, λmax. KBr 3.05, 6.45 μ.

$C_{21}H_{30}O_2$ Calculated: C, 80.21%; H, 9.61%. Found: C, 80.8%; H, 9.04%.

Add dl-3-methoxy-17β-hydroxy-6-methyl-13-ethylgona-1,3,5(10)-triene 96.80 g) in tetrahydrofuran (200 cc) to liquid ammonia (800 cc) containing tetrahydrofuran (250 cc). Add lithium metal (3.5 g) portionwise and stir the solution for 1.75 hours. Discharge the blue color by dropwise addition of absolute ethanol over 0.25 hours followed by water (2,000 cc). Filter, wash and dry to obtain the dl-3-methoxy-17β-hydroxy-6-methyl-13-ethylgona-2,5(10)-diene (6.5 g), m.p. 176°–182°, λmax. KBr 3.05 μ, 5.90 μ, 6.0 μ, no absorption in the ultraviolet above 220 mμ.

Stir dl-3-methoxy-17β-hydroxy-6-methyl-13-ethylgona-2,5(10)-diene (1.0 g) in methanol (54 cc) containing concentrated hydrochloric acid (3.6 cc) and water (2.4 cc) under nitrogen for 1.5 hours. Pour into brine, extract with ether and isolate the crude product. Chromatograph on Grade I neutral alumina (50 g) and recrystallize from ether-hexane to obtain the title compound (0.30 g), m.p. 127°–130°, λmax. KBr 2.98 μ, 6.03 μ; λmax. EtOH 240 mμ (ε16,500).

$C_{20}H_{30}O_2$ Calculated: C, 79.42%; H, 10.00%. Found: C, 79.57%; H, 9.87%.

This compound has progestational activity.

EXAMPLE 232 dl-13-Ethyl-17-ethynylgon-4-en-3,17β-diol, 3-propionate

Add sodium borohydride (0.8 g) to 13-ethyl-17-ethynyl-17β-hydroxygon-4-en-3-one (1.7 g) in ethanol (100 ml) and allow the mixture to stand for 15 hours. Dilute the mixture with water and extract with ether. Wash, dry and evaporate the ethereal solution and dissolve the residue in pyridine (5 ml) and propionic anhydride (5 ml). After 2 hours add ice and water and extract the mixture with ether. Wash the ethereal extract with water, 10% aqueous sodium hydroxide, water, 10% hydrochloric acid, and brine and dry. Evaporate the solvent and recrystallize the product from ethyl acetate to obtain the title compound (0.5 g), m.p. 153°–156°.

$C_{24}H_{34}O_3$ Calculated: C, 77.8%; H, 9.25%. Found: C, 77.63%; H, 9.16%.

This compound has progestational activity.

EXAMPLE 233 dl-13-Ethyl-17α-ethynyl-17-hydroxy-6α-methylgon-4-en-3-one and dl-13,17α-Diethyl-17-hydroxy-6α-methylgon-4-en-3-one Dissolve 2-ethyl-2-(6-m-methoxyphenyl-6-methyl-3-oxohexyl)-1,3-cyclopentanedione (39.7 g) in benzene (500 ml) and reflux with p-toluenesulfonic acid in water (11.0 g). Remove 2 moles of water, add ethyleneglycol (50 ml) and reflux the solution overnight (16 hours). After working up by the usual procedure, filter repeatedly through Florex in hexane. Recrystallize from ethanol to obtain dl-13β-ethyl-3-methoxy-6-methyl-17,17-ethylenedioxygona-1,3,5-(10),8,14-pentaene (16.8 g), m.p. 120°–122°; ultraviolet absorption peak at 312 mμ, no infrared absorption in the ketone region.

Hydrogenate dl-13β-ethyl-3-methoxy-6-methyl-17,17-ethylenedioxygona-1,3,5(10),8,14-pentaene (15.3 g) in benzene (300 ml) with 2% palladized strontium carbonate (5.0 g). The uptake of 1,040 ml. will require 10 minutes. Work up in the usual manner, then recrystallize from 95% ethanol (110 ml) to obtain dl-13β-ethyl-3-methoxy-6-methyl-17,17-ethylenedioxygona-1,3,5(10)-,8-tetraene (11.0 g. of diamond-shaped plates; 71.8% yield), m.p. 122°–124°; ultraviolet absorption peak at 280 mμ (ε15,140).

Add dl-13-ethyl-3-methoxy-6-methyl-17,17-ethylenedioxygona-1,3,5-(10),8-tetraene (11.0 g) in tetrahydrofuran (160 ml) to liquid ammonia (600 ml) containing tetrahydrofuran (170 ml) and aniline (30 ml). Then add lithium (0.6 g) in small portions and stir for 2 hours. Work up in the usual way to obtain dl-13-ethyl-3-methoxy-6-methyl-17,17-ethylenedioxygona-1,3,5-(10)-triene as a gum (9.5 g) that will crystallize on scratching. Recrystallize from isopronanol to obtain a product with m.p. 130°–134°; ultaviolet absorption peak at 280 mμ (ε1,976), no infrared absorption in the ketone region.

Suspend dl-13-ethyl-3-methoxy-6-methyl-17,17-ethylenedioxygona-1,3,5(10)-triene (9.0 g) in methanol (200 ml) and concentrated hydrochloric acid (5 ml). Heat the mixture on a steam bath for 15 minutes. Remove the solvent under vacuum and partition the residue between ether and aqueous sodium bicarbonate. Remove the organic solvents and dry to obtain a gum. Recrystallize from methanol to obtain dl-13-ethyl-3-methoxy-6-methylgona-1,3,5-(10)-trien-17-one (7.29 g), m.p. 115°–123°. Recrystallize from methanol to obtain an analytical sample with m.p. 123°–127°; ultraviolet absorption peak at 280 mμ (ε2,190), infrared maximum (potassium bromide) at 5.75 μ.

$C_{21}H_{28}O_2$ Calculated: C, 80.73%; H, 9.03%. Found: C, 80.43%; H, 8.961 %.

Dissolve dl-13-ethyl-3-methoxy-6-methylgona-1,3,5(10)-trien-17-one (7.0 g) in methanol (300 ml) and treat with sodium borohydride (3.0 g). After spontaneous reflux ceases, acidify the reaction mixture with 50% acetic acid (20 ml). Work up by the usual procedures to obtain dl-13-ethyl-3-methoxy-6-methylgona-1,3,5(10-trien-17β-ol (6.8 g), m.p. 158°–160°; infrared absorption peaks (potassium bromide) at 3.05 μ, 6.45 μ.

$C_{21}H_{30}O_2$ Calculated: C, 80.21%; H, 9.61%. Found: C, 80.13%; H, 9.40%.

Add dl-13-ethyl-3-methoxy-6-methylgona-1,3,5-(10)-trien-17β-ol (6.80 g) in tetrahydrofuran (200 ml) to ammonia (800 ml) containing tetrahydrofuran (250 ml). Add lithium (3.5 g) and stir the solution for 1.75 hours. Discharge the blue color by dropwise addition of ethanol over a period of 0.25 hour. Add water. Filter and dry the product, dl-13, -ethyl-3-methoxy-6-methyl-gona-2,5(10)-dien-17β-ol (6.5 g), m.p. 176°–182°; infrared absorption peaks (potassium bromide) at 3.05 μ, 5.90 μ, 6.0 μ, no selective ultraviolet absorption above 220 mμ

Dissolve dl-13-ethyl-3-methoxy-6-methylgona-2,5(10)-dien-17β-ol (5.5 g) in toluene (200 ml) containing cyclohexanone (70 ml) and treat with aluminum isopropoxide (4.0 g) in toluene (50 ml). Reflux under nitrogen for 2.5 hours, then add water (10 ml) followed by anhydrous sodium sulfate (5 g). Stir the suspension for 0.5 hour, filter, and wash the filter cake with benzene. Remove the solvents and concentrate the residue at 100° under vacuum (.02 mm). Triturate the crystalline residue with ice-cold methanol to obtain dl-13β-ethyl-6-methyl-3-methoxygona-2,5(10)-dien-17-one (3.6 g), m.p. 118°–125°; infrared absorption peaks (potassium bromide) at 5.78 μ, 5.90 μ, 6.00 μ, no selective ultraviolet absorption above 220 mμ

Dissolve dl-13-ethyl-6-methyl-3-methoxygona-2,5(10)-dien-17-one (3.6 g) in dimethylacetamide (35 ml) and stir in a stream of acteylene for 0.5 hour. Add solid lithium acetylide-ethylenediamine (2.7 g) and stir the solution for 4 hours. Pour the reaction mixture onto ice, extract with ether, wash the ether layer with water, dry, and evaporate to obtain dl-13-ethyl-3-methoxy-6-methyl-17α-ethynyl-17-hydroxygona-2,5(10)-diene (3.5 g) as a gum; infrared absorption peaks (sodium chloride) at 2.90 μ, 3.05 μ, 5.90 μ, 6.03 μ.

Dissolve dl-13-ethyl-3-methoxy-6-methyl-17α-ethynyl-17-hydroxygona-2,5(10)-diene (3.5 g) in methanol (90 ml) containing concentrated hydrochloric acid (6.0 ml) and water (4.0 ml). Stir the solution under nitrogen for 1 hour. Work up in the usual fashion. Chromatograph on Florex (150 g), then recrystallize from ether-hexane to obtain dl-13-ethyl-17α-ethynyl-17-hydroxy-6α-methylgon-4-en-3-one (0.60 g), m.p. 148°–151°; ultraviolet absorption peak at 240 mμ (ε15,300), infrared maxima (chloroform) at 2.55 μ, 3.05 μ, 6.01 μ.

$C_{22}H_{30}O_2$ Calculated: C, 80.92%; H, 9.25%. Found: C, 81.01%; H, 9.56%.

This compound has progestational activity.

Hydrogenate dl-13-ethyl-17α-ethynyl-17-hydroxy-6α-methylgon-4-en-3-one (0.15 g) in benzene (20 ml) with 2% palladized strontium carbonate (25 mg). Recrystallize from ether to obtain dl-13,17α-diethyl-17-hydroxy-6β-methylgon-4-en-3-one (0.03 g); infrared absorption peaks at 2.95 μ, 6.04 μ, 6.20 μ.

This compound has anabolic activity.

EXAMPLE 234 dl-13-Ethyl-17aα-chloroethynyl-17aβ-hydroxy-D-homogon-4-en-3-one

Dissolve dl-13-ethyl-3-methoxy-D-homogona-2,5(10)-dien-17aβ-ol (20.5 g) in toluene (350 cc) and cyclohexanone (100 cc) and azeotrope under nitrogen to remove water. Add aluminum isopropoxide (16.0 g) in toluene (50 cc) and reflux for 2 hours. Cool, add water (20 cc), stir for 15 minutes and add anhydrous sodium sulfate (40 g). Filter and isolate the crude product by concentration under vacuum. Triturate with boiling methanol (200 cc), filter and dry to obtain dl-13-ethyl-3-methoxy-D-homogona-2,5(10)-dien-17a-one (18.0 g), m.p. 135°–140°, λmax. KBr 5.87 μ, 6.0 μ.

Dilute methyl lithium (94.6 g, 0.218 M) in ether with ether (200 cc) and cool to 0°. Add cis-dichloroethylene (11.0 g. 0.109 M) over one hour. Add dl-13-ethyl-3-methoxy-D-homogona-2,5(10)-dien-17a-one (12.0 g) suspended in ether (250 cc). Stir at room temperature for 1 hour, cool in an ice bath and add saturated aqueous ammonium chloride (250 cc) dropwise. Separate, wash, dry and evaporate the ether layer and triturate the crystalline residue with boiling methanol (100 cc). Filtrate gives dl-13-ethyl-17aα-chloroethynyl-3-methoxy-D-homogona-2,5(10)-dien-17aβ-ol (13.0 g), m.p. 120°–126°C. λmax. KBr 3.0 μ, 4.54 μ, 5.90 μ, 5.99 μ

Suspend dl-13-ethyl-17aα-chloroethynyl-3-methoxy-D-homogona-2,5(10)-dien-17aβ-ol (13.0 g) in methanol (180 cc), water (8.0 cc) and concentrated hydrochloric acid (12.0 cc), and stir under nitrogen. Add tetrahydrofuran (15 cc) and dioxane (15 cc) to effect solution. Pour into brine, extract with ether and isolate the crude product. Recrystallize from ethyl acetate (100 cc) and hexane (70 cc) to obtain the title compound (7.4 g), m.p. 204°–206°C, λmax. KBr 2.90, 4.52, 6.0 μ; λmax. EtOH 240 mμ (ε16,820)

$C_{22}H_{29}O_2Cl$ Calculated: C, 73.21%; H, 8.10%; Cl, 9.82%. Found: C, 73.48%; H, 8.10%; Cl, 9.6%.

This compound has progestational activity.

EXAMPLE 235 dl-13,17α-Diethylgon-4-en-3,17-diol, 3-propionate

Treat dl-13,17α-diethylgon-4-en-3,17-diol (1.0 g) in pyridine (25 ml) with propionic anhydride (2 ml) and allow to stand at room temperature for 14 hours. Evaporate the solvents under reduced pressure to give the title compound as a glass (1.18 g), infrared absorption peaks at 2.93 μ, 5.80 μ and 6.0 μ

$C_{24}H_{38}O_3$ Calculated: C, 76.96%; 10.23%. Found: C, 76.40%; 10.70%.

This compound has anabolic activity.

EXAMPLE 236 dl-13-Ethyl-17aβ-hydroxy-D-homogon-4-en-3-one

Add dl-13-ethyl-D-homo-3-methoxygona-1,3,5(10)-trien-17aβ-ol (24.4 g) in tetrahydrofuran (200 cc) to liquid ammonia (1,000 cc) containing tetrahydrofuran (300 cc). Add lithium metal (7.0 g) portionwise and stir for 1.5 hours. Add absolute ethanol dropwise until the blue color is discharged, followed by water. Boil the precipitated solid with methanol (200 cc) and chill. Filter and dry the dl-13-ethyl-D-homo-3-methoxygona-2,5(10)-dien-17-aβ-ol (20.5 g), m.p. 141°–143°, λmax. KBr 3.05, 5.88, 5.97 μ.

Hydrolyze dl-13-ethyl-3-methoxy-D-homogona-2,5(10)-dien-17aβ-ol (1.30 g) in methanol (90 cc), concentrated hydrochloric acid (6.0 cc) and water (4.0 cc). Isolate the product and recrystallize from ethyl acetate to obtain the title compound (0.55 g), m.p. 144°–146°, λmax. KBr 2.95, 6.04 μ; λmax. EtOH 240 mμ (ε16,360).

$C_{20}H_{30}O_2$ Calculated: C, 79.43%; H, 10.00%. Found: C, 79.20%; H, 9.93%.

This compound has anabolic and progestational activities.

EXAMPLE 237 dl-17aβ-HYdroxy-13-propyl-D-homogon-4-en-3-one, 3-phenylpropionate

Add phenylpropionyl chloride (0.90 g) in benzene (5.0 cc) to a solution of dl-17aβ-hydroxy-13-propyl-D-homogon-4-en-3-one (0.80 g) in pyridine (5.0 cc), chilled to −15°C. Allow the reaction mixture to stand at −10°C for 16 hours, then at room temperature for 1 hour. Pour into ice water, extract with ether and isolate the crude product. Recrystallize from ethyl acetate-hexane to obtain the title compound (0.45 g), m.p. 166°–169°C, λmax. KBr 5.78, 5.98 μ; λmax. EtOH 240 mμ (ε16,900).

$C_{30}H_{40}O_3$ Calculated: C, 80.31%; H, 8.99%. Found: C, 79.98%; H, 8.64%.

EXAMPLE 238 dl-17aβ-Hydroxy-13-propyl-D-homogon-4-en-3-one, decanoate

Add decanoyl chloride (0.90 g) in benzene (5.0 cc) to dl-17aβ-hydroxy-13-propyl-D-homogon-4-en-3-one (0.80 g) in pyridine (5.0 cc), chilled to 15°C. Allow the reaction mixture to stand at −10° for 16 hours, then at room temperature for 1 hour. Pour into ice water, extract with ether and isolate the crude product. Recrystallize from hexane to obtain the title compound (0.375 g), m.p. 55°–58°C, λmax. KBr 5.78, 5.98 μ; λmax. EtOH 240 mμ (ε15,250).

$C_{31}H_{50}O_3$ Calculated: C, 79.0%; H, 10.70%, Found: C, 78.95%; H, 10.60%.

EXAMPLE 239 dl-13β-Ethyl-17β-hydroxy-7-methylgon-4-en-3-one

Reflux dl-13-ethyl-17β-hydroxygon-4-en-3-one (3.0 g) with acetic anhydride (45 cc), acetyl chloride (24 cc) and pyridine (2.4 cc) for 3 hours. Take to dryness under reduced pressure and partition the residue between benzene-ether and water. Triturate the crude product with hot ether to obtain dl-3,17-diacetoxy-13-ethylgona-3,5-diene (3.125 g), m.p. 148°–156°; λmax.

KBr 5.68, 5.78, 6.0, 6.11 μ; λmax. EtOH 238 mμ (ε19,500).

Add dl-13-ethyl-3,17-dihydroxygona-3,5-diene, diacetate (1.0 g) dissolved in acetone (20 cc) to a solution of acetone (86 cc), pyridine (.59 ml), sodium acetate (2.72 cc), water (27.2 cc) and acetic acid (2.72 cc). Chill to 0° and add N-bromosuccinimide (0.5 g). Stir for three hours at a temperature between +5° and −5°. Pour into ice-cold brine (800 cc) and extract with ether. Wash and dry the ether layer and concentrate, deeping the temperature below +15°. Add calcium carbonate (3.0 g) and dimethylformamide (70 cc) and distil off residual ether. Reflux one hour, cool and filter; wash the cake with ether. Pour the filtrate into brine and extract with ether. Recrystallize from ethyl acetate-hexane to obtain dl-13-ethyl-17β-acetoxygona-4,6-dien-3-one (0.475 g), m.p. 163°–177°, λmax. KBr 5.77, 6.0 μ; λmax. EtOH 283 mμ (ε24,370).

$C_{21}H_{28}O_3$ Calculated: C, 76.80%; H, 8.59%, Found: C, 76.51%; H, 8.58%.

Add dl-13-ethyl-17β-acetoxygona-4,6-dien-3-one (2.0 g) in tetrahydrofuran (30 cc) to tetrahydrofuran (20 cc) containing 3 moles methyl magnesium bromide (16 cc) and cuprous chloride (299 mg) at 0°. Stir for 20 minutes and pour into ice-cold brine saturated with hydrogen chloride. Extract with ether and chromatograph on Grade 2.5 neutral alumina. To obtain the title compound, recrystallize from ethyl acetate-hexane (0.56 g), m.p. 152°–154°; λmax. KBr 2.98, 6.02 μ; λmax. EtOH 242 mμ (ε16,730).

$C_{20}H_{30}O_2$ Calculated: C, 79.43%; H, 10.00%. Found: C, 79.11%; H, 9.92%.

This compound has antiestrogenic activity.

EXAMPLE 240 dl-13,17α-Diethyl-17-hydroxygon-4-en-3-one, acetate

Reflux dl-13,17α-diethyl-17-hydroxygon-4-en-3-one (3.0 g) with acetic anhydride (48 cc), acetyl chloride (24 cc) and pyridine (2.4 cc) for 2 hours. Take the reaction mixture to dryness under reduced pressure and partition the residue between benzene-ether and water. Wash, dry and evaporate the organic layer to obtain the crude dl-13,17α-diethyl-3,17-dihydroxygona-3,5-diene, diacetate. To obtain an analytical sample, triturate the crystalline crude product with ether, filter and wash with hexane, m.p. 122°–125°C; λmax. KBr 5.71, 5.78, 6.0 μ; λmax. EtOH 238 mμ (ε18,200).

$C_{25}H_{36}O_4$ Calculated: C, 74.96%; H, 9.06%. Found : C, 74.64%; H, 9.10%.

Dissolve dl-13,17α-diethyl-3,17-dihydroxygona-3,5-diene, diacetate (3.0 g) in tetrahydrofuran (70 cc) and methanol (70 cc), and chill the solution to 0°C. Add ice-cold 2% potassium in methanol (200 cc) and stir the solution under nitrogen for 1 hour. Pour into brine, make acid with 10% aqueous hydrochloric acid and extract with ether. Wash, dry and evaporate the organic layer and triturate the crystalline residue with ice-cold ether to obtain the title compound (1.45 g), m.p. 121°–123°C; λmax. KBr 5.80, 5.99 μ: λmax. EtOH 240 mμ (ε17,925).

$C_{23}H_{34}O_3$ Calculated: C, 77.05%; H, 9.56%. Found: C, 76.60%; H, 9.81%.

This compound has antiestrogenic activity.

EXAMPLE 241 dl-13-Ethyl-17α-ethynyl-17β-hydroxygon-4-en-3-one, acetate

Reflux dl-13-ethyl-17α-ethynyl-17β-hydroxygon-4-en-3-one (1.0 g) for 1½ hours with acetic anhydride (16 cc), acetyl chloride (8.0 cc) and pyridine (0.8 cc). Remove the liquids under reduced pressure and partition the dry crystalline residue between benzene-ether and water. Wash the organic solvents under reduced pressure and triturate the residue with ice-cold ether to provide dl-13-ethyl-17α-ethynyl-3,17-dihydroxygona-3,5-diene, diacetate (0.725 g), m.p. 144°–150°C; λmax. KBr 3.09, 5.67, 5.77μ; λmax. EtOH 236 mμ (ε19,300).

$C_{25}H_{32}O_4$ Calculated: C, 75.72%; H, 8.11%. Found: C, 75.28%; H, 7.86%.

Dissolve dl-13-ethyl-17α-ethynyl-3,17-dihydroxygona-3,5-diene, diacetate (0.34 g) in methanol (60 cc) and tetrahydrofuran (10 cc) and chill to 0°C. Add 2% potassium in methanol (20 cc) and stir the solution under nitrogen for one hour. Pour into brine, make acid with 10% aqueous hydrochloric acid and extract with ether. Wash the ether with 5% sodium bicarbonate, water and brine. Dry the organic layer and remove the solvent under reduced pressure. Recrystallize the residue from a small amount of ether to provide the title compound (0.200 g), m.p. 162°–164°; λmax. KBr 3.1, 5.72, 6.02 μ; λmax. EtOH 240 mμ (ε18,185).

$C_{23}H_{30}O_3$ Calculated: C, 77.91%; H, 8.53%. Found: C, 77.46%; H, 8.29%.

This compound has progestational activity.

EXAMPLE 242 dl-13-Ethyl-17α-chloroethynyl-17-hydroxygon-4-en-3-one, acetate

Reflux dl-13-ethyl-17α-chloroethynyl-17-hydroxygon-4-en-3-one (3.0 g) for 2 hours with acetic anhydride (48 cc), acetyl chloride (24 cc) and pyridine (2.4 cc). Take the reaction mixture to dryness under reduced pressure and partition the residue between benzene-ether and water. Wash, dry and evaporate the organic phase to obtain the crude dl-13-ethyl-17α-chloroethynyl-3,17-dihydroxygona-3,5-diene, diacetate. Obtain an analytical sample by triturating this crystalline residue with cold ether and washing with hexane, m.p. 177°–180° (d) λmax. KBr 4.50, 5.70, 5.75, 6.0 μ; λmax. EtOH 236 mμ (ε18,800).

$C_{25}H_{31}O_4$ Cl Calculated: C, 69.67%; H, 7.25%. Found: C, 69.93%; H, 7.26%.

Dissolve dl-13-ethyl-17α-chloroethynyl-3,17-dihydroxygona-3,5-diene, diacetate (3.0 g) in tetrahydrofuran (70 cc) and methanol (70 cc) and cool to 0°–5° under nitrogen. Add 2% potassium hydroxide in methanol (200 cc) and stir for 1 hour. Pour into brine, make acid with 10% aqueous hydrochloric acid and extract with ether. Wash, dry evaporate the ether and dissolve the residue in 10% petroleum ether-90% benzene and filter through Grade III neutral alumina (100 g). Remove the solvent and recrystallize the residue from ether-hexane to provide the title compound (1.275 g), m.p. 185°–187°; λmax. KBr 4.52, 5.75, 6.0 μ; λmax. EtOH 240 mμ (ε16,900).

$C_{23}H_{29}O_3$ Cl Calculated: C, 71.03%; H, 7.52%. Found: C, 71.03%; H, 7.69%.

EXAMPLE 243 dl-17β-Hydroxy-17α-ethynylestr-4-en-3-one

Dissolve dl-3-methoxyestra-2,5(10)-dien-17β-ol (4 g) in cyclohexanone (40 ml) and toluene (140 ml) and add a solution of aluminum isopropoxide (4 g) in toluene (56 ml). Reflux in an atmosphere of nitrogen for two hours and cool. Add water (7.5 ml), shake, and then dry by adding sodium sulfate (10 g). Filter and evaporate under vacuum and recrystallize the residue from methanol to obtain dl-3-methoxyestra-2,5(10)-dien-17-one (3.5 g); m.p. 116°–118°; infrared absorption maxima at 5.76 μ, 5.9 μ, 6.01 μ.

This compound has progrestational activity.

Add a solution of dl-3-methoxyestra-2,5(10)-dien-17-one (3.5 g) in dimethylacetamide (100 ml) to a suspension of lithium acetylide (3.7 g) in dioxane (25 ml) and dimethylacetamide (20 ml). Stir for three hours, pour on to ice water (200 g) and extract with ether. Wash, dry, and evaporate the ethereal solution and recrystallize the residue from methanol to obtain dl-17α-ethynyl-3-methoxyestra-2,5(10)-dien-17β-ol (2 g), m.p. 160°–164°; infrared absorption maxima at 2.95 μ, 3.15 μ, 5.9 μ, 6.0 μ.

Dissolve dl-17α-ethynyl-3-methoxyestra-2,5(10)-dien-17β-ol (1 g) in methanol (20 ml) containing concentrated hydrochloric acid (1.2 ml) and water (0.8 ml) and stir for one hour. Add water (250 ml) and extract with ether. Wash, dry and evaporate the ethereal solution and recrystallize the residue from ethyl acetate-ether to obtain the title compound (0.63 g), m.p. 173°–174.5°; ultraviolet absorption peak at 240 mμ (ε17,500); infrared absorption maxima at 3.05 μ, 6.05 μ.

$C_{20}H_{26}O_2$ Calculated: C, 80.49%; H, 8.76%. Found: C, 80.41%, H, 8.82%.

EXAMPLE 244 dl-17α-Ethyl-17-hydroxyestr-4-en-3-one

Add solid lithium acetylide-ethylenediamine complex (9.5 g) to 3-methoxyestra-1,3,5(10),8-tetraen-17-one (10 g) in dimethylacetamide (100 ml), stir the mixture for 15 hours and then pour into ice water. Extract with ether-benzene (1:1), and wash, dry and evaporate the organic extract. Recrystallize the residue from methanol to obtain dl-17α-ethynyl-3-methoxyestra-1,3,5(10),8-tetraen-17-ol (2.8 g), m.p. 133°–137°; infrared absorption peaks at 3.1 μ, 6.25 μ.

Add dl-17α-ethynyl-3-methoxyestra-1,3,5(10),8-tetraen-17-ol (7 g) in benzene (75 ml) to a suspension of prehydrogenated 2% palladised calcium carbonate (3 g) in benzene (50 ml), and shake in an atmosphere of hydrogen until two molecular equivalents of hydrogen (1,030 ml) have been absorbed. Filter the catalyst, evaporate the solvent and recrystallize the residue twice from methanol to obtain dl-17α-ethyl-3-methoxyestra-1,3,5(10),8-tetraen-17-ol (4.5 g), m.p. 105°–120°; ultraviolet absorption maximum 278 mμ (ε12,000); infrared absorption peaks at 2.95 μ, 6.25 μ.

Add dl-17α-ethyl-3-methoxyestra-1,3,5(10),8-tetraen-17-ol (3 g) in tetrahydrofuran (50 ml) to lithium (0.8 g) in aniline (8 ml) and liquid ammonia (200 ml). Stir for 2 hours, decompose by adding ammonium chloride and water, and extract with ether. Wash, dry and evaporate the organic extract, and crystallize from ethyl acetatehexane to obtain dl-17α-ethyl-3-methoxyestra-1,3,5(10)-trien-17β-ol (2 g), m.p. 133°–135°; ultraviolet absorption maximum at 279 mμ (ε2,120).

Add dl-17α-ethyl-3-methoxyestra-1,3,5(10)-trien-17-ol (2 g) in ether (55 ml) to distilled liquid ammonia (180 ml), and add lithium (1 g) to the stirred solution. After 45 minutes add ethanol (15 ml) and ether (15 ml) dropwise followed by ammonium chloride and water. Extract with ether, wash, dry, evaporate, and recrystallize the residue from ether to obtain dl-17α-ethyl-3-methoxyestra-2,5(10)-dien-17-ol (1.4 g), m.p. 131°–134°.

Stir dl-17α-ethyl-3-methoxyestra-2,5(10)-dien-17-ol (1.4 g) with concentrated hydrochloric acid (2.4 ml) in water (1.6 ml) and methanol (36 ml) for 2 hours. Add water, extract with ether and wash, dry and evaporate the ethereal solution. Recrystallize the product from ethyl acetate-ether to obtain the title compound (0.63 g), m.p. 173°–174.5°; ultraviolet absorption maximum at 240 mμ (ε17,500).

$C_{20}H_{26}O_2$ Calculated: C, 80.5%; H, 8.7%. Found: C, 80.4%; H, 8.8%.

This compound has anabolic activity.

EXAMPLE 245 dl-13-Ethyl-17β-hydroxy-17α-(1-hydroxyethyl)gon-4-en-3-one

Reduce dl-13-ethyl-17α-acetyl-3-methoxygona-1,3,5(10)-triene (1 g) with lithium aluminum hydride in ether to dl-13-ethyl-17-(1-hydroxyethyl)-3-methoxygona-1,3,5(10)-triene. Reduce this alcohol (0.9 g) with lithium (0.7 g) and ethanol in liquid ammonia (150 cc)-tetrahydrofuran (60 cc) to dl-13-ethyl-17β-hydroxy-17α-(1-hydroxyethyl)-3-methoxygona-2,5(10)-diene. Hydrolyse this substance with methanolic hydrochloric acid and recrystallize the product from ethyl acetate to obtain the title substance, m.p. 159°–164°, λmax. 240 mμ (ε15,230).

$C_{21}H_{32}O_3$ Calculated: C, 75.85%; H, 9.7%. Found: C, 76.1%; H, 9.8%.

This compound has progestational activity.

EXAMPLE 246

13-Ethyl-17β-hydroxygon-4-en-3-one, 2'-tetrahydropyranyl ether

Add 2 drops of concentrated hydrochloric acid to 13-ethyl-17β-hydroxygon-4-en-3-one (0.5 g), 2,3-dihydropyran (5 ml), and ether (3 ml). Keep the mixture for 3 days at room temperature then dilute it with ether and add sodium bicarbonate. Recrystallize the product from hexane to obtain the title substance, m.p. 110°–140°.

$C_{24}H_{36}O_3$ Calculated: C, 77.4%; H, 9.7%. Found: C, 77.15%; H, 9.5%.

This compound has anabolic activity.

EXAMPLE 247 dl-13-Ethyl-17β-(2-hydroxyethoxy)gon-4-en-3-one, benzoate

Stir a solution of 4.0 g. of dl-13-ethyl-17β-(2-hydroxyethoxy)-3-methoxygona-1,3,5(10)-triene, 300 ml. of tetrahydrofuran, and 300 ml. of liquid ammonia. Add 4.0 g. of lithium and stir for 1 hour. Discolor with absolute alcohol, add water and filter off the precipitate; infrared peaks at 2.91, 5.89, 6.00 μ.

Stir a suspension of 1.7 g. of the foregoing enol ether, 100 ml. of methanol, 8 ml. of conc. hydrochloric acid, and 5 ml. of water for 2 hours. Dilute with water and extract the material with ether. Evaporate the ether to obtain a gum.

Treat a solution of 1.3 g. of this crude material in 6 ml. of pyridine with 1.3 ml. of benzoyl chloride at −10°. Keep the solution at −10° for 22 hours, then pour it over ice and extract the mixture with ether. Chromatograph the product on alumina. Elute with benzene-ethyl acetate to obtain the title substance; infrared peaks at 5.80, 5.98 $\mu$.

$C_{28}H_{36}O_4$ Calculated: C, 77.03%; H, 8.31%. Found: C, 77.44%; H, 8.59%.

This compound has anabolic activity.

EXAMPLE 248 dl-17$\beta$-Ethoxy-13-ethylgon-4-en-3-one

Reflux a suspension of 5.0 g. of dl-13-ethyl-3-methoxygona-1,3,5(10)-trien-17$\beta$-ol and 3.83 g. of sodium hydride (50% in oil) for 1.5 hours in xylene (100 ml). Add 14.5 ml. of ethyl iodide and reflux for 22 hours. Acidify with 2N hydrochloric acid and extract the material with benzene. Chromatograph the residue on alumina (Grade I neutral). Elute the product with benzene-ether (1:1). Recrystallize the product from 60 ml. of methanol to obtain dl-17$\beta$-ethoxy-13-ethyl-3-methoxygona-1,3,5(10)-triene (2.3 g); m.p. 74°–77°C.

$C_{22}H_{32}O_2$ Calculated: C, 80.44%; H, 9.83%. Found: C, 80.73%; H, 10.09%.

Add 2.0 g. of lithium to a suspension of 2.0 g. of dl-17$\beta$-ethoxy-13-ethyl-3-methoxygona-1,3,5(10)-triene, 90 ml. of 1,2-dimethoxyethane, 100 ml. of 1-methoxy-2-propanol, and 300 ml. of ammonia while stirring. Treat with 2.0 g. of ammonium chloride and water, filter off the precipitate and add it to 80 ml. of methanol, 4 ml. of water, and 5 ml. of conc. hydrochloric acid. Stir for one hour and dilute with water. Extract the product with ether and recrystallize it successively from methanol-water and petroleum ether-ether to obtain the title substance, m.p. 95°–97°; ultraviolet peak at 244 m$\mu$ (15,900); infrared peak at 6.0 $\mu$.

$C_{21}H_{32}O_2$ Calculated: C, 79.70%; H, 10.19%. Found: C, 79.90%, H, 10.38%.

This compound has progestational and anabolic activities.

EXAMPLE 249 dl-13-Ethyl-17$\beta$-(1-hydroxy-2,2,2-trichloroethoxy)-gon-4-en-3-one

Add 2.9 g. of dl-13-ethyl-17$\beta$-hydroxygon-4-en-3-one to a solution of 1.9 g. of chloral hydrate in 10 ml. of benzene at 5°C. Keep the mixture overnight at this temperature. Filter off the product and recrystallize it successively from ethyl acetate and petroleum ether-benzene to obtain the title substance, m.p. 175°–176°; ultraviolet peak at 240 m$\mu$ ($\epsilon$17,500); infrared peaks at 3.10, 6.05, 6.20 $\mu$.

$C_{21}H_{29}Cl_3O_3$ Calculated: C, 57.87%; H, 6.71%; Cl, 24.41%. Found: C, 57.82%; H, 6.64%; Cl, 24.2%.

This compound has anabolic and progestational activities.

EXAMPLE 250 dl-13-Ethyl-17$\beta$-(1-hydroxy-2,2,2-trichloroethoxy)-gon-4-en-3-one, acetate

Keep a solution of 1.5 g. of 13-ethyl-17$\beta$-(1-hydroxy-2,2,2-trichloroethoxy)gon-4-en-3-one in acetic anhydride (5 ml) and pyridine (5 ml) for 3 days. Evaporate the solvent afterwards and reflux the residue with methanol for a few minutes. Cool and filter off the title substance (1.2 g); m.p. 183°–183°; ultraviolet peak at 240 m$\mu$ ($\epsilon$17,500).

$C_{23}H_{31}Cl_3O_4$ Calculated: C, 57.81%; H, 6.54%; Cl, 22.26%. Found: C, 57.76%; H, 6.37%; Cl, 22.2%.

This compound has anabolic and progestational activities.

EXAMPLE 251 dl-13-Ethyl-17$\beta$-propoxygon-4-en-3-one

Reflux a suspension of 5.0 g. of dl-13-ethyl-3-methoxygona-1,3,5(10)-triene-17$\beta$-ol, 100 mg. of xylene, and 3.9 g. of sodium hydride (50% in mineral oil) for 1.5 hours. Add 14.5 ml. of allyl bromide and reflux for 22 hours. Make the reaction mixture acidic with dilute hydrochloric acid and extract the organic layer with sodium bicarbonate solution. Chromatograph the residue on alumina (Grade I neutral) in hexane and elute the product with ether to obtain dl-17$\beta$-allyloxy-13-ethyl-3-methoxygona-1,3,5(10)-triene.

Hydrogenate 3.0 g. of dl-17$\beta$-allyloxy-13-ethyl-3-methoxygona-1,3,5(10)-triene in 100 ml. of benzene and 1.0 g. of 10% palladized charcoal at atmospheric pressure. Filter off the catalyst and recrystallize the residue from methanol to obtain 2.3 g. of the desired product, m.p. 83°–84°C; $\lambda$max. 279 ($\epsilon$2,010).

$C_{23}H_{34}O_2$ Calculated: C, 80.65%; H, 10.01% Found: C, 80.42%; H, 9.80%

Treat a suspension of 1.5 g. of dl-13-ethyl-3-methoxy-17$\beta$-propoxygona-1,3,5(10)-triene, 75 ml. of 1,2-dimethoxyethane, 75 ml. of 1-methoxy-2-propanol, and 300 ml. of liquid ammonia with 5.0 g. of lithium. When the reaction ends add 1.5 g. of ammonium chloride and water. Collect the precipitate of dl-13-ethyl-3-methoxy-17$\beta$-propoxygona-2,5(10)-diene, and add it to a solution of 50 ml. of methanol, 5 ml. of conc. hydrochloric acid, and 4 ml. of water. Stir for 0.5 hours. Filter off a small amount of insoluble material. Add water to clean solution and extract with ether. Recrystallize from etherpetroleum ether to obtain the title product, m.p. 88°–89°; ultraviolet peak at 242 m$\mu$ ($\epsilon$16,600); infrared peaks at 6.00, 6.19$\mu$.

$C_{22}H_{34}O_2$ Calculated: C, 79.95%; H, 10.37%. Found: C, 80.02%; H, 10.20%.

This compound has anabolic activity.

EXAMPLE 252 dl-17-Chloroethynyl-13-ethylgon-4-en-3,17$\beta$-diol

Stir a solution of (5.0 g) dl-17-chloroethynyl-17$\beta$-hydroxy-13-ethylgon-4-en-3-one and 150 ml. of absolute alcohol (ice-bath), add 2.0 g. of sodium borohydride and continue to stir for three hours at room temperature. Add acetic acid and water and extract with ether. Wash the ether solution with sodium bicarbonate solution. Evaporate the solvent to obtain 5.0 g. of the title product; no infrared absorption in the 6 $\mu$ region.

This compound has pituitary-blocking activity.

EXAMPLE 253 dl-17-Chloroethynyl-13-ethylgon-4-ene-3,17$\beta$-diol, 3-acetate

Treat a mixture of 2.0 g. of dl-17-chloroethynyl-13-ethylgon-4-ene-3,17$\beta$-diol, 10 mg. of pyridine with 15 ml. of acetic anhydride. Keep the solution overnight at room temperature, and then pour it into ice-water; acidify with 2 N hydrochloric acid and extract with ether. Evaporate the ether and crystallize residue from methanol-water to obtain 900 mg. of desired product, m.p. 156°–160°; infrared peaks at 2.90, 4.54, 5.80, 6.00 μ.

$C_{23}H_{31}O_3Cl$ Calculated: Cl, 9.09%. Found; Cl, 9.01%. This compound has progestational activity.

EXAMPLE 254 dl-17β-(2-Diethylaminoethoxy)-13-ethylgon-4-en-3-one, citrate

Stir a solution of 100 ml. of ether, 13.3 g. aluminum chloride and 15 ml. of lithium aluminum hydride (1 molar solution) for 40 minutes. Add a solution of 17.1 g. of dl-13-ethyl-17,17-ethylenedioxy-3-methoxygona-1,3,5(10)-triene in 1 liter of ether and stir for 4 hours. Dilute with 2 N sulfuric acid until clear solution results. Separate the ether layer and evaporate the solvent. Treat residue with 20 ml. of ethanol, 5 ml. of conc. hydrochloric acid, and 10 ml. of water on steam bath for 30 minutes. Crystallize the product from ethanol to obtain 8.1 g. dl-13-ethyl-17β-(2-hydroxyethoxy)-3-methoxygona-1,3,5(10)-triene; m.p. 131°–132°.

$C_{22}H_{32}O_3$ Calculated: C, 76.70%; H, 9.36%. Found: C, 76.81%; H, 9.35%.

Stir a cooled solution of 344 mg. of dl-13-ethyl-17β-(2-hydroxyethoxy)-3-methoxygona-1,3,5(10)-triene in 2 ml. of pyridine (acetone-dry ice bath) and add dropwise 0.14 ml. of methanesulfonyl chloride. After 2 hours bring reaction mixture to room temperature. Mix with ice and water and a few drops of methanol to obtain a crystalline precipitate. Recrystallize this to obtain dl-13-ethyl-17β-(2-hydroxyethoxy)-3-methoxygona-1,3,5(10)-triene methane sulfonate from methanol (310 mg); m.p. 104°.

$C_{23}H_{34}O_5S$ Calculated: C, 65.37%; H, 8.11%; S, 7.60%. Found: C, 65.62%; H, 8.22%, S, 7.85%.

Reflux a suspension of 2.3 g. of the foregoing ester with 50 ml. of diethylamine for 6 hours. Evaporate the solvent and treat the residue with aqueous acetic acid. Extract the non-basic fraction with ether. Basify the acidic layer and separate the product with ether. Recrystallize from methanol-water to obtain dl-13-ethyl-17β-(2-diethylaminoethoxy)-3-methoxygona-1,3,5(10)-triene; m.p. 66°–67°.

$C_{26}H_{41}NO_2$ Calculated: C, 78.14%; H, 10.34%; N, 3.51%. Found: C, 77.85%; H, 10.03%; N, 3.52%.

Add 3.0 g. of lithium to a stirred solution of 4.0 g. of 17β-(2-diethylaminoethoxy)-13-ethyl-3-methoxygona-1,3,5(10)-triene, 200 ml. of morpholine, 200 ml. of tetrahydrofuran, 100 ml. of 1-methoxy-2-propanol, and 500 ml. of liquid ammonia. Treat with 25.0 g. of ammonium chloride and water and extract with ether to obtain 3.0 g. of dl-13-ethyl-17β-(2-diethylaminoethoxy)-3-methoxygona-2,5(10)-diene.

Add 50 ml. methanol, 5 ml. of conc. hydrochloric acid and 4 ml. of water to the foregoing enol ether and stir for 2 hours. Add sodium hydroxide solution (10%) and extract product with ether. Purify product by chromatography on alumina (Grade I neutral). Evaporate the methanol eluate, dissolve the residue in 100 ml. of ether and add 650 mg. of citric acid hydrate in 600 ml. of ether to the solution. Filter precipitate to obtain the title product (0.9 g).

$C_{31}H_{49}NO_9$ Calculated: N, 2.42%. Found: N, 2.61%.

EXAMPLE 255 dl-13-Ethyl-17α-ethynyl-17β-hydroxy-7α-methylgon-4-en-3-one

Reflux dl-13-ethyl-17β-hydroxy-7α-methylgon-4-en-3-one (1.35 g) in benzene (100 ml) with ethylene glycol (10 cc) and p-toluene-sulfonic acid hydrate (67 mg) for 6 hours using a water separator. Wash, dry and evaporate the solvent to obtain the dl-13-ethyl-3,3-ethylenedioxy-17β-hydroxy-7α-methylgon-5 and 5(10)-ene, as a gum, λmax. NaCl 2.90 μ.

Subject dl-13-ethyl-3,3-ethylenedioxy-17β-hydroxy-7α-methylgon-5 and 5(10)-ene (1.4 g) to Oppenauer oxidation by refluxing in the presence of toluene (50 cc), cyclohexanone (10 cc) and aluminum isopropoxide (0.80 g) for 3.5 hours.

Isolate the dl-13-ethyl-3,3-ethylenedioxy-7α-methylgon-5 and 5(10)-ene-17-one as a gum by addition of water (0.5 cc), sodium sulfate anhydrous (6.0 g), filtration and concentration under high vacuum, λmax. NaCl 2.9, 5.75, 5.85 μ.

Dissolve dl-13-ethyl-3,3-ethylenedioxy-7α-methylgon-5 and 5(10)-en-17-one (1.3 g) in dimethylacetamide (50 cc) and stir in a stream of acetylene in the presence of lithium acetylide-ethylenediamine (1.0 g) for 2 hours. Add ice, extract with ether and isolate the crude dl-13-ethyl-3,3-ethylendioxy-17α-ethynyl-17β-hydroxy-7α-methylgon-5 and 5(10)-ene (0.8 g). Infrared spectral data indicate no ketone remaining.

Dissolve crude dl-13-ethyl-3,3-ethylenedioxy-17α-ethynyl-17-hydroxy-7α-methylgon-5 and 5(10)-ene (0.8 g) in methanol (50 cc), hydrochloric acid (3.0 cc) and water (2.0 cc), and stir under nitrogen for 1.5 hours. Pour into brine, extract with ether and isolate the crude product as a crystalline solid, m.p. 170°–175°. Chromatograph on Florex XXS (40.0 g) and recrystallize from ethyl acetate-hexane to obtain the title compound (0.550 g), m.p. 182°–184°C, λmax. KBr 3.0, 3.1, 4.80, 6.09 μ.

$C_{22}H_{30}O_2$ Calculated: C, 80.92%; H, 9.26%. Found; C, 80.62%; H, 9.13%.

EXAMPLE 256 dl-13-Ethyl-17β-(2-dimethylaminoethoxy)gon-4-en-3-one

Stir a solution of 860 mg. of sodium amide in 15 ml. of benzene and add 3.0 g. of dl-13-ethyl-3-methoxygona-1,3,5(10)-trien-17β-ol in 15 ml. of benzene. Heat for 2 hours at 70°–83°. Cool to room temperature and add 1.58 g. of N,N-dimethylamino-2-chloroethane hydrochloride and reflux for 16 hours. Pour over ice and acidify reaction mixture with 2 N hydrochloric acid. Extract with ether and basify the aqueous layer with 15% sodium hydroxide. Isolate material with ether. Evaporate the ether to obtain dl-13-ethyl-17β-(2-dimethylaminoethoxy)-3-methoxygona-1,3,5(10)-triene.

Add to a solution of 400 mg. of dl-13-ethyl-17β-(2-dimethylaminoethoxy)-3-methoxygona-1,3,5(10)-triene, 75 ml. of tetrahydrofuran, and 120 ml. of liquid ammonia, 500 mg. of lithium while stirring for 3 hours. Add absolute alcohol until the reaction mixture turns colorless. Add 6.0 g. of ammonium chloride and water, and filter off the precipitate.

Stir this material with a solution of 12 ml. of methanol and 1 ml. of 2 N hydrochloric acid for 1 hour. Basify with 10% sodium hydroxide and collect the precipitate. Recrystallize the product from methanol-water to obtain the title compound, m.p. 87°–88°.

$C_{23}H_{37}O_2N$ Calculated: C, 76.83%; H, 10.37%; N, 3.90%. Found: C, 76.69%; H, 10.22%; N, 4.06%.

The subject matter which the applicants regard as their invention is particularly pointed out and distinctly claimed as follows:

1. A therapeutic composition having progestational activity comprising as active ingredient a 17-aliphatic carboxylic acid ester of 17α-ethynyl-18-methyl-19-nortestosterone and a pharmaceutical carrier for said compound.

2. A composition according to claim 1 wherein said nortestosterone 17-ester is the 17-acetate ester.

3. A therapeutic composition having progestational activity in which the active ingredient is a 17α-ethynyl-18-methyl-19-nortestosterone 17-aliphatic carboxylic acid ester present in a progestationally effective amount.

4. A therapeutic composition according to claim 3 wherein said ester is 17α-ethynyl-18-methyl-19-nortestosterone 17-acetate.

5. A method of providing steroid therapy which comprises administering to a subject a therapeutic composition according to claim 3.

* * * * *